US007763050B2

(12) United States Patent
Winslow et al.

(10) Patent No.: US 7,763,050 B2
(45) Date of Patent: Jul. 27, 2010

(54) INTER-CERVICAL FACET IMPLANT WITH LOCKING SCREW AND METHOD

(75) Inventors: Charles J. Winslow, Walnut Creek, CA (US); James F. Zucherman, San Francisco, CA (US); Ken Y. Hsu, San Francisco, CA (US); Steven T. Mitchell, Pleasant Hill, CA (US); Scott A. Yerby, Montara, CA (US); John J. Flynn, West Milford, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 49 days.

(21) Appl. No.: 11/093,557

(22) Filed: Mar. 30, 2005

(65) Prior Publication Data
US 2006/0149239 A1 Jul. 6, 2006

Related U.S. Application Data

(60) Provisional application No. 60/635,453, filed on Dec. 13, 2004.

(51) Int. Cl.
*A61B 17/70* (2006.01)
(52) U.S. Cl. .................................................. 606/247
(58) Field of Classification Search .................. 606/61, 606/69, 70, 71
See application file for complete search history.

(56) References Cited

U.S. PATENT DOCUMENTS

| 2,456,806 | A | 12/1948 | Wolffe |
| 2,677,369 | A | 5/1954 | Knowles |
| 3,426,364 | A | 2/1969 | Lumb |
| 3,643,658 | A | 2/1972 | Steinemenan |
| 3,648,691 | A | 3/1972 | Lumb |
| 3,867,728 | A | 2/1975 | Stubstad |
| 3,875,595 | A | 4/1975 | Froning |
| 3,879,767 | A | 4/1975 | Stubstad |
| 3,933,075 | A * | 1/1976 | Peterson .................. 411/387.7 |
| 4,001,896 | A | 1/1977 | Arkangel |
| 4,034,418 | A | 7/1977 | Jackson |
| 4,085,466 | A | 4/1978 | Goodfellow et al. |

(Continued)

FOREIGN PATENT DOCUMENTS

CA 2015507 1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1819-1825, © 1997, Lippincott-Raven Publishers.

(Continued)

*Primary Examiner*—Thomas C Barrett
*Assistant Examiner*—Nicholas Woodall

(57) ABSTRACT

Systems and method in accordance with the embodiments of the present invention can include an implant for positioning within a cervical facet joint for distracting the cervical spine, thereby increasing the area of the canals and openings through which the spinal cord and nerves must pass, and decreasing pressure on the spinal cord and/or nerve roots. The implant can be inserted laterally or posteriorly.

37 Claims, 27 Drawing Sheets

U.S. PATENT DOCUMENTS

| | | |
|---|---|---|
| 4,156,296 A | 5/1979 | Johnson et al. |
| 4,219,015 A | 8/1980 | Steinemenan |
| 4,231,121 A | 11/1980 | Lewis |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |
| 4,455,690 A | 6/1984 | Homsy |
| 4,479,491 A | 10/1984 | Martin |
| 4,501,269 A | 2/1985 | Bagby |
| 4,502,161 A | 3/1985 | Wall |
| 4,553,273 A | 11/1985 | Wu |
| 4,554,914 A | 11/1985 | Kapp |
| 4,599,084 A | 7/1986 | Nashef |
| 4,599,086 A | 7/1986 | Doty |
| 4,604,995 A | 8/1986 | Stephens |
| 4,611,582 A | 9/1986 | Duff |
| 4,636,217 A | 1/1987 | Ogilvie |
| 4,643,178 A | 2/1987 | Nastari |
| 4,657,550 A | 4/1987 | Daher |
| 4,685,447 A | 8/1987 | Iversen |
| 4,696,290 A | 9/1987 | Steffee |
| 4,714,469 A | 12/1987 | Kenna |
| 4,743,256 A | 5/1988 | Brantigan |
| 4,759,769 A | 7/1988 | Hedman et al. |
| 4,772,287 A | 9/1988 | Ray |
| 4,790,303 A | 12/1988 | Steffee |
| 4,834,757 A | 5/1989 | Brantigan |
| 4,863,477 A | 9/1989 | Monson |
| 4,878,915 A | 11/1989 | Brantigan |
| 4,904,260 A | 2/1990 | Ray |
| 4,904,261 A | 2/1990 | Dove |
| 4,911,718 A | 3/1990 | Lee et al. |
| 4,913,134 A | 4/1990 | Luque |
| 4,923,471 A | 5/1990 | Morgan |
| 4,932,975 A | 6/1990 | Main |
| 4,936,848 A | 6/1990 | Bagby |
| 4,946,378 A | 8/1990 | Hirayama |
| 4,961,740 A | 10/1990 | Ray |
| 4,969,888 A | 11/1990 | Scholten |
| 5,011,484 A | 4/1991 | Breard |
| 5,015,247 A | 5/1991 | Michelson |
| 5,015,255 A | 5/1991 | Kuslich |
| 5,026,373 A | 6/1991 | Ray |
| 5,035,716 A | 7/1991 | Downey |
| 5,047,055 A | 9/1991 | Bao |
| 5,055,104 A | 10/1991 | Ray |
| 5,059,193 A | 10/1991 | Kuslich |
| 5,059,194 A | 10/1991 | Michelson |
| 5,062,845 A | 11/1991 | Kuslich |
| 5,062,850 A | 11/1991 | MacMillan |
| 5,071,437 A | 12/1991 | Steffee |
| 5,074,864 A | 12/1991 | Cozad |
| 5,084,049 A | 1/1992 | Asher et al. |
| 5,088,869 A | 2/1992 | Greenslade |
| 5,092,866 A | 3/1992 | Breard |
| 5,105,255 A | 4/1992 | Shannon |
| 5,122,130 A | 6/1992 | Keller |
| 5,123,926 A | 6/1992 | Pisharodi |
| 5,127,912 A | 7/1992 | Ray |
| 5,147,404 A | 9/1992 | Downey |
| 5,167,662 A | 12/1992 | Hayes |
| 5,167,665 A | 12/1992 | McKinney |
| 5,171,280 A | 12/1992 | Baumgartner |
| 5,180,381 A | 1/1993 | Aust |
| 5,192,326 A | 3/1993 | Bao et al. |
| 5,192,327 A | 3/1993 | Brantigan |
| 5,258,031 A | 11/1993 | Salib |
| 5,263,953 A | 11/1993 | Bagby |
| 5,275,601 A | 1/1994 | Gogolewski |
| 5,290,312 A | 3/1994 | Kojimoto |
| 5,300,073 A | 4/1994 | Ray |
| 5,304,178 A | 4/1994 | Stahurski |
| 5,306,275 A | 4/1994 | Bryan |
| 5,306,308 A | 4/1994 | Gross et al. |
| 5,306,309 A | 4/1994 | Wagner |
| 5,352,225 A | 10/1994 | Yuan |
| 5,360,431 A | 11/1994 | Puno et al. |
| 5,366,455 A | 11/1994 | Dove |
| 5,370,697 A | 12/1994 | Baumgartner |
| 5,387,213 A | 2/1995 | Breard |
| 5,390,683 A | 2/1995 | Pisharodi |
| 5,391,168 A | 2/1995 | Sanders |
| 5,395,372 A | 3/1995 | Holt |
| 5,401,269 A | 3/1995 | Buttner-Janz et al. |
| 5,415,661 A | 5/1995 | Holmes |
| 5,425,773 A | 6/1995 | Boyd et al. |
| 5,437,672 A | 8/1995 | Alleyne |
| 5,443,514 A | 8/1995 | Steffee |
| 5,445,639 A | 8/1995 | Kuslich et al. |
| 5,454,812 A | 10/1995 | Lin |
| 5,456,722 A | 10/1995 | McLeod |
| 5,458,638 A | 10/1995 | Kuslich |
| 5,458,641 A | 10/1995 | Jimenez |
| 5,458,642 A | 10/1995 | Beer et al. |
| 5,458,643 A | 10/1995 | Oka |
| 5,468,242 A | 11/1995 | Reisberg |
| 5,470,333 A | 11/1995 | Ray |
| 5,491,882 A | 2/1996 | Walston |
| 5,496,318 A | 3/1996 | Howland |
| 5,505,732 A | 4/1996 | Michelson |
| 5,507,745 A | 4/1996 | Logroscino |
| 5,507,823 A | 4/1996 | Walston |
| 5,514,180 A | 5/1996 | Heggeness |
| 5,527,312 A | 6/1996 | Ray |
| 5,527,314 A | 6/1996 | Brumfield et al. |
| 5,531,747 A | 7/1996 | Ray |
| 5,534,028 A | 7/1996 | Bao |
| 5,534,029 A | 7/1996 | Shima |
| 5,534,030 A | 7/1996 | Navarro et al. |
| 5,540,689 A | 7/1996 | Sanders |
| 5,545,229 A | 8/1996 | Parsons et al. |
| 5,549,679 A | 8/1996 | Kuslich |
| 5,554,191 A | 9/1996 | Lahille |
| 5,556,431 A | 9/1996 | Buttner-Janz |
| 5,562,736 A | 10/1996 | Ray |
| 5,562,738 A | 10/1996 | Boyd et al. |
| 5,571,189 A | 11/1996 | Kuslich |
| 5,571,191 A | 11/1996 | Fitz |
| 5,577,995 A | 11/1996 | Walker |
| 5,584,832 A | 12/1996 | Schlapfer |
| 5,591,165 A | 1/1997 | Jackson |
| 5,593,409 A | 1/1997 | Michelson |
| 5,601,553 A | 2/1997 | Trebing |
| 5,603,713 A | 2/1997 | Aust |
| 5,609,634 A | 3/1997 | Voydeville |
| 5,616,142 A | 4/1997 | Yuan |
| 5,623,984 A | 4/1997 | Nozaki |
| 5,628,756 A | 5/1997 | Barker, Jr. |
| 5,645,597 A | 7/1997 | Krapiva |
| 5,645,599 A | 7/1997 | Samani |
| 5,653,761 A | 8/1997 | Pisharodi |
| 5,653,762 A | 8/1997 | Pisharodi |
| 5,658,286 A | 8/1997 | Sava |
| 5,672,177 A | 9/1997 | Seldin |
| 5,674,295 A | 10/1997 | Ray |
| 5,674,296 A | 10/1997 | Bryan |
| 5,676,701 A | 10/1997 | Yuan et al. |
| 5,676,702 A | 10/1997 | Ratron |
| 5,683,464 A | 11/1997 | Wagner et al. |
| 5,702,450 A | 12/1997 | Bisserie |
| 5,702,455 A | 12/1997 | Saggar |
| 5,716,415 A | 2/1998 | Steffee |
| 5,725,582 A | 3/1998 | Bevan |

| Patent No. | Date | Inventor | | Patent No. | Date | Inventor |
|---|---|---|---|---|---|---|
| 5,741,261 A | 4/1998 | Moskovitz | | 6,470,207 B1 | 10/2002 | Simon et al. |
| 5,766,251 A | 6/1998 | Koshino | | 6,527,776 B1 | 3/2003 | Michelson |
| 5,766,252 A | 6/1998 | Henry | | 6,540,785 B1 * | 4/2003 | Gill et al. ............... 623/17.14 |
| 5,766,253 A | 6/1998 | Brosnahan, III | | 6,558,423 B1 | 5/2003 | Michelson |
| 5,800,438 A | 9/1998 | Tuke | | 6,558,686 B1 | 5/2003 | Darouiche |
| 5,814,070 A * | 9/1998 | Borzone et al. ............ 606/232 | | 6,565,570 B2 | 5/2003 | Sterett |
| 5,824,093 A | 10/1998 | Ray et al. | | 6,565,605 B2 | 5/2003 | Goble |
| 5,824,094 A | 10/1998 | Serhan et al. | | 6,572,653 B1 * | 6/2003 | Simonson ............... 623/17.13 |
| 5,824,098 A | 10/1998 | Stein | | 6,579,318 B2 | 6/2003 | Varga |
| 5,836,948 A | 11/1998 | Zucherman | | 6,579,319 B2 | 6/2003 | Goble |
| 5,860,977 A | 1/1999 | Zucherman | | 6,582,437 B2 | 6/2003 | Dorchak |
| 5,865,846 A | 2/1999 | Bryan | | 6,592,586 B1 | 7/2003 | Michelson |
| 5,868,745 A | 2/1999 | Alleyne | | 6,610,091 B1 | 8/2003 | Reiley |
| 5,876,402 A | 3/1999 | Errico | | 6,620,163 B1 | 9/2003 | Michelson |
| 5,876,404 A | 3/1999 | Zucherman | | 6,669,729 B2 | 12/2003 | Chin |
| 5,879,396 A | 3/1999 | Walston | | 6,712,852 B1 | 3/2004 | Chung |
| 5,885,299 A | 3/1999 | Winslow | | 6,730,127 B2 | 5/2004 | Michelson |
| 5,888,224 A | 3/1999 | Beckers | | 6,740,088 B1 * | 5/2004 | Kozak et al. ............... 606/69 |
| 5,888,226 A | 3/1999 | Rogozinski | | 6,752,831 B2 | 6/2004 | Sybert |
| 5,893,889 A | 4/1999 | Harrington | | 6,755,841 B2 | 6/2004 | Fraser |
| RE36,221 E | 6/1999 | Breard et al. | | 6,761,720 B1 | 7/2004 | Senegas |
| 5,951,555 A | 9/1999 | Rehak | | 6,764,491 B2 | 7/2004 | Frey et al. |
| 5,976,186 A | 11/1999 | Bao | | 6,783,527 B2 | 8/2004 | Drewry |
| 6,001,130 A | 12/1999 | Bryan | | 6,800,670 B2 | 10/2004 | Shen |
| 6,014,588 A | 1/2000 | Fitz | | 6,811,567 B2 | 11/2004 | Reiley |
| 6,019,792 A | 2/2000 | Cauthen | | 6,902,566 B2 | 6/2005 | Zucherman et al. |
| 6,022,376 A | 2/2000 | Assell | | 6,974,478 B2 | 12/2005 | Reiley et al. |
| 6,030,162 A | 2/2000 | Huebner | | 6,974,479 B2 * | 12/2005 | Trieu ....................... 623/17.11 |
| 6,039,763 A | 3/2000 | Shelokov | | 7,008,427 B2 * | 3/2006 | Sevrain ....................... 606/71 |
| 6,045,554 A | 4/2000 | Grooms | | 7,101,375 B2 | 9/2006 | Zucherman et al. |
| 6,048,204 A | 4/2000 | Klardie | | 7,108,698 B2 * | 9/2006 | Robbins et al. ............... 606/90 |
| 6,048,342 A | 4/2000 | Zucherman | | 2001/0012938 A1 | 8/2001 | Zucherman |
| 6,048,344 A | 4/2000 | Schenk | | 2001/0018614 A1 | 8/2001 | Bianchi |
| 6,063,121 A | 5/2000 | Xavier et al. | | 2002/0004683 A1 | 1/2002 | Michelson |
| 6,066,325 A | 5/2000 | Wallace et al. | | 2002/0016595 A1 | 2/2002 | Michelson |
| 6,068,630 A | 5/2000 | Zucherman | | 2002/0022843 A1 | 2/2002 | Michelson |
| RE36,758 E | 6/2000 | Fitz | | 2002/0029079 A1 | 3/2002 | Zucherman et al. |
| 6,080,157 A | 6/2000 | Cathro et al. | | 2002/0065557 A1 | 5/2002 | Goble |
| 6,093,205 A * | 7/2000 | McLeod et al. .......... 623/17.16 | | 2002/0072800 A1 | 6/2002 | Goble |
| 6,099,531 A | 8/2000 | Bonutti | | 2002/0077700 A1 | 6/2002 | Varga |
| 6,113,637 A | 9/2000 | Gill et al. | | 2002/0099376 A1 | 7/2002 | Michelson |
| 6,113,639 A | 9/2000 | Ray | | 2002/0128655 A1 | 9/2002 | Michelson |
| 6,129,730 A | 10/2000 | Bono | | 2002/0133155 A1 | 9/2002 | Ferree |
| 6,132,464 A | 10/2000 | Martin | | 2002/0151895 A1 | 10/2002 | Soboleski |
| 6,132,465 A | 10/2000 | Ray et al. | | 2002/0183756 A1 | 12/2002 | Michelson |
| 6,139,550 A | 10/2000 | Michelson | | 2002/0183757 A1 | 12/2002 | Michelson |
| 6,152,927 A | 11/2000 | Farris | | 2002/0188296 A1 | 12/2002 | Michelson |
| 6,156,067 A | 12/2000 | Bryan | | 2003/0004572 A1 | 1/2003 | Goble |
| 6,190,414 B1 | 2/2001 | Young | | 2003/0028250 A1 | 2/2003 | Reiley |
| 6,193,721 B1 | 2/2001 | Michelson | | 2003/0040746 A1 | 2/2003 | Mitchell |
| 6,200,322 B1 | 3/2001 | Branch | | 2003/0060828 A1 | 3/2003 | Michelson |
| 6,206,922 B1 | 3/2001 | Zdeblick | | 2003/0078668 A1 | 4/2003 | Michelson |
| 6,217,580 B1 | 4/2001 | Levin | | 2003/0181912 A1 | 9/2003 | Michelson |
| 6,224,602 B1 | 5/2001 | Hayes | | 2003/0187454 A1 | 10/2003 | Gill et al. |
| 6,224,607 B1 | 5/2001 | Michelson | | 2003/0191471 A1 | 10/2003 | Michelson |
| 6,228,900 B1 | 5/2001 | Shen | | 2003/0191472 A1 | 10/2003 | Michelson |
| 6,234,705 B1 | 5/2001 | Troxell | | 2003/0191532 A1 | 10/2003 | Goble |
| 6,261,296 B1 | 7/2001 | Aebi | | 2003/0204259 A1 | 10/2003 | Goble |
| 6,293,949 B1 | 9/2001 | Justis | | 2004/0006391 A1 | 1/2004 | Reiley |
| 6,306,136 B1 | 10/2001 | Baccelli | | 2004/0049272 A1 | 3/2004 | Reiley |
| 6,352,537 B1 | 3/2002 | Strnad | | 2004/0049273 A1 | 3/2004 | Reiley |
| 6,368,351 B1 | 4/2002 | Glenn | | 2004/0049274 A1 | 3/2004 | Reiley |
| 6,383,186 B1 | 5/2002 | Michelson | | 2004/0049275 A1 | 3/2004 | Reiley |
| 6,395,030 B1 | 5/2002 | Songer | | 2004/0049276 A1 | 3/2004 | Reiley |
| 6,398,783 B1 | 6/2002 | Michelson | | 2004/0049277 A1 | 3/2004 | Reiley |
| 6,402,756 B1 | 6/2002 | Ralph | | 2004/0049278 A1 | 3/2004 | Reiley |
| 6,419,703 B1 | 7/2002 | Fallin | | 2004/0049281 A1 | 3/2004 | Reiley |
| 6,428,542 B1 | 8/2002 | Michelson | | 2004/0059429 A1 | 3/2004 | Amin et al. |
| 6,436,101 B1 | 8/2002 | Hamada | | 2004/0087948 A1 | 5/2004 | Suddaby |
| 6,436,145 B1 | 8/2002 | Miller | | 2004/0111154 A1 | 6/2004 | Reiley |
| 6,454,771 B1 | 9/2002 | Michelson | | 2004/0116927 A1 | 6/2004 | Graf |
| 6,458,131 B1 | 10/2002 | Ray | | 2004/0122427 A1 | 6/2004 | Holmes |
| 6,461,359 B1 * | 10/2002 | Tribus et al. ................... 606/61 | | 2004/0127989 A1 | 7/2004 | Dooris |

| | | | |
|---|---|---|---|
| 2004/0143264 A1 | 7/2004 | McAfee | |
| 2004/0143268 A1 | 7/2004 | Falahee | |
| 2004/0181226 A1 | 9/2004 | Michelson | |
| 2004/0181229 A1 | 9/2004 | Michelson | |
| 2004/0186475 A1 | 9/2004 | Falahee | |
| 2004/0186476 A1 | 9/2004 | Michelson | |
| 2004/0210313 A1 | 10/2004 | Michelson | |
| 2004/0210314 A1 | 10/2004 | Michelson | |
| 2004/0215195 A1* | 10/2004 | Shipp et al. | 606/69 |
| 2004/0220678 A1 | 11/2004 | Chow | |
| 2004/0230201 A1 | 11/2004 | Yuan | |
| 2004/0230304 A1 | 11/2004 | Yuan | |
| 2004/0236334 A1 | 11/2004 | Michelson | |
| 2004/0236335 A1 | 11/2004 | Michelson | |
| 2005/0010291 A1 | 1/2005 | Stinson et al. | |
| 2005/0027297 A1 | 2/2005 | Michelson | |
| 2005/0027298 A1 | 2/2005 | Michelson | |
| 2005/0049705 A1 | 3/2005 | Hale et al. | |
| 2005/0159746 A1 | 7/2005 | Grob et al. | |
| 2005/0165484 A1* | 7/2005 | Ferree | 623/17.11 |
| 2005/0187551 A1* | 8/2005 | Orbay et al. | 606/69 |
| 2005/0228381 A1* | 10/2005 | Kirschman | 606/61 |
| 2005/0251138 A1* | 11/2005 | Boris et al. | 606/61 |
| 2006/0036243 A1* | 2/2006 | Sasso et al. | 606/61 |

FOREIGN PATENT DOCUMENTS

| | | |
|---|---|---|
| DE | 2821678 A1 | 4/1980 |
| DE | 3113142 A1 | 1/1982 |
| DE | 4012622 C1 | 7/1991 |
| DE | 9304368 U | 6/1993 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0307241 B1 | 12/1992 |
| EP | 0677277 A2 | 10/1995 |
| EP | 0767636 B1 | 4/1997 |
| EP | 1138268 A1 | 10/2001 |
| FR | 2623085 | 5/1989 |
| FR | WO 90/00037 | 1/1990 |
| FR | 2681525 A1 | 3/1993 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 A1 | 9/2001 |
| FR | 2806616 A1 | 9/2001 |
| GB | 780652 | 8/1957 |
| JP | 10-179622 | 7/1998 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 95/35067 | 12/1995 |
| WO | WO 96/08206 A1 | 3/1996 |
| WO | WO 96/39975 | 12/1996 |
| WO | WO 98/48717 | 11/1998 |
| WO | WO 98/55038 | 12/1998 |
| WO | WO 99/23963 A1 | 5/1999 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/53126 | 9/2000 |
| WO | WO 01/26566 A1 | 4/2001 |
| WO | WO 01/28442 A1 | 4/2001 |
| WO | WO 01/30248 A1 | 5/2001 |
| WO | WO 02/34120 A2 | 5/2002 |
| WO | WO 02/085226 A1 | 10/2002 |
| WO | WO 03/057055 A1 | 7/2003 |
| WO | WO 03/101350 A1 | 12/2003 |
| WO | WO 2004/071358 A1 | 8/2004 |
| WO | WO 2004/098465 A1 | 11/2004 |

OTHER PUBLICATIONS

Waldemar Link, brochure entitled *Wirbelsäulen-Chirurgie*: Instrumentarium Und Implantate Zur *Wirbelsäulen-Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, ©1990 Raven Press, Ltd., New York.

Richard W. Porter, MD, FRSC, FRCSE, *Spinal Stenosis and Neurogenic Claudication*, Spine vol. 21, No. 17, pp. 2046-2052, ©1996, Lippincott-Raven Publishers.

Kotani, Y., et al., "The effects of spinal fixation and destabilization on the biomechanical and histologic properties of spinal ligaments: An in vivo study," Spine, vol. 23, No. 6, Mar. 15, 1998, pp. 672-682.

Lemaire, J.P., et al., "Intervertebral disc prosthesis: results and prospects for the year 2000," Clinical Orthopaedics and Related Research, No. 337, 1997, pp. 64-76.

Lombardi, J.S., et al., "Treatment of Degenerative Spondylolisthesis," Spine, vol. 10, No. 9, 1985, pp. 821-827.

McMilllin, C.R. et al., "Artificial Spinal Discs with up to Five Years Follow-up," 20th Annual Meeting of the Society for Biomaterials (Abstract), Apr. 5-9, 1994, pp. 89.

Nagata, H., et al., "The effects of immobilization of long segments of the spine on the adjacent and distal facet force and lumbosacral motion," Spine, vol. 18, No. 16, 1993, pp. 2471-2479.

Posner, I., et al., "A Biomechanical Analysis of the Clinical Stability of the Lumbar and Lumbosacral Spine," Spine, vol. 7, No. 4, 1982, pp. 374-389.

Rosenberg, N.J., "Degenerative Spondylolisthesis—Predisposing Factors," The Journal of Bone and Joint Surgery, vol. 57-A, No. 4, 1975, pp. 467-474.

Szpalski, M., et al., "Spine Arthroplasty: A Historical Review," Eur Spine J., vol. 11, Suppl. 2, Aug. 13, 2002, pp. S65-S84.

Tsantrizos, A., et al., "Segmental stability and compressive strength of posterior lumbar interbody fusion implants," Spine, vol. 25, No. 15, 2000, pp. 1899-1907.

Dickson, R.A., "The etiology and pathogenesis of idiopathic scoliosis," Acta Orthopaedica Belgica, vol. 58, Suppl. 1, 1992, pp. 21-25.

Dickson, R.A., "The scientific basis of treatment of idiopathic thoracic scoliosis," Acta Orthopaedica Belgica, vol. 58, Suppl.1, 1992, pp. 107-110.

Millner, P.A., et al., " Idiopathic scoliosis: biomechanics and biology," Eur. Spine J., vol. 5, 1996, pp. 362-373.

Mohaideen, A., et al., "Not all rods are Harrington—an overview of spinal instrumentation in scoliosis treatment," Pediatr. Radiol. 30, 2000, pp. 110-118.

Smith, R.M., et al., "Experimental structural scoliosis," The Journal of Bone and Joint Surgery, vol. 69, 1987, pp. 576-581.

Chiu, J.C., et al., "Translaminar Facet Fixation: An Alternative Method for Lumbar Fusion: Report of 710 Cases," http://www.spinecenter.com/papers/facet/facet.htm, Sep. 8, 2005, 12 pages.

Van Schaik, Jan P.J., et al., "Curvature of the Lower Lumbar Facet Joints: Variations at Different Levels and Relationship with Orientation," Journal of Spinal Disorders, vol. 12, No. 4, 1999, pp. 341-347.

Lu, J., et al.,"Translaminar Facet Screw Placement: an Anatomic Study," The American Journal of Orthopedics, Aug. 1998, pp. 550-555.

Ebraheim, N. A., et al.,"The Quantitative Anatomy of the Thoracic Facet and the Posterior Projection of Its Inferior Facet," Spine, vol. 22, No. 16, 1997, pp. 1811-1818.

Panjabi, M.M., et al.,"Articular Facets of the Human Spine, Quantitative Three-Dimensional Anatomy," Spine, vol. 18, No. 10, 1993, pp. 1298-1310.

Boden, S.D., et al., "Orientation of the Lumbar Facet Joints: Association with Degenerative Disc Disease," The Journal Of Bone and Joint Surgery, vol. 78-A, No. 3, Mar. 1996, pp. 403-411.

Cavanaugh, J.M., et al., "Lumbar Facet Pain: Biomechanics Neuroanatomy and Neurophysiology," Survey Article, J. Biomechanics, vol. 29, No. 9, 1996, pp. 1117-1129.

Yoganandan, N., et al.,"Anatomic Study of the Morphology of Human Cervical Facet Joint," Spine, vol. 28, No. 20, 2003, pp. 2317-2323.

Dudley, et al., "Spinal Injuries," Rod & Smith's Operative Surgery—Orthopaedics Part 1, London: Butterworth-Heinemann, 1991, pp. 637-641.

* cited by examiner

INTER-CERVICAL FACET IMPLANT WITH LOCKING SCREW AND METHOD

CLAIM OF PRIORITY

This application claims priority to United States Provisional Application, entitled, INTER-CERVICAL FACET IMPLANT AND METHOD filed Dec. 13, 2004, Ser. No. 60/635,453, which is incorporated herein by reference.

CROSS-REFERENCE TO RELATED APPLICATIONS

This application is related to U.S. patent application Ser. No. 11/053,399, entitled INTER-CERVICAL FACET IMPLANT AND METHOD, filed Feb. 8, 2005; U.S. patent application Ser. No. 11/053,624, entitled INTER-CERVICAL FACET IMPLANT AND METHOD, filed Feb. 8, 2005; U.S. patent application Ser. No. 11/053,735, entitled INTER-CERVICAL FACET IMPLANT AND METHOD, filed Feb. 8, 2005; U.S. patent application Ser. No. 11/053,346, entitled INTER-CERVICAL FACET IMPLANT AND METHOD, filed Feb. 8, 2005; and U.S. patent application Ser. No. 11/093,689, entitled INTER-CERVICAL FACET IMPLANT AND METHOD FOR PRESERVING THE TISSUES SURROUNDING THE FACET JOINT, filed Mar. 30, 2005 each of which is incorporated herein in full, by reference.

TECHNICAL FIELD

This invention relates to interspinous process implants.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space*, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression, and neural injury. Id.; Yoo, J. U. et al., *Effect of cervical spine motion on the neuroforaminal dimensions of human cervical spine*, Spine, vol. 17 at 1131 (Nov. 10, 1992). In contrast, neck flexion increases the foraminal area. Humpreys, S. C. et al., supra, at 1105.

In particular, cervical radiculopathy secondary to disc herniation and cervical spondylotic foraminal stenosis typically affects patients in their fourth and fifth decade, and has an annual incidence rate of 83.2 per 100,000 people (based on 1994 information). Cervical radiculopathy is typically treated surgically with either an anterior cervical discectomy and fusion ("ACDF") or posterior laminoforaminotomy ("PLD"), with or without facetectomy. ACDF is the most commonly performed surgical procedure for cervical radiculopathy, as it has been shown to increase significantly the foraminal dimensions when compared to a PLF.

It is desirable to eliminate the need for major surgery for all individuals, and in particular, for the elderly. Accordingly, a need exists to develop spine implants that alleviate pain caused by spinal stenosis and other such conditions caused by damage to, or degeneration of, the cervical spine.

The present invention addresses this need with implants and methods for implanting an apparatus into at least one facet joint of the cervical spine to distract the cervical spine while preferably preserving mobility and normal lordotic curvature.

DETAILED DESCRIPTION

Embodiments of the present invention provide for a minimally invasive surgical implantation method and apparatus for cervical spine implants that preserves the physiology of the spine. In particular, embodiments provide for distracting the cervical spine to increase the foraminal dimension in extension and neutral positions. Such implants, when implanted in the cervical facet joints, distract, or increase the space between, the vertebrae to increase the foraminal area or dimension, and reduce pressure on the nerves and blood vessels of the cervical spine.

The facet joints in the spine are formed between two vertebrae as follows. Each vertebra has four posterior articulating surfaces: two superior facets and two inferior facets, with a superior facet from a lower vertebra and an inferior facet of an upper vertebra forming a facet joint on each lateral side of the spine. In the cervical spine, the upward inclination of the superior articular surfaces of the facet joints allows for considerable flexion and extension, as well as for lateral mobility. Each facet joint is covered by a dense, elastic articular capsule, which is attached just beyond the margins of the articular facets. The capsule is larger and looser in the cervical spine than in the thoracic and lumbar spine. The inside of the capsule is lined by a synovial membrane which secretes synovial fluid for lubricating the facet joint. The exterior of the joint capsule is surrounded by a capsular ligament. It is this ligament and the joint capsule that must be cut in the embodiments of the method described herein for inserting the artificial facet joint.

In a specific preferred embodiment, an implanted interfacet spacer of 1.5 mm to 2.5 mm in width can result in interfacet distraction that increases foraminal dimension in extension and neutral. Other interfacet spacer dimensions also are contemplated by the invention described herein below. The present embodiments also preserve mobility of the facet joints.

Further embodiments of the present invention accommodate the distinct anatomical structures of the spine, minimize further trauma to the spine, and obviate the need for invasive methods of surgical implantation. Embodiments of the present invention also address spinal conditions that are exacerbated by spinal extension.

Figure 1:
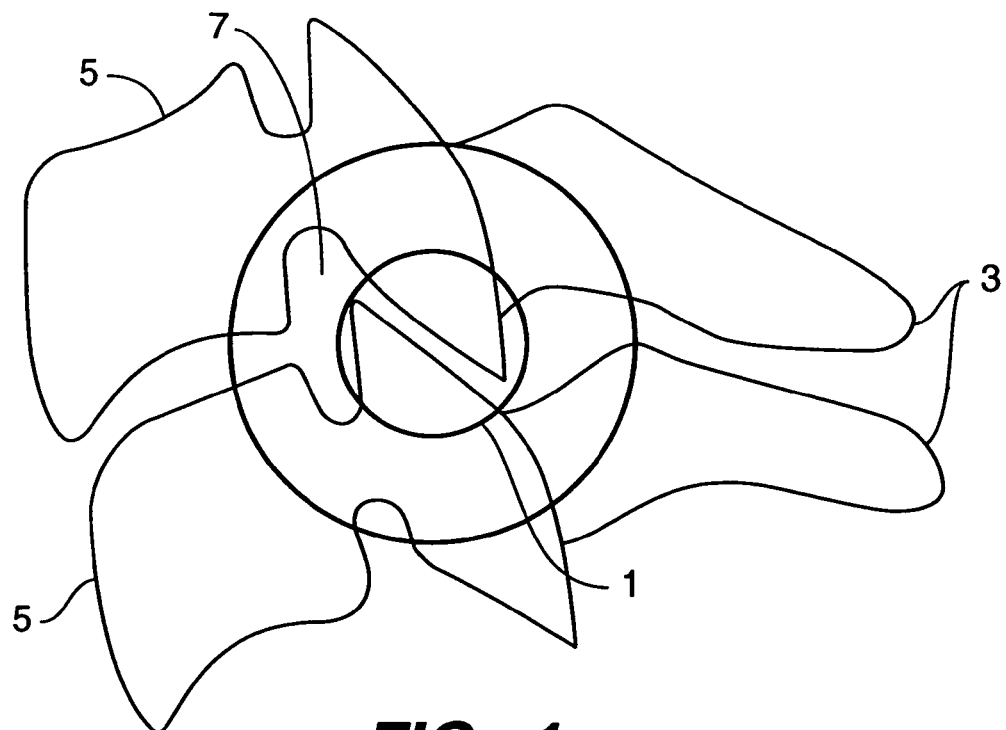
FIG. 1 shows a lateral view of two adjacent cervical vertebrae and spinous processes, highlighting the cervical facet joint.

FIG. 1 shows a simplified diagram of a portion of the cervical spine, focusing on a cervical facet joint 1 formed between two adjacent cervical vertebrae. The spinous processes 3 are located posteriorly and the vertebral bodies 5 are located anteriorly, and a nerve root canal 7 is visible. Each vertebra has four posterior articulating surfaces: two superior facets and two inferior facets, with a superior facet from a lower vertebra and an inferior facet of an upper vertebra forming a facet joint on each lateral side of the spine. In the cervical spine, the upward inclination of the superior articular surfaces of the facet joints allows for considerable flexion and extension, as well as for lateral mobility. Each facet joint is covered by a dense, elastic articular capsule, which is attached just beyond the margins of the articular facets. The capsule is large and looser in the cervical spine than in the thoracic and lumbar spine. The inside of the capsule is lined by a synovial membrane which secretes synovial fluid for lubricating the facet joint. The exterior of the joint capsule is surrounded by a capsular ligament. It is this ligament that may be pushed out of the way in the embodiments of the method for inserting the artificial facet joint, described herein.

Figure 2:
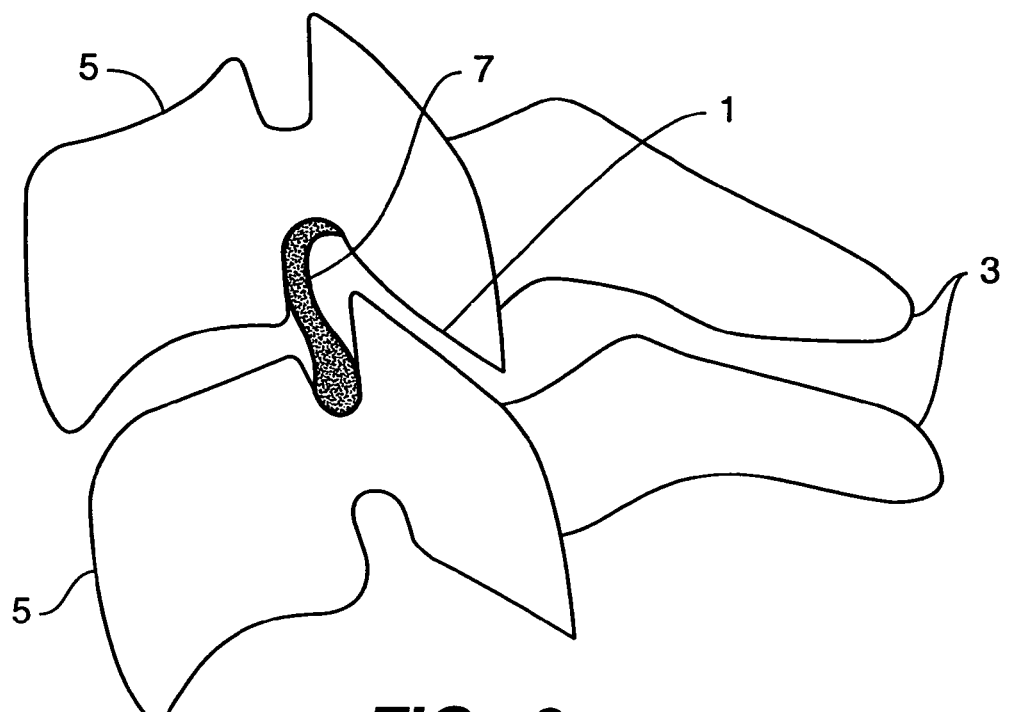
FIG. 2 depicts a lateral view of the cervical spine with spinal stenosis.

FIG. 2 depicts cervical foraminal stenosis. From the drawing, the nerve root canal 7 is narrowed relative to the nerve root canal 7 depicted in FIG. 1. The spinal canal and/or intervertebral foraminal also can be narrowed by stenosis. The narrowing can cause compression of the spinal cord and nerve roots.

Figure 3A:
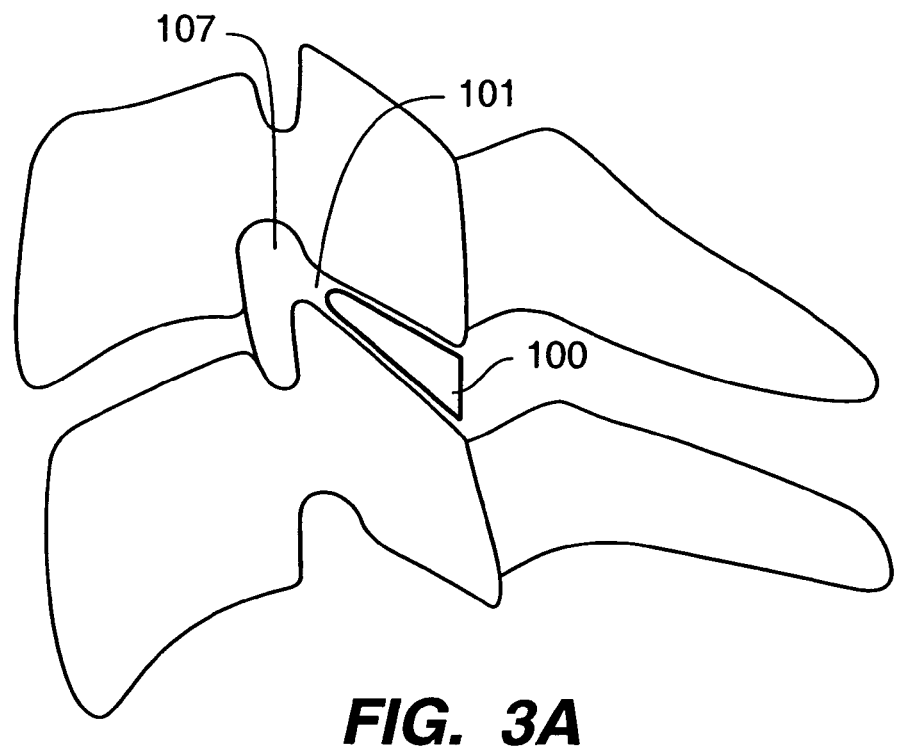
FIG. 3A depicts correction of cervical stenosis or other ailment with a wedge-shaped embodiment of the implant of the invention positioned in the cervical facet joint.
Figure 3B:
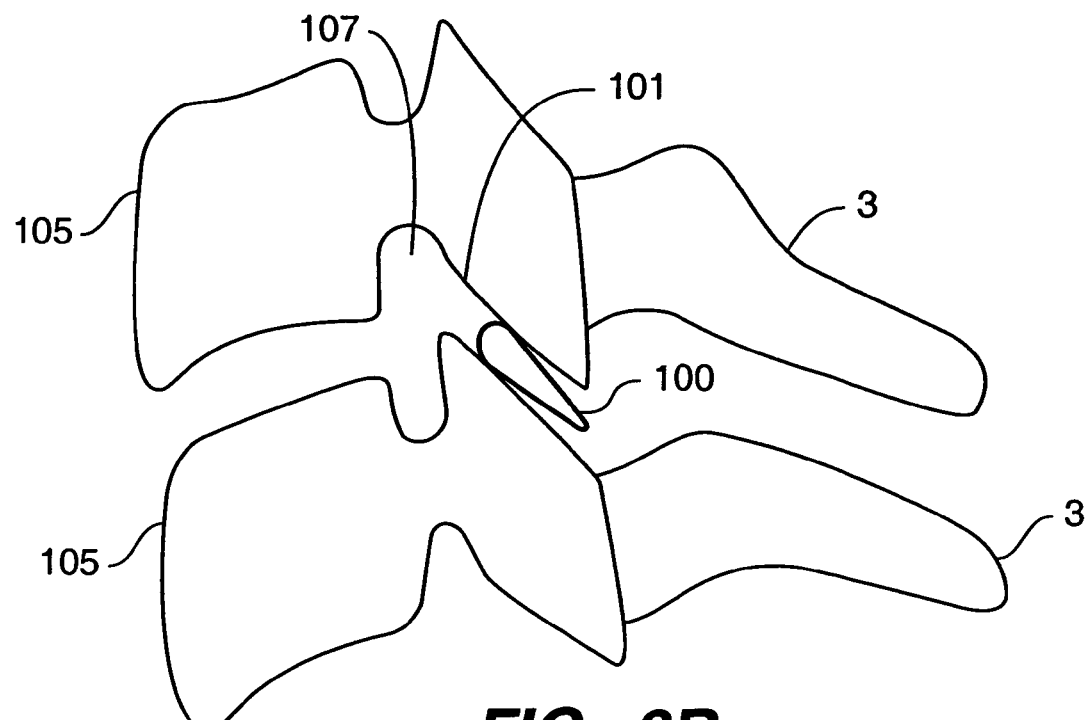
FIG. 3B depicts correction of cervical kyphosis or loss of lordosis with a wedge-shaped embodiment of the invention with the wedge positioned in the opposite direction as that depicted in FIG. 3A.

FIG. 3A shows a first embodiment 100 of the present invention, which is meant to distract at least one facet joint, in order to increase the dimension of the neural foramen while retaining facet joint mobility. The wedge-shaped embodiment or inter-facet spacer 100 is a wedge-shaped implant that can be positioned in the cervical facet joint 101 to distract the joint and reverse narrowing of the nerve root canal 107. In this embodiment or inter-facet spacer 100, the implant is positioned with the narrow portion of the wedge facing anteriorly. However, it is also within the scope of the present invention to position the embodiment or inter-facet spacer 100 (FIG. 3B) with the wide portion of the wedge facing anteriorly, to correct for cervical kyphosis or loss of cervical lordosis.

It is to be understood that implants in accordance with the present invention, and/or portions thereof can be fabricated from somewhat flexible and/or deflectable material. In these embodiments, the implant and/or portions thereof can be made out of a polymer, such as a thermoplastic. For example, in one embodiment, the implant can be made from polyketone, known as polyetheretherketone ("PEEK"). Still more specifically, the implant can be made from PEEK 450G, which is an unfilled PEEK approved for medical implantation available from Victrex of Lancashire, Great Britain. Other sources of this material include Gharda located in Panoli, India. PEEK has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

The material specified has appropriate physical and mechanical properties and is suitable for carrying and spreading a physical load between the adjacent spinous processes. The implant and/or portions thereof can be formed by extrusion, injection, compression molding and/or machining techniques.

In some embodiments, the implant can comprise, at least in part, titanium or stainless steel, or other suitable implant material which is radiopaque, and at least in part a radiolucent material that does not show up under x-ray or other type of imaging. The physician can have a less obstructed view of the spine under imaging, than with an implant comprising radiopaque materials entirely. However, the implant need not comprise any radiolucent materials.

It should be noted that the material selected also can be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that unfilled PEEK. The resulting product is known to be ideal for improved strength, stiffness, or stability. Carbon-filled PEEK is known to enhance the compressive strength and stiffness of PEEK and to decrease its expansion rate. Carbon-filled PEEK offers wear resistance and load-carrying capability.

In this embodiment or inter-facet spacer 100, the implant is manufactured from PEEK, available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer also can be comprised of polyetherketoneketone ("PEKK"). Other material that can be used include polyetherketone ("PEK"), polyetherketoneetherketoneketone ("PEKEKK"), and polyetheretherketoneketone ("PEEKK"), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials"; PCT Publication WO 02/00275 A1, dated Jan. 3, 2002, entitled "Bio-Compatible Polymeric Materials; and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Figure 4:
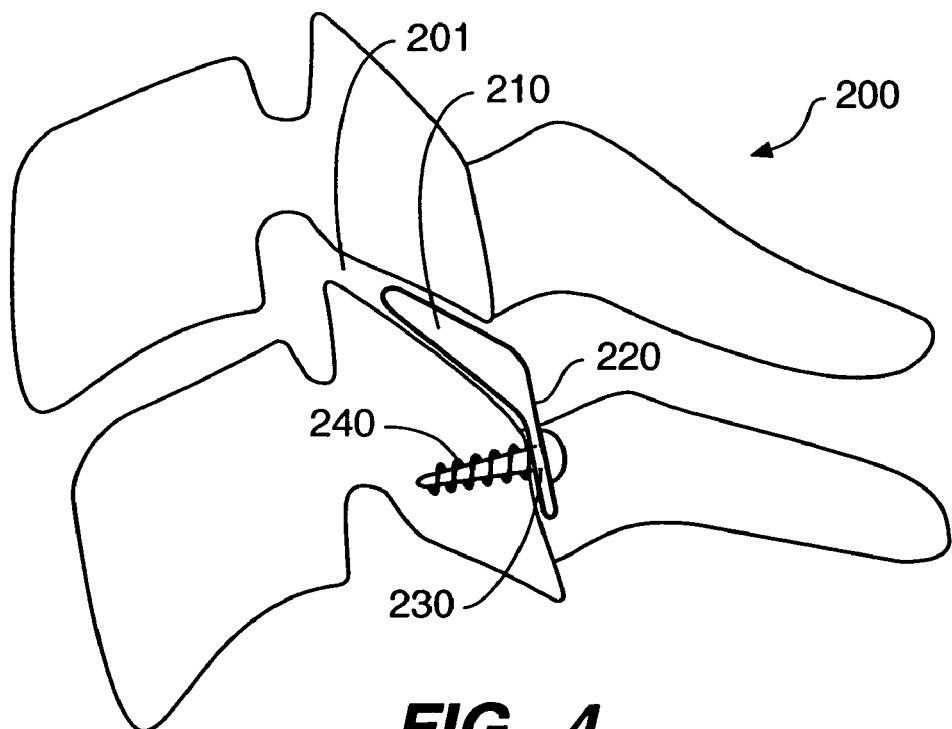
FIG. 4 shows correction of cervical stenosis or other ailment with a further embodiment of the implant of the invention including a screw fixation device for attaching to a single vertebra.

Turning now to FIG. 4, the embodiment 200 of the implant has a joint insert or inter-facet spacer 210, also herein referred to as an artificial facet joint spacer or inter-facet joint spacer, that is positioned in the cervical facet joint 101. The joint insert or inter-facet spacer 210 can be wedge-shaped with the narrow part of the wedge facing anteriorly. Alternatively, the joint insert or inter-facet spacer 210 need not be wedge-shaped but can be of substantially uniform thickness, the thickness determined by an individual patient's need for distraction of the cervical facet joint 201. As with embodiment 100, one objective of this embodiment is facet joint distraction, and joint mobility after implantation. The joint insert or inter-facet spacer 210 is continuous with a posterior sheath 220 bent at an angle from the joint insert or inter-facet spacer 210 to align substantially parallel with the bone. The posterior sheath can lie against the lamina, preferably against the lateral mass. The posterior sheath 220 can have a bore 230 which can accept a bone screw 240. Alternatively, the bore 230 can accept any other appropriate and/or equivalent fixation device capable of fixing the embodiment 200 to the spine. The device is thereby affixed to the vertebra, preferably by fixing to the lateral mass.

Figure 5:
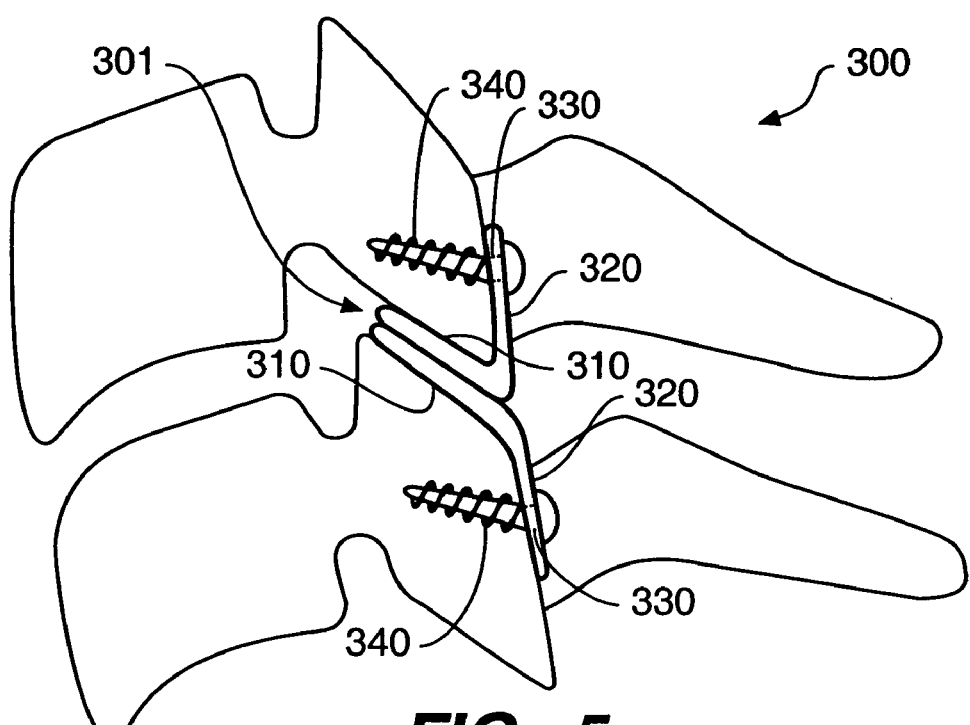
FIG. 5 shows correction of cervical stenosis or other ailment with a further embodiment of the implant of the invention, comprising screw fixation of two implants, one implant fixed to each of two adjacent vertebrae.

FIG. 5 shows embodiment 300, which is the use of two embodiments 200, each fixed to one of two adjacent cervical vertebrae. As with embodiment 200, the implanted facet joint is distracted and joint mobility is retained. A joint insert or inter-facet spacer 310 from each of the two implants is inserted and positioned in the cervical facet joint 301. In this embodiment, the joint inserts or inter-facet spacers 310 are substantially flat and parallel to each other and are not wedge-shaped. Alternatively, the joint inserts or inter-facet spacers 310 can together define a wedge-shaped insert that is appropriate for the patient. The two joint inserts or inter-facet spacers 310 combined can have, by way of example, the shape of the joint insert or inter-facet spacer 210 in FIG. 4. Embodiment 300 then can be fixed to the spine with a screw 340 or any other appropriate fixation device, inserted through a bore 330 in the posterior sheath 320. The posterior sheath 320 can be threaded to accept a screw. The screw can be embedded in the lamina, preferably in the lateral mass, where possible.

Figure 6:
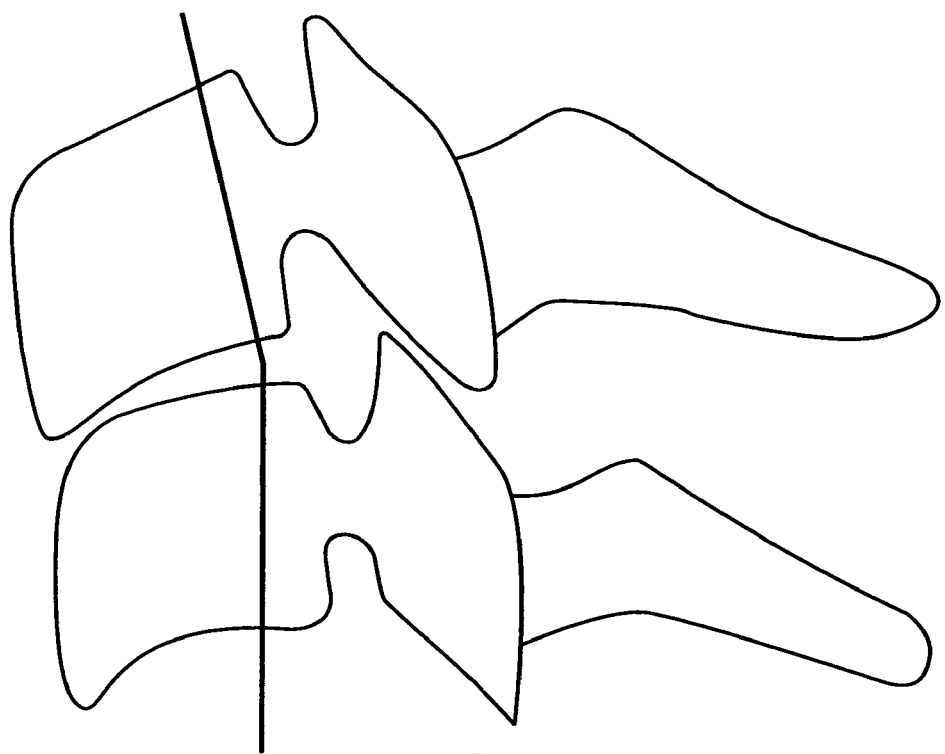
FIG. 6 shows cervical spine kyphosis, or loss of lordosis.
Figure 7:
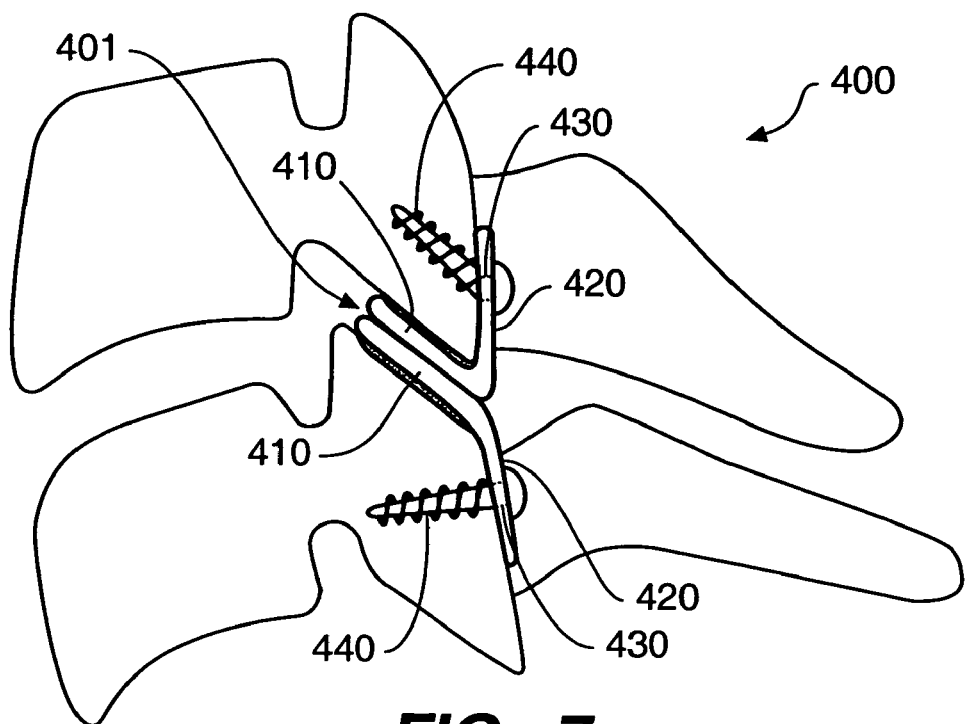
FIG. 7 shows correction of cervical kyphosis, or loss of lordosis, with a further embodiment of the implant of the invention comprising two facet implants with screw fixation.

It is within the scope of the present invention to use and/or modify the implants of the invention to correct cervical spine kyphosis, or loss of lordosis. FIG. 6 depicts a cervical spine lordosis. FIG. 7 demonstrates an embodiment 400 which contemplates positioning two implants to correct for this spinal abnormality while retaining facet joint mobility. The joint insert or inter-facet spacer 410 of each implant is shaped so that it is thicker at its anterior portion. Alternatively, the implants can be shaped to be thicker at the posterior ends, for example as depicted in FIG. 3A. The posterior sheath 420 of each implant is bent at an angle from the joint insert or inter-facet spacer 410 to be positioned adjacent to the lateral mass and/or lamina, and has a bore 430 to accept a screw 440 or other appropriate and/or equivalent fixation means to fix the embodiment 400 to the spine, preferably to the lateral mass. The placement of two joint inserts or inter-facet spacers 410 in the cervical facet joint 401 distracts the facet joint, which shifts and maintains the vertebrae into a more anatomical position to preserve the physiology of the spine.

Figure 8:
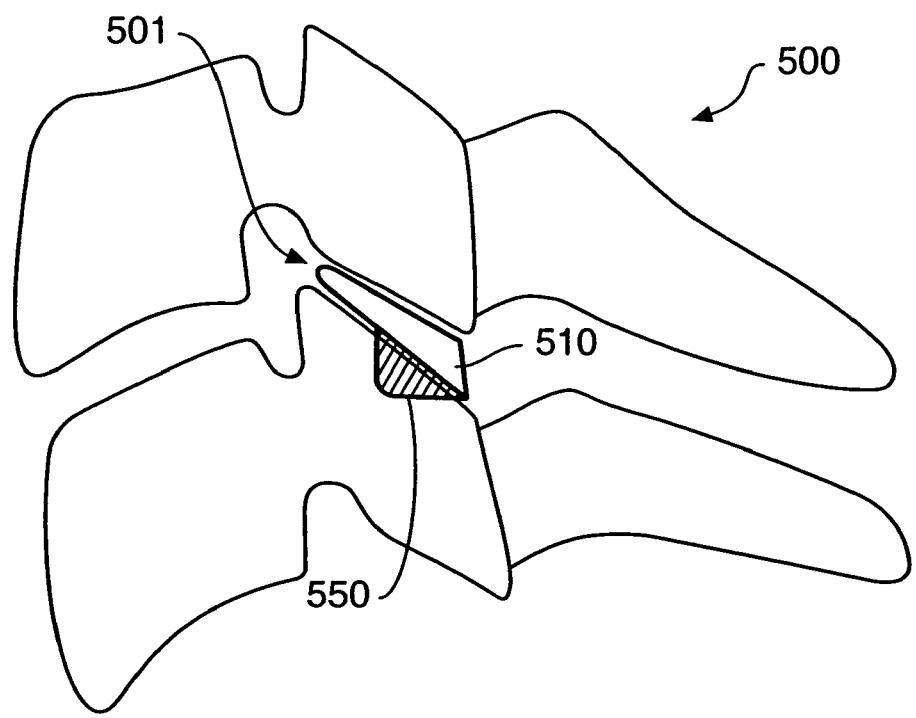
FIG. 8 shows correction of cervical stenosis or other ailment with a further embodiment of the implant of the invention, comprising a facet implant and a keel.

FIG. 8 shows a further embodiment 500 of the implant of the invention, wherein the joint insert or inter-facet spacer 510 has a keel 550 on an underside of the joint insert or inter-facet spacer 510. The keel 550 can be made of the same material or materials set forth above. The surfaces of the keel 550 can be roughened in order to promote bone ingrowth to stabilize and fix the implant 500. In other embodiments, the keel 550 can be coated with materials that promote bone growth such as, for example, bone morphogenic protein ("BMP"), or structural materials such as hyaluronic acid "HA," or other substances which promote growth of bone relative to and into the keel 550.

The keel 550 can be embedded in the facet bone, to facilitate implant retention. The keel 550 can be placed into a channel in the facet bone. The channel can be pre-cut. Teeth (not shown), preferably positioned posteriorly, also may be formed on the keel 550 for facilitating retention of the implant 500 in the cervical facet joint 501. As noted above, the joint insert or inter-facet spacer 510 can be substantially flat or wedge-shaped, depending upon the type of distraction needed, i.e., whether distraction is also necessary to correct abnormal curvature or lack of curvature in the cervical spine. Because the joint is not fused, mobility is retained, as with the embodiments described above and herein below.

Figure 9:
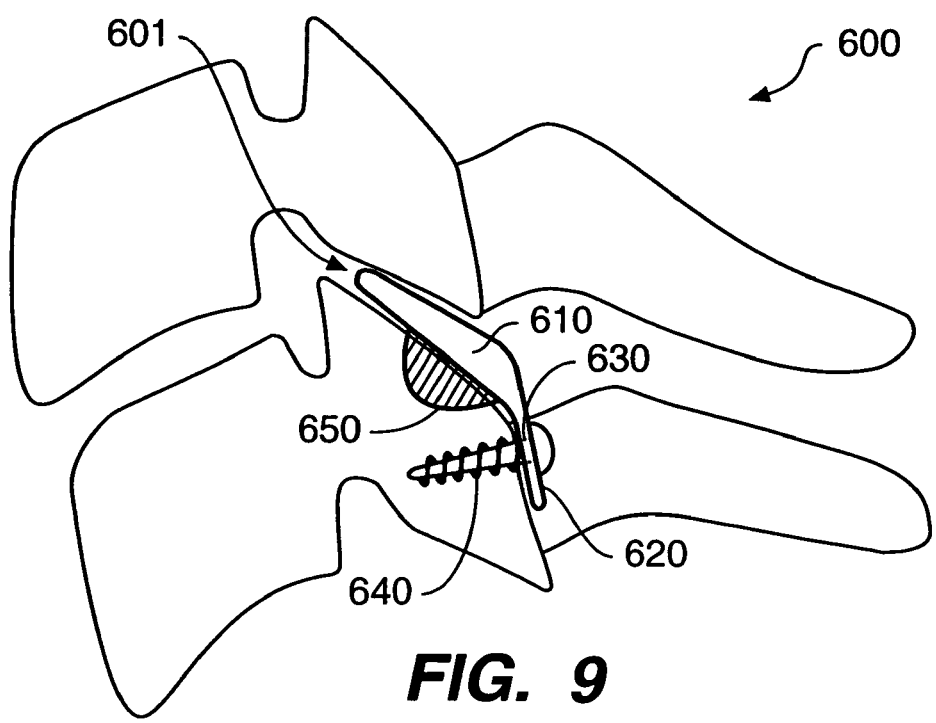
FIG. 9 shows correction of cervical stenosis or other ailment with a further embodiment of the implant of the invention, comprising facet implant, a keel, and screw fixation.

FIG. 9 illustrates that a further embodiment 600 of the implant of the invention can have both screw fixation and a keel 650 for stability and retention of the implant 600. On embodiment 600, the joint insert or inter-facet spacer 610 is continuous with a posterior sheath 620 having a bore hole 630 to accept a screw 640 which passes through the bore 630 and into the bone of the vertebrae, preferably into the lateral mass, or the lamina. The bore 630 can be threaded or not threaded where it is to accept a threaded screw or equivalent device. Alternatively, the bore 630 need not be threaded to accept a non-threaded equivalent device. The keel 650 is connected with the joint insert or inter-facet spacer 610 and embeds in the bone of the cervical facet joint 601 to promote implant retention.

Figure 10:
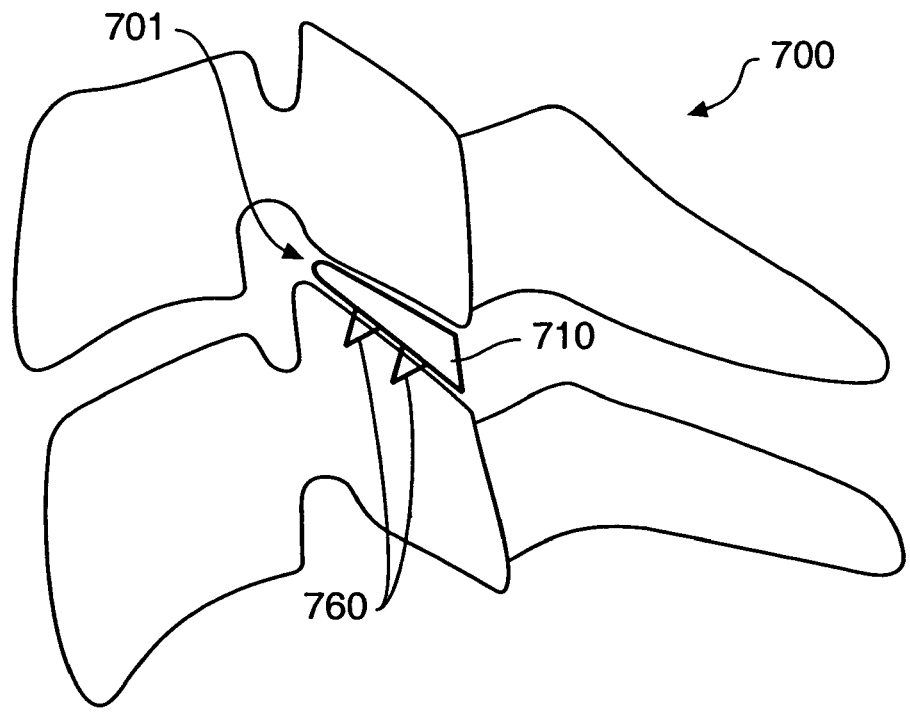
FIG. 10 shows correction of cervical stenosis or other ailment with a further embodiment of the implant of the invention, comprising a facet implant with teeth.

A further alternative embodiment 700 is illustrated in FIG. 10. In this embodiment 700, the joint insert or inter-facet spacer 710 has on a lower side at least one tooth 760. It should be clear to one of ordinary skill in the art that a plurality of teeth 760 is preferable. The teeth 760 are able to embed in the bone of the cervical facet joint 701 to facilitate retention of the implant 700 in the joint 701. The teeth 760 can face in a direction substantially opposite the direction of insertion, for retention of the implant 700. As above, the joint insert or inter-facet spacer 710 can be wedge-shaped or substantially even in thickness, depending upon the desired distraction. Because the implant distracts and is retained without fusion, facet joint mobility is retained.

Figure 11:
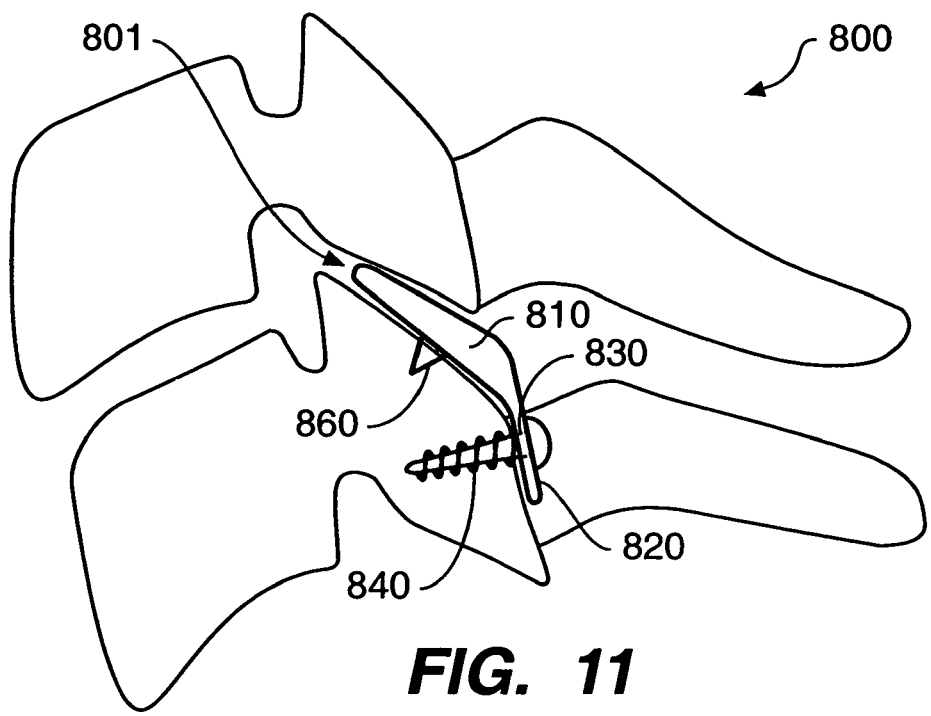
FIG. 11 depicts correction of cervical stenosis or other ailment with a further embodiment of the implant of the invention, comprising a facet implant with teeth and screw fixation.

FIG. 11 depicts a further embodiment 800 of the implant of the invention. In this embodiment 800, the joint insert or inter-facet spacer 810 is continuous with a posterior sheath 820 having a bore 830 for accepting a fixation device 840, as described above. The fixation device 840 can be a screw which fits into a threaded bore 830; alternatively, the fixation device 830 can be any other compatible and appropriate device. This embodiment 800 further combines at least one tooth 860 on an underside of the joint insert or inter-facet spacer 810 with the posterior sheath 820, bore 830 and fixation device 840 to address fixation of the implant 800 in a cervical facet joint 801. It will be recognized by one of ordinary skill in the art that the implant 800 can have a plurality of teeth 860 on the underside of the joint insert or inter-facet spacer 810.

Figure 12:
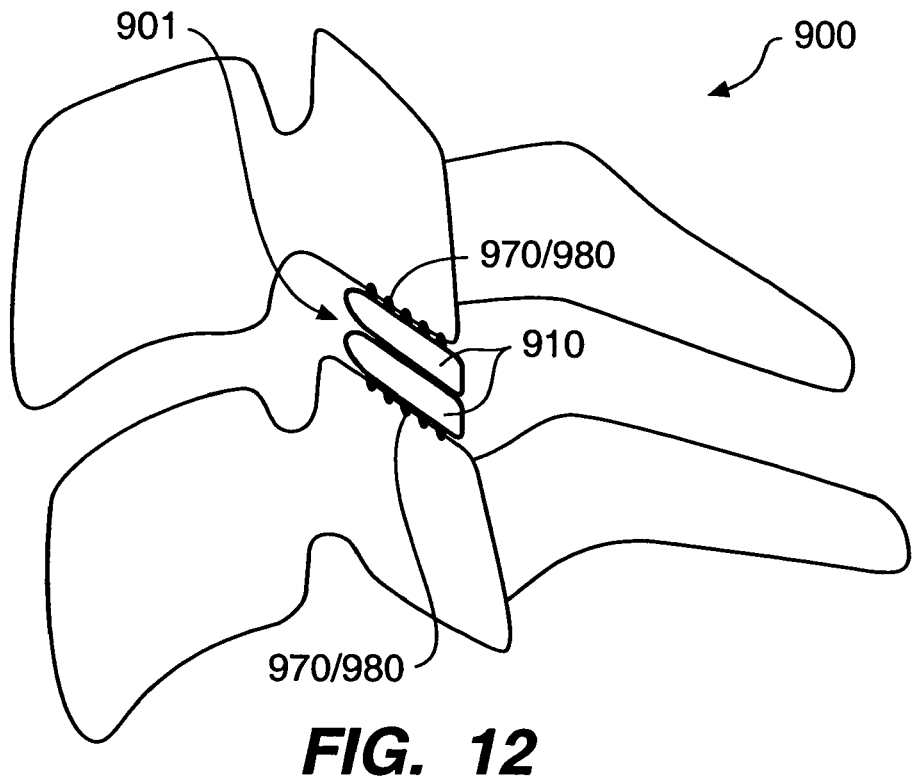
FIG. 12 depicts correction of cervical stenosis or other ailment with a further embodiment of the implant of the invention, comprising two facet implants having bony ingrowth surfaces.

FIG. 12 shows yet another embodiment 900 of an implant of the present invention. In this embodiment 900, the joint inserts or inter-facet spacers 910 of two implants 900 are positioned in a cervical facet joint or inter-facet spacer 901. As described above, the joint inserts or inter-facet spacers 910 can be wedge-shaped as needed to restore anatomical curvature of the cervical spine and to distract, or the joint inserts or inter-facet spacers 910 can be of substantially uniform thickness. The implants 900 each comprise a joint insert or inter-facet spacer 910 with an outer surface 970 that interacts with the bone of the cervical facet joint 901. On the upper implant 900, the surface 970 that interacts with the bone is the upper surface 970 and on the lower implant 900, the surface 970 that interacts with the bone is the lower surface 970. Each surface 970 can comprise a bone ingrowth surface 980 to create a porous surface and thereby promote bone ingrowth and fixation. One such treatment can be with plasma spray titanium, and another, with a coating of sintered beads. Alternatively, the implant 900 can have casted porous surfaces 970, where the porous surface is integral to the implant 900. As a further alternative, the surfaces 970 can be roughened in order to promote bone ingrowth into these defined surfaces of the implants 900. In other embodiments, the surfaces 970 can be coated with materials that promote bone growth such as, for example, bone morphogenic protein ("BMP"), or structural materials such as hyaluronic acid ("HA"), or other substances which promote growth of bone on other external surfaces 970 of the implant 900. These measures facilitate fixation of the implants 900 in the facet joint, but do not result in fusion of the joint, thereby retaining facet joint mobility, while also accomplishing distraction of the joint.

Figure 13:
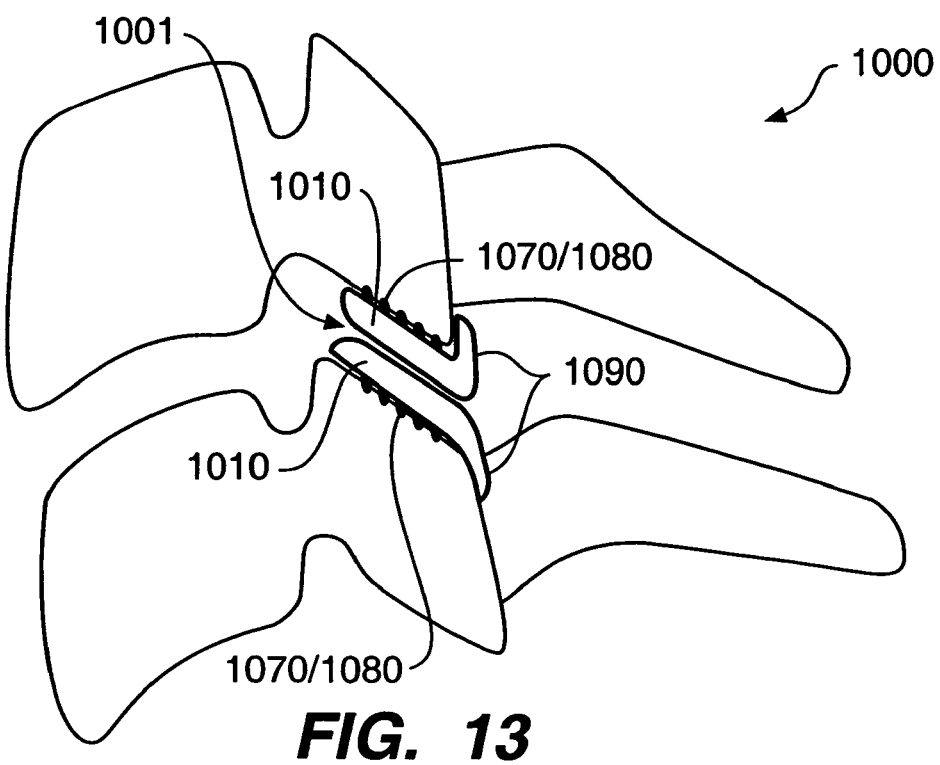
FIG. 13 depicts correction of cervical stenosis or other ailment with a further embodiment of the implant of the invention, comprising two facet implants having bony ingrowth surfaces and posterior alignment guide.

FIG. 13 depicts yet another embodiment 1000 of the implant of the present invention. In this embodiment 1000, the joint inserts or inter-facet spacers 1010 of two implants 1000 are positioned in a cervical facet joint 1001. As described above, the joint inserts or inter-facet spacers 1010 can be wedge-shaped as needed to restore anatomical curvature of the cervical spine and to distract, or the joint inserts or inter-facet spacers 1010 can be of substantially uniform thickness. The implants 1000 each comprise a joint insert or inter-facet spacer 1010 with an outer surface 1070 that interacts with the bone of the cervical facet joint 1001. On the upper implant 1000, the surface 1070 that interacts with the bone is the upper surface and on the lower implant 1000, the surface 1070 that interacts with the bone is the lower surface. As set forth above, each outer surface 1070 can comprise a bone ingrowth surface 1080 to create a porous surface and thereby promote bone ingrowth and fixation, without facet joint fusion and loss of mobility. In one preferred embodiment, the bone ingrowth surface 1080 can be created with plasma spray titanium, and/or with a coating of sintered beads. In an alternative preferred embodiment, the implant 1000 can have casted porous surfaces 1070, where the porous surface is integral to the implant 1000. In a further alternative preferred embodiment, the surfaces 1070 can be roughened in order to promote bone ingrowth into these defined surfaces of the implants 1000. In other preferred embodiments, the surfaces 1070 can be coated with materials that promote bone growth such as for example BMP, or structural materials such as HA, or other substances which promote growth of bone on other external surfaces 1070 of the implant 1000.

The implant 1000 can have a posterior alignment guide 1090. The posterior alignment guides 1090 of each implant 1000 can be continuous with the joint inserts or inter-facet spacers 1010. The posterior alignment guides substantially conform to the bone of the vertebrae when the joint inserts or inter-facet spacers 1010 are inserted into the cervical facet joint 1001. The posterior alignment guides 1090 are used to align the implants 1000 so that the joint inserts or inter-facet spacers 1010 contact each other and not the bones of the cervical facet joint 1001 when the joint inserts or inter-facet spacers 1010 are positioned in the cervical facet joint 1001.

Figure 14:
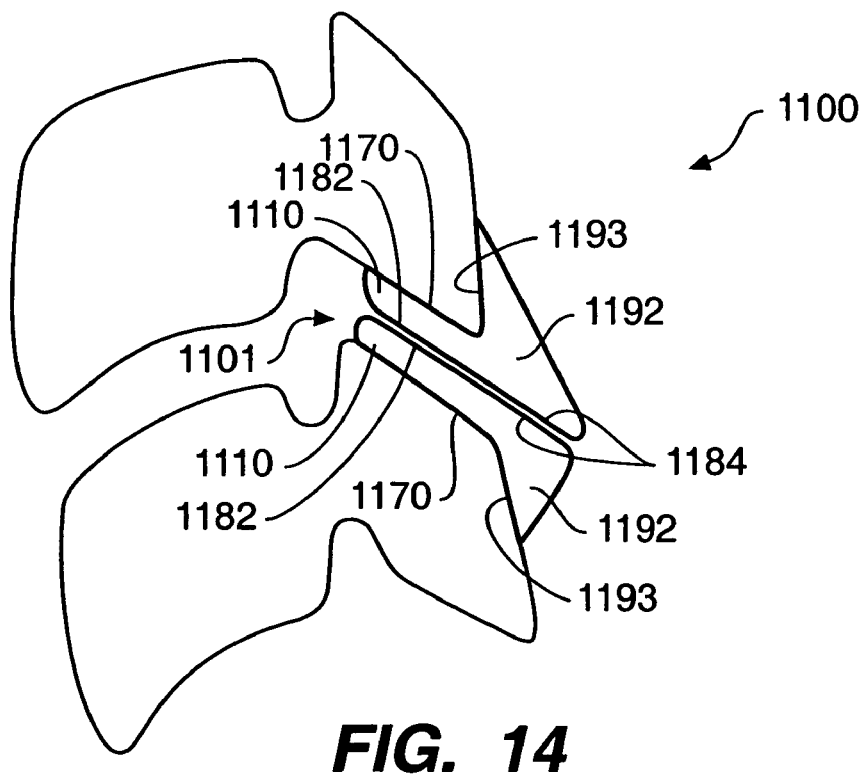
FIG. 14 shows correction of cervical stenosis or other ailment with a further embodiment of the implant of the invention, comprising two facet implants with increased facet joint contact surfaces.

FIG. 14 depicts a further embodiment 1100 of the implant of the present invention. In this embodiment 1100, the joint inserts or inter-facet spacers 1110 of two implants 1100 are inserted into the cervical facet joint 1101. Each of the joint inserts or inter-facet spacers 1110 is continuous with a cervical facet joint extender or facet-extending surface 1192. The bone contacting surfaces 1170 of the joint inserts or inter-facet spacers 1110 are continuous with, and at an angle to, the bone contacting surfaces 1193 of the cervical facet joint extenders 1192, so that the cervical facet joint extenders 1192 conform to the bones of the vertebrae exterior to the cervical facet joint 1101. The conformity of the cervical facet joint extenders 1192 is achieved, for example, by forming the cervical facet joint extenders 1192 so that when the joint inserts or inter-facet spacers 1110 are positioned, the cervical facet joint extenders 1192 curve around the bone outsider the cervical facet joint 1101.

The cervical facet joint extenders have a second surface 1184 that is continuous with the joint articular surfaces 1182 of the joint inserts or inter-facet spacers 1110. The second surfaces 1184 extend the implant 1100 posteriorly to expand the joint articular surfaces 1182 and thereby to increase contact and stability of the spine at least in the region of the implants 1100. It is to be understood that such facet joint extenders 1192 can be added to the other embodiments of the invention described and depicted herein.

Figure 15:
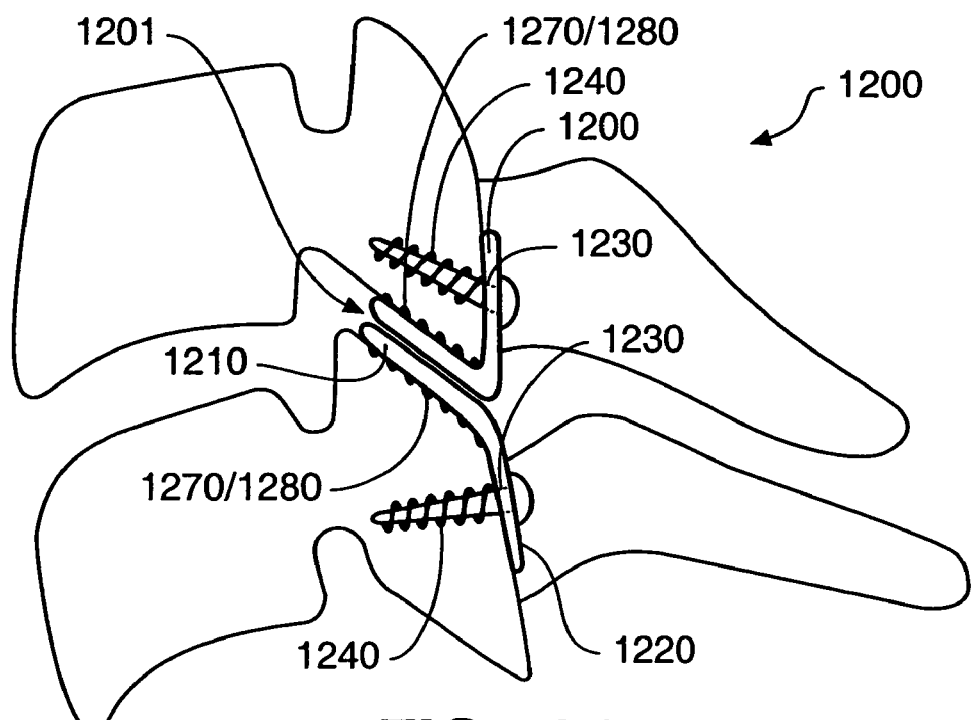
FIG. 15 shows correction of cervical stenosis or other ailment with a further embodiment of the implant of the invention, comprising two facet implants having bony ingrowth surfaces and screw fixation.

The embodiment depicted in FIG. 15 shows two implants 1200 positioned in a cervical facet joint 1201, having bony ingrowth surfaces as one preferred method of fixation, and using screws as another preferred method of fixation. In this embodiment, each of two implants 1200 has a joint insert or inter-facet spacer 1210 positioned in a cervical facet joint 1201. As described above, the joint inserts or inter-facet spacers 1210 can be wedge-shaped as needed to restore anatomical curvature of the cervical spine and to distract, or the joint inserts or inter-facet spacers 1210 can be of substantially uniform thickness. The implants 1200 each comprise a joint insert or inter-facet spacer 1210 with an outer surface 1270 that interacts with the bone of the cervical facet joint 1001. On the upper implant 1200, the surface 1270 that interacts with the bone is the upper surface and on the lower implant 1200, the surface 1270 that interacts with the bone is the lower surface. As set forth above, each outer surface 1270 can comprise a bone ingrowth surface 1280 to create a porous surface and thereby promote bone ingrowth and fixation. In one preferred embodiment, the bone ingrowth surface 1280 can be created with plasma spray titanium, and/or with a coating of sintered beads. In an alternative preferred embodiment, the implant 1200 can have casted porous surfaces 1270, where the porous surface is integral to the implant 1200. In a further alternative embodiment, the surfaces 1270 can be roughened in order to promote bone ingrowth into these defined surfaces of the implants 1200. In other preferred embodiments, the surfaces 1270 can be coated with materials that promote bone growth such as for example BMP, or structural materials such as HA, or other substances which promote growth of bone on other external surfaces 1270 of the implant 1200.

Screw fixation or other appropriate fixation also can be used with implants 1200 for fixation in the cervical facet joint 1201. The joint insert or inter-facet spacer 1210 is continuous with a posterior sheath 1220 bent at an angle from the joint insert or inter-facet spacer 1210 to align substantially parallel with the bone, preferably the lateral mass or lamina. The posterior sheath 1220 can have a bore 1230 which can accept a bone screw 1240, preferably into the lateral mass or lamina. Alternatively, the bore 1230 can accept any other appropriate and/or equivalent fixation means for fixing the embodiment 1200 to the spine.

Figure 16:
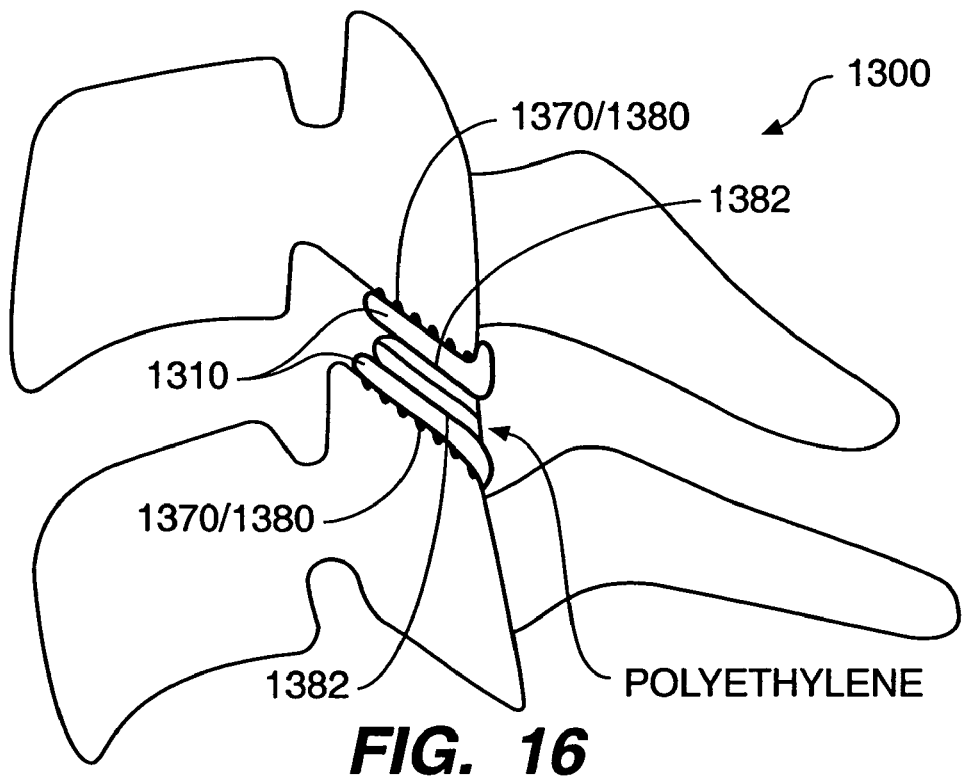
FIG. 16 shows correction of cervical stenosis or other ailment with a further embodiment of the implant of the invention, comprising two facet implants with articular inner surfaces.

FIG. 16 depicts a further preferred embodiment of the present invention. In this embodiment 1300, two joint inserts or inter-facet spacers 1310 are positioned in the cervical facet joint 1301. The joint inserts or inter-facet spacers each have outer surfaces 1370 that interact with the bone of the vertebrae forming the cervical facet joint. These outer surfaces 1370 of the embodiment 1300 can be treated to become bone ingrowth surfaces 1380, which bone ingrowth surfaces 1380 contribute to stabilizing the two joint inserts or inter-facet spacers 1310 of the implant 1300. In one preferred embodiment, the bone ingrowth surface 1380 can be created with plasma spray titanium, and/or with a coating of sintered beads. In an alternative preferred embodiment, the implant 1300 can have casted porous surfaces 1370, where the porous surface is integral to the implant 1300. In a further alternative embodiment, the surfaces 1370 can be roughened in order to promote bone ingrowth into these defined surfaces of the implants 1300. In other preferred embodiments, the surfaces 1370 can be coated with materials that promote bone growth such as, for example, BMP, or structural materials such as HA, or other substances which promote growth of bone on other external surfaces 1370 of the implant 1300. This fixation stabilizes the implant 1300 in the facet joint without fusing the joint, and, thus, the implant preserves joint mobility, while accomplishing distraction and increasing foraminal dimension.

Also shown in FIG. 16 are articular inner surfaces 1382 of the implants 1300. These surfaces can be formed from a metal and polyethylene, the material allowing flexibility and providing for forward bending/flexion and backward extension of the cervical spine. The embodiment 1300 of FIG. 16 can be made in at least two configurations. The first configuration includes a flexible spacer 1382 made, by way of example, using polyethylene or other suitable, flexible implant material. The flexible spacer 1382 can be permanently affixed to the upper and lower joint insert or inter-facet spacer 1310. The spacer 1382 can be flat or wedge-shaped or have any other shape that would correct the curvature of the spine. In other configurations, the spacer 1382 can be affixed to only the upper insert or inter-facet spacer 1310 or to only the lower insert or inter-facet spacer 1310. Alternatively, a spacer 1382 can be affixed to each of an upper insert or inter-facet spacer 1310 and a lower insert or inter-facet spacer 1310 with the upper insert or inter-facet spacer 1310 and the lower insert or inter-facet spacer 1310 being separate units.

Figure 17:
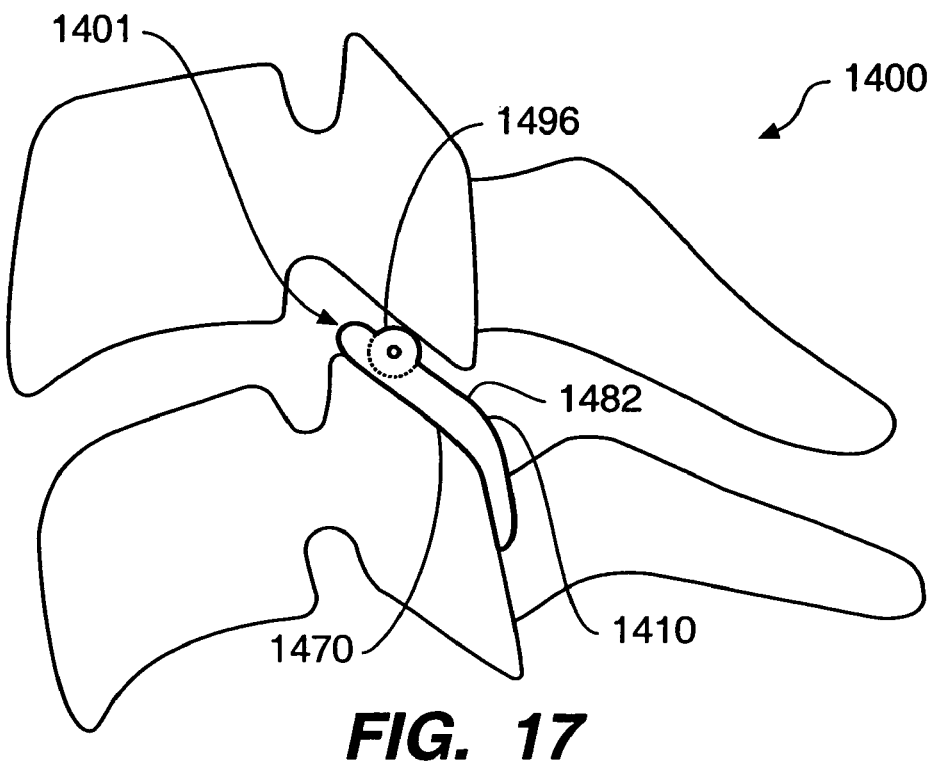
FIG. 17 shows correction of cervical stenosis or other ailment with a further embodiment of the implant of the invention, comprising a facet joint implant with a roller.
Figure 18:
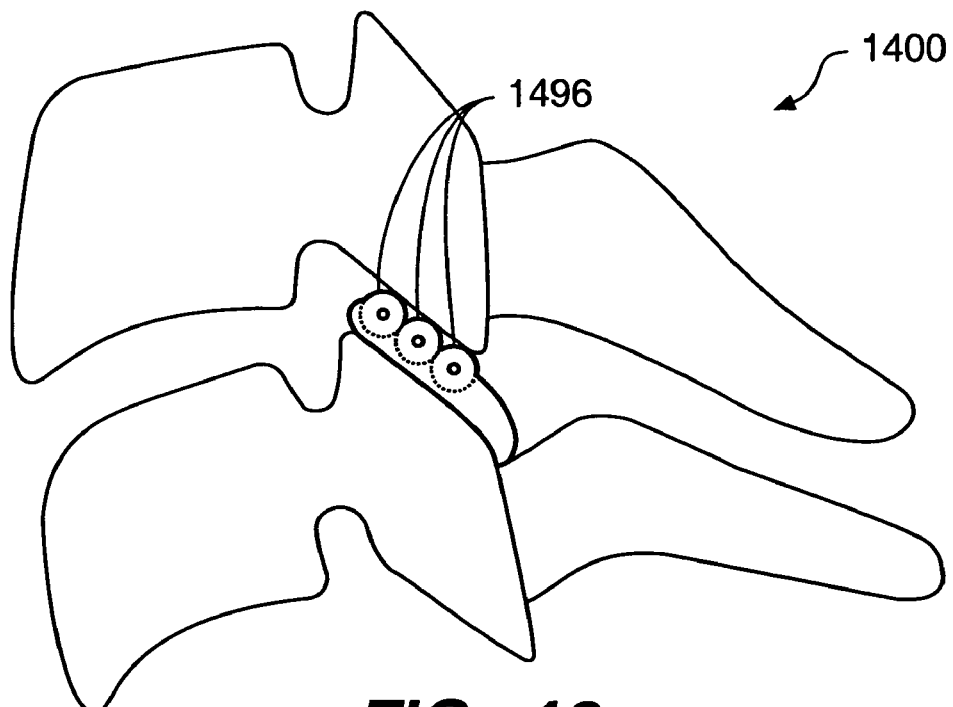
FIG. 18 shows correction of cervical stenosis or other ailment with a further embodiment of the implant of the invention, comprising a facet joint implant with a plurality of rollers.

FIG. 17 shows a further preferred embodiment of the implant of the present invention. In this embodiment 1400, the implant has a roller 1496 mounted on a joint insert or inter-facet spacer 1410, the roller being a further means of preserving joint mobility while accomplishing distraction. Both the roller 1496 and the joint insert or inter-facet spacer 1410 are positioned in the cervical facet joint 1401. The joint insert or inter-facet spacer 1410 as in other embodiments has a bone-facing surface 1470 and joint articular surface 1482. The bone-facing surface 1470 can interact with the lower bone of the cervical facet joint 1401. Alternatively, the bone-facing surface can interact with the upper bone of the cervical facet joint 1401. Between the bone-facing surface 1470 and the joint articular surface 1482 is an axis about which the roller 1496 can rotate. The roller 1496 rotates in a cavity in the joint insert or inter-facet spacer 1410, and interacts with the top bone of the cervical facet joint 1401. Alternatively, where the bone-facing surface 1470 of the joint insert or inter-facet spacer 1410 interacts with the top bone of the cervical facet joint 1401, the roller 1496 rotates in a cavity in the joint insert or inter-facet spacer 1410 and interacts with the lower bone of the cervical facet joint 1401. The rotation of the roller 1496 allows flexion and extension of the cervical spine. Alternatively, a roller such as roller 1496 can be secured to an upper and a lower insert such as inserts or spacers 410 in FIG. 7. As depicted in FIG. 18, a plurality of rollers 1496 also is possible.

Figure 19:
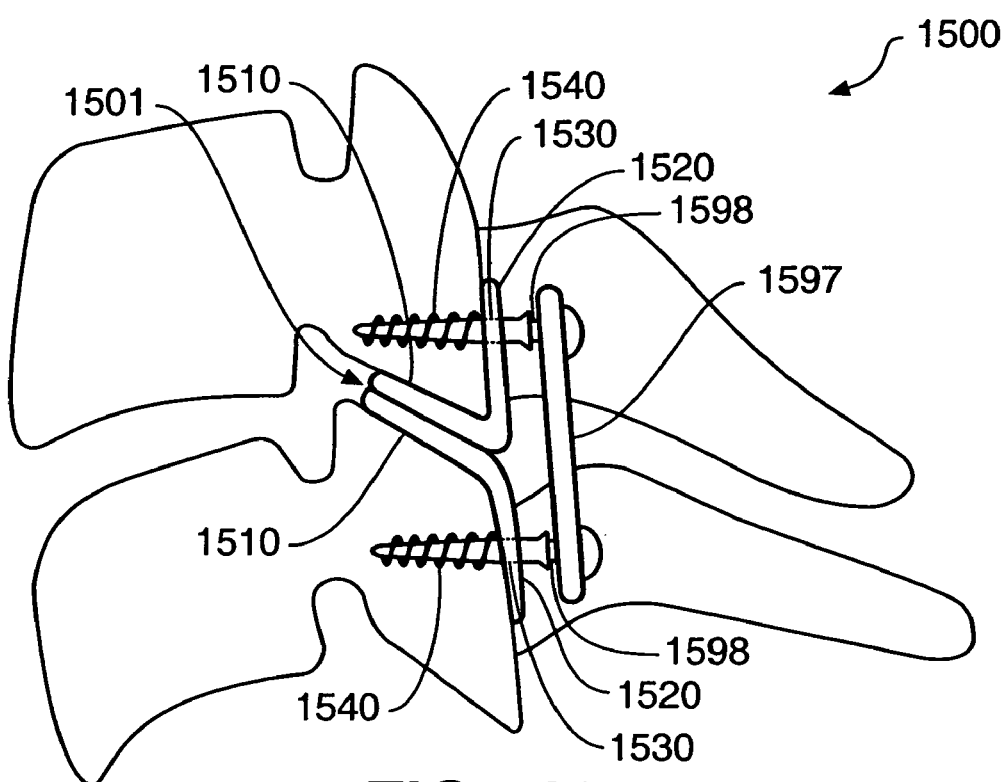
FIG. 19 shows correction of cervical stenosis or other ailment with a further embodiment of the implant of the invention, comprising two facet joint implants, screw fixation, and elastic restraint.

FIG. 19 depicts a further embodiment of the implant of the present invention. In this embodiment, two implants 1500 are implanted in the cervical facet joint 1501. Screw fixation or other appropriate fixation is used with implants 1500 for fixation in the cervical facet joint 1501. The joint insert or inter-facet spacer 1510 is continuous with a posterior sheath 1520 bent at an angle from the joint insert or inter-facet spacer 1510 to align substantially parallel with the bone, preferably the lateral mass or lamina. The posterior sheath 1520 of each implant 1500 can have a bore 1530 which can accept a bone screw 1540, preferably into the lateral mass or lamina. Alternatively, the bore 1530 can accept any other appropriate and/or equivalent fixation means for fixing the embodiment 1500 to the spine. The head of the screw 1540 in each posterior sheath 1520 of each implant 1500 has a groove 1598 or other mechanism for retaining an elastic band 1597. The elastic band 1597 is looped around each of the two screws 1540 to restrain movement of the cervical spine without eliminating facet joint mobility. The band 1597 preferably can restrain flexion and lateral movement. The elastic band 1597 can be made of a biocompatible, flexible material.

Figure 20:
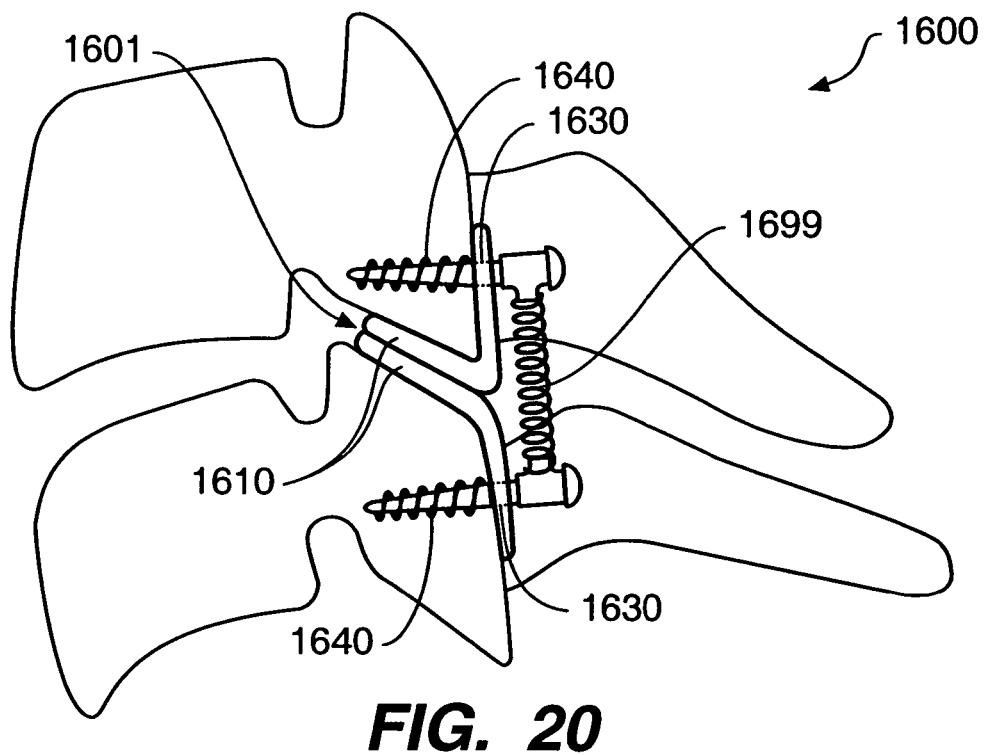
FIG. 20 shows correction of cervical stenosis or other ailment with a further embodiment of the implant of the invention, comprising two facet joint implants, screw fixation, and spring restraint.

FIG. 20 shows an alternative use of an elastic band as in FIG. 19. In the embodiment in FIG. 20, the elastic band is replaced with a spring restraint 1699, which extends between the heads of two screws 1640, one screw fixing each of the two implants 1600 in the cervical facet joint 1601.

Figure 21:
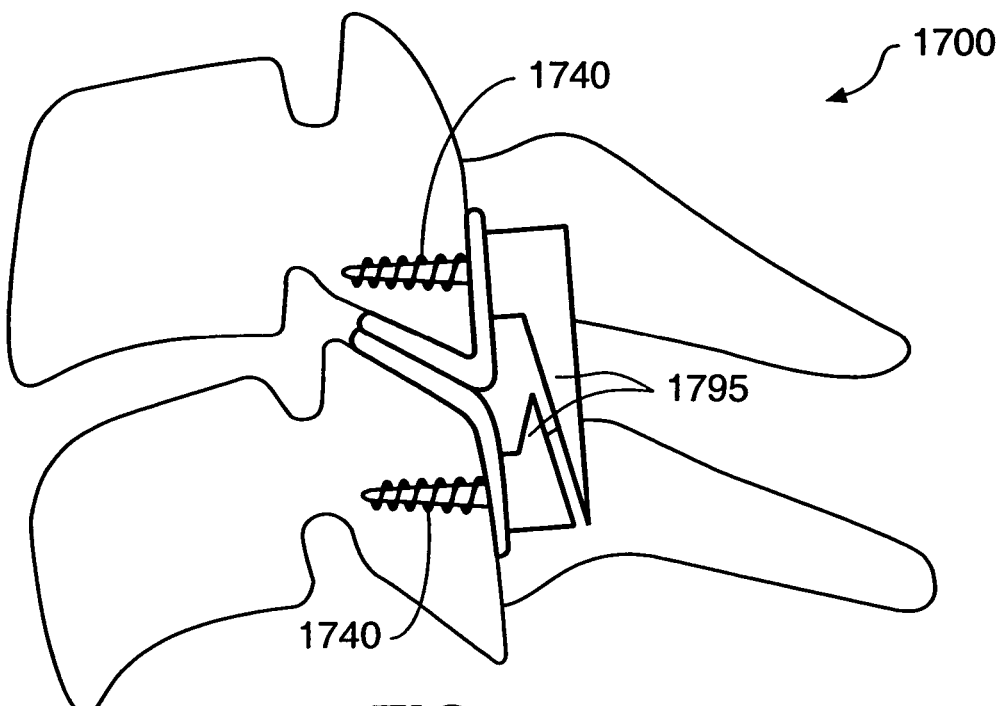
FIG. 21 shows correction of cervical stenosis or other ailment with a further embodiment of the implant of the invention, comprising two facet joint implants, screw fixation, and magnetic restraint.
Figure 22A:
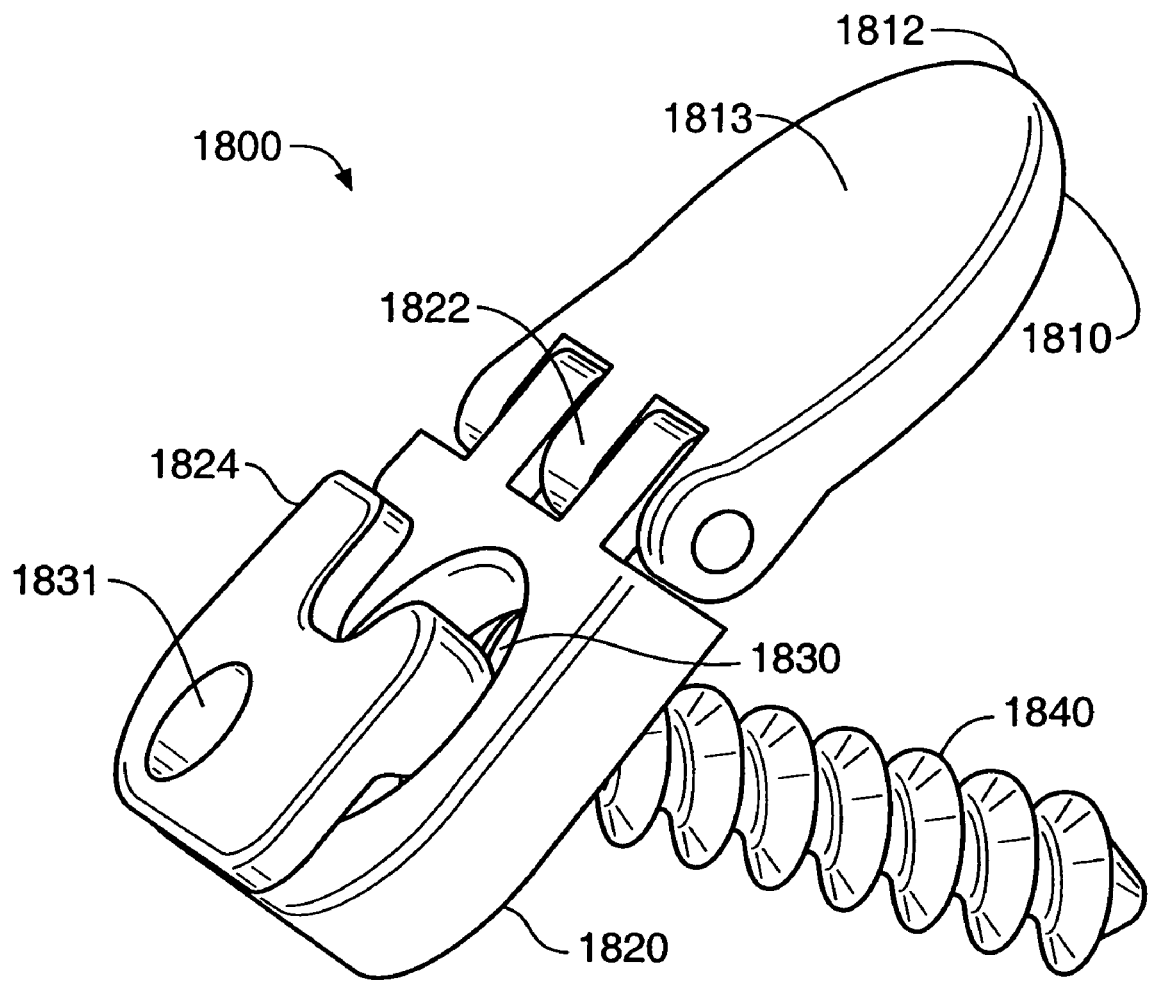
FIG. 22A shows a perspective view of a further embodiment of implant of the invention.
Figure 22B:
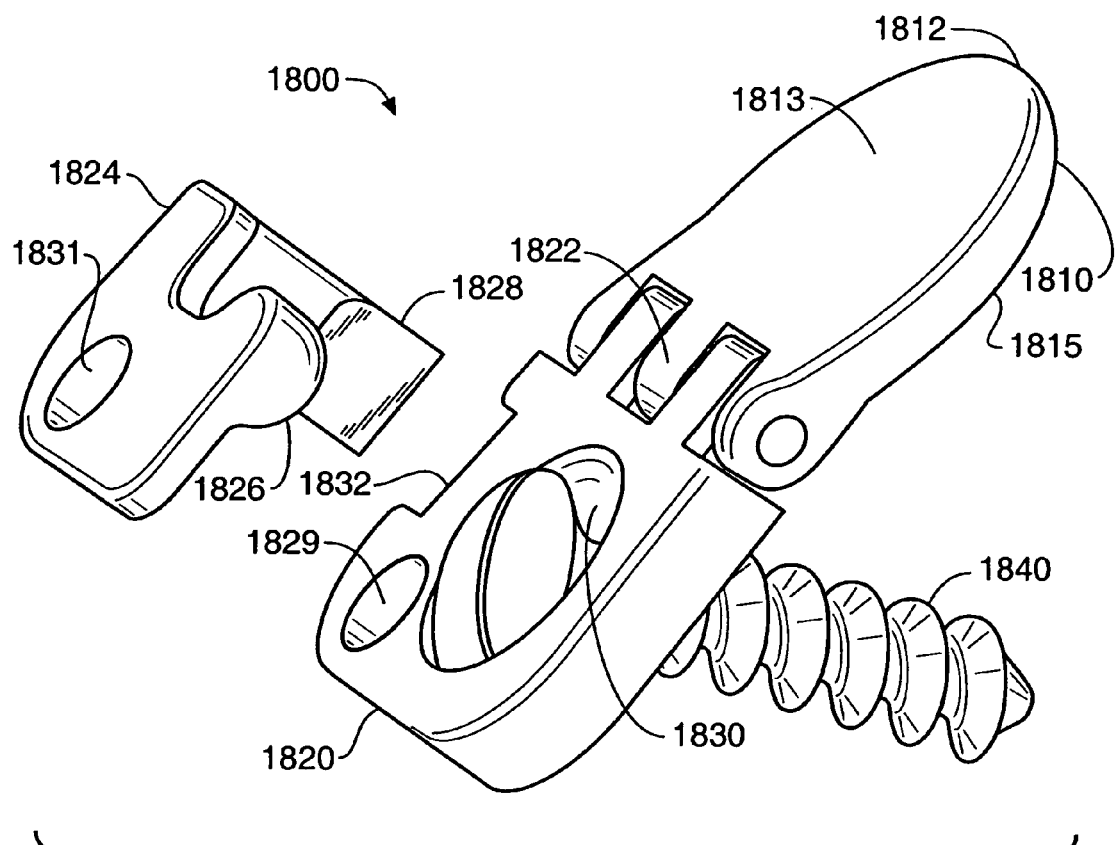
FIG. 22B shows a perspective exploded view of the embodiment of the invention shown in FIG. 22A.
Figure 23A:
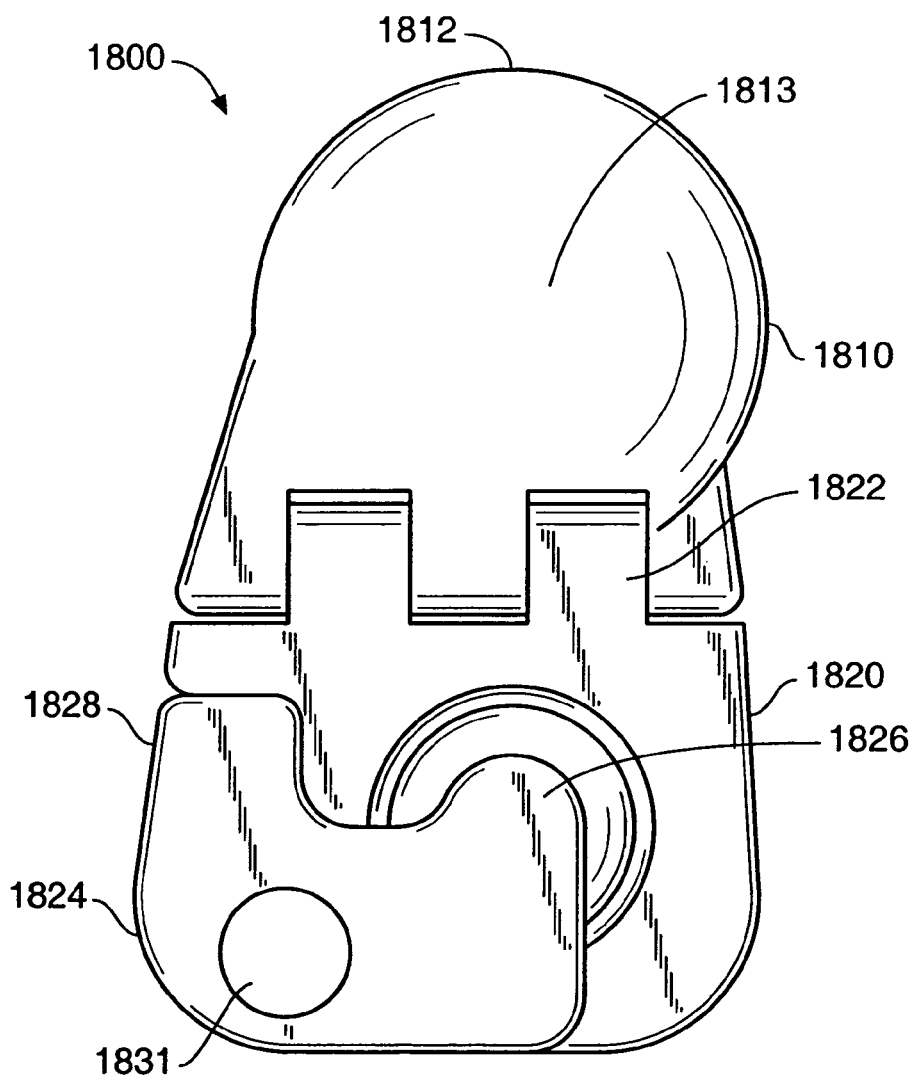
FIG. 23A depicts a posterior view of the embodiment of the implant of the invention shown in FIG. 22A.
Figure 23B:
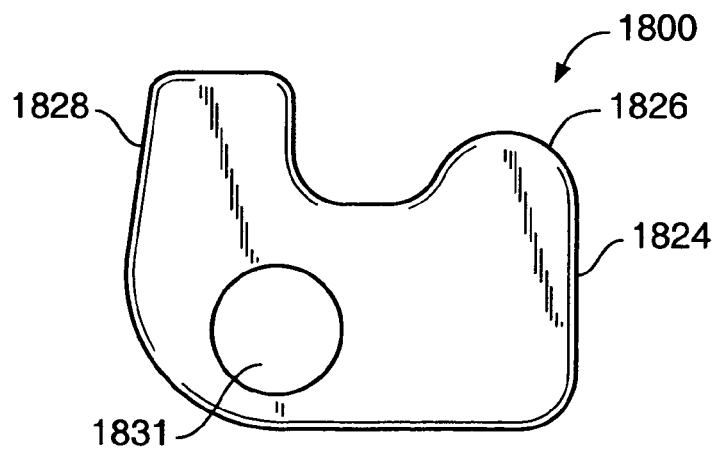
FIG. 23B shows a posterior view of a locking plate of the embodiment of the implant of the invention shown in FIG. 22A.
Figure 24A:
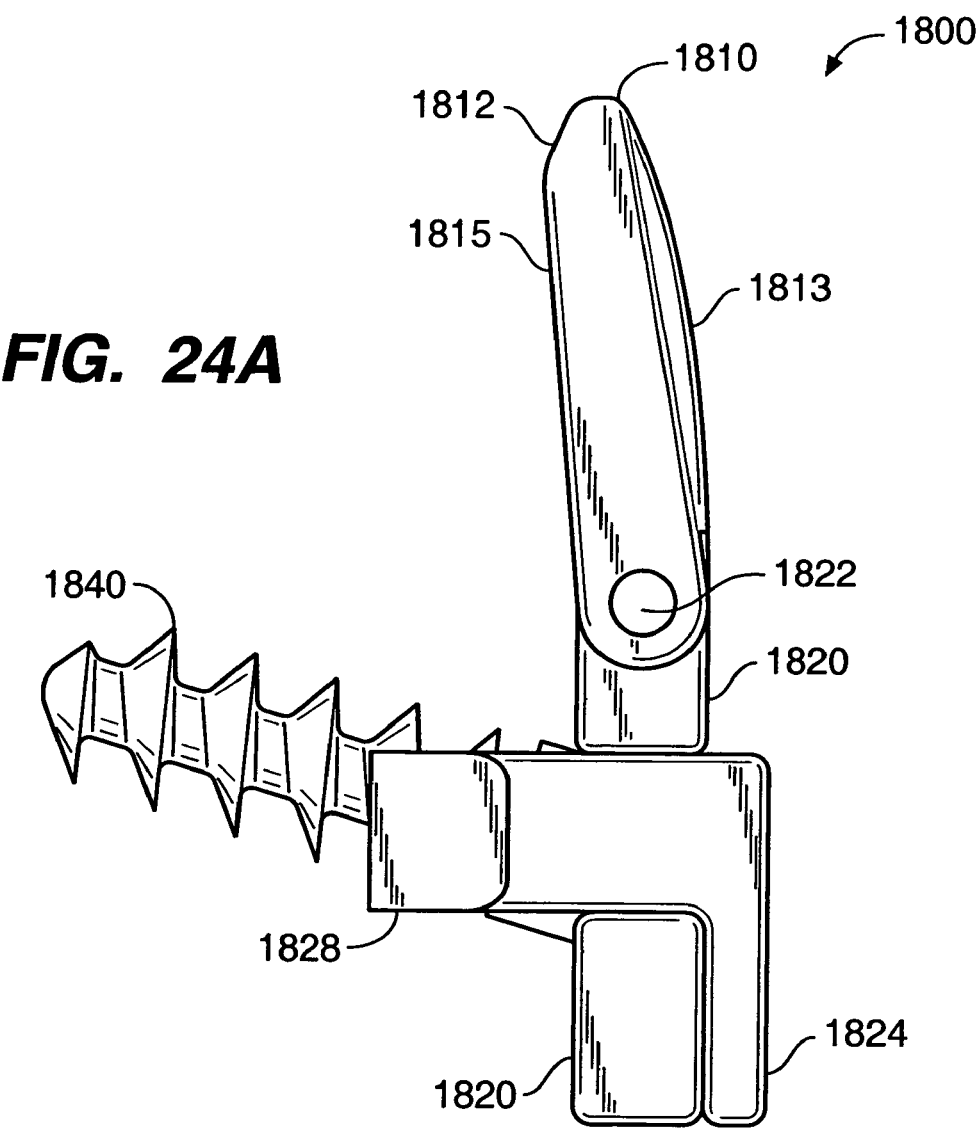
FIG. 24A depicts a lateral side view of the embodiment of the implant of the invention shown in FIG. 22A.
Figure 24B:
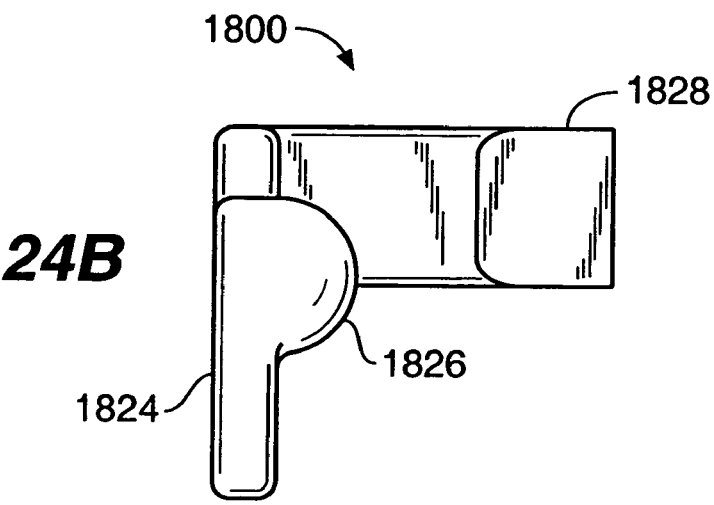
FIG. 24B shows a lateral side view of the keel of the locking plate of the embodiment of the implant of the invention shown in FIG. 22A.

FIG. 21 shows another alternative to using an elastic band and/or a spring as in FIG. 19 or 20. In FIG. 21, magnets 1795 are used for restraint between the two screws 1740. The magnet 1795 can either be comprised of two opposing magnetic fields or two of the same magnetic fields to restrain movement. The head of one of the two screws 1740 is magnetized, and the head of the other screw 1740 is magnetized with either the same or opposite field. If the magnets 1795 have the same polarity, the magnets 1795 repel each other and thus limit extension. If the magnets 1795 have opposite polarities, the magnets 1795 attract each other and thus limit flexion and lateral movement.

FIGS. 22A-24B, depict a further embodiment 1800 of the implant of the present invention. In this embodiment, an artificial facet joint spacer (or insert) or inter-facet spacer (or insert) 1810 is connected with a lateral mass plate (also referred to as an anchoring plate) 1820 with a hinge 1822. The hinge 1822 allows the lateral mass plate 1820 to bend at a wide range of angles relative to the artificial facet joint or inter-facet spacer and preferably at an angle of more than 90 degrees, and this flexibility facilitates positioning and insertion of the artificial facet joint or inter-facet spacer 1810 into a patient's facet joint, the anatomy of which can be highly variable among individuals. This characteristic also applies to embodiments described below, which have a hinge or which are otherwise enabled to bend by some equivalent structure or material property. The hinge 1822 further facilitates customizing the anchoring of the implant, i.e., the positioning of a fixation device. The hinge enables positioning of the lateral mass plate 1820 to conform to a patient's cervical spinal anatomy, and the lateral mass plate 1820 accepts a fixation device to penetrate the bone. The artificial facet joint or inter-facet spacer 1810 can be curved or rounded at a distal end 1812 (FIG. 23A), and convex or dome-shaped on a superior surface 1813 to approximate the shape of the bone inside the facet joint. The inferior surface 1815 can be flat or planar. Alternatively, the inferior surface 1815 can be concave. As another alternative, the inferior surface 1815 can be convex.

The lateral mass plate 1820, when implanted in the spine, is positioned outside the facet joint, preferably against the lateral mass or against the lamina. The lateral mass plate 1820 has a bore 1830 therethrough. The bore 1830 can accept a bone screw 1840, also referred to as a lateral mass screw, to secure the lateral mass plate 1820 preferably to the lateral mass or alternatively to another part of the spine, and thus to anchor the implant. The lateral mass screw 1840 preferably has a hexagonal head to accept an appropriately-shaped wrench. As described below, the head accepts a compatible probe 1826 from a locking plate 1824.

The locking plate 1824 includes a keel 1828 with a wedge shaped distal end to anchor the implant, preferably in the lateral mass or in the lamina, outside the facet joint and to prevent rotation of the lateral mass plate 1820 and the locking plate 1824. The keel 1828 aligns with a groove 1823 through an edge of the lateral mass plate 1820 to guide and align the keel 1828 as the keel 1828 cuts into a vertebra.

As noted above, the locking plate 1824 includes a probe 1826 that fits against the head of the lateral mass screw 1840.

The locking plate further includes a bore 1831 that can accept a machine screw (not shown) which passes through to an aligned bore 1829 in the lateral mass plate 1820 to hold the locking plate 1824 and the lateral mass plate 1820 together without rotational displacement relative to each other. The locking plate 1824 thus serves at least two functions: (1) maintaining the position of the lateral mass screw 1840 with the probe 1826, so that the screw 1840 does not back out; and (2) preventing rotation of the implant with the keel 1828 and machine screw relative to the cervical vertebra or other vertebrae.

It is to be understood that other mechanisms can be used to lock the locking plate 1824 to the lateral mass plate 1820. For example, the locking plate can include a probe with barbs that can be inserted into a port in the lateral mass plate. The barbs can become engaged in ribs that define the side walls of the port in the lateral mass plate.

Figure 25A:
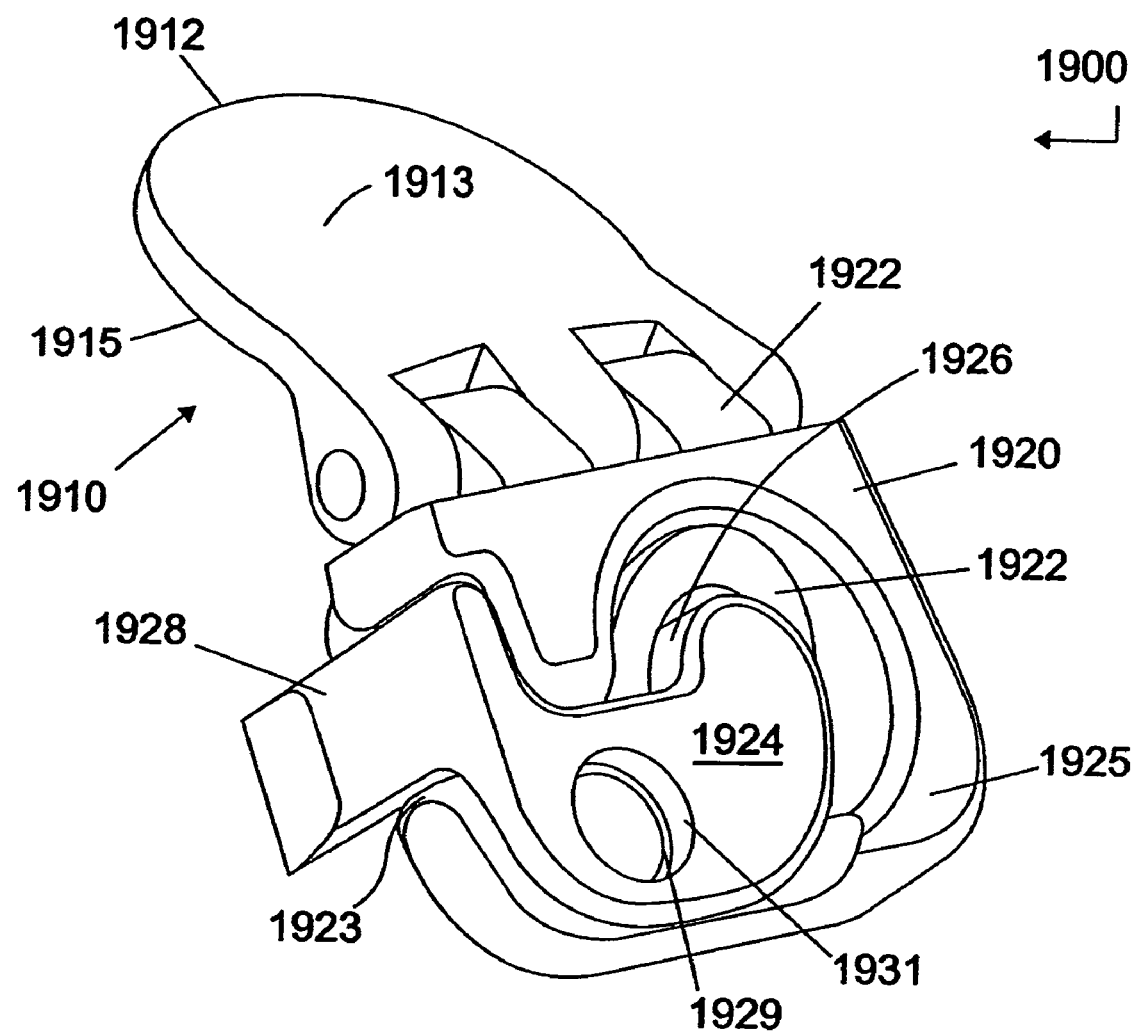
FIG. 25A shows a perspective view of a further embodiment of the implant of the invention.
Figure 25B:
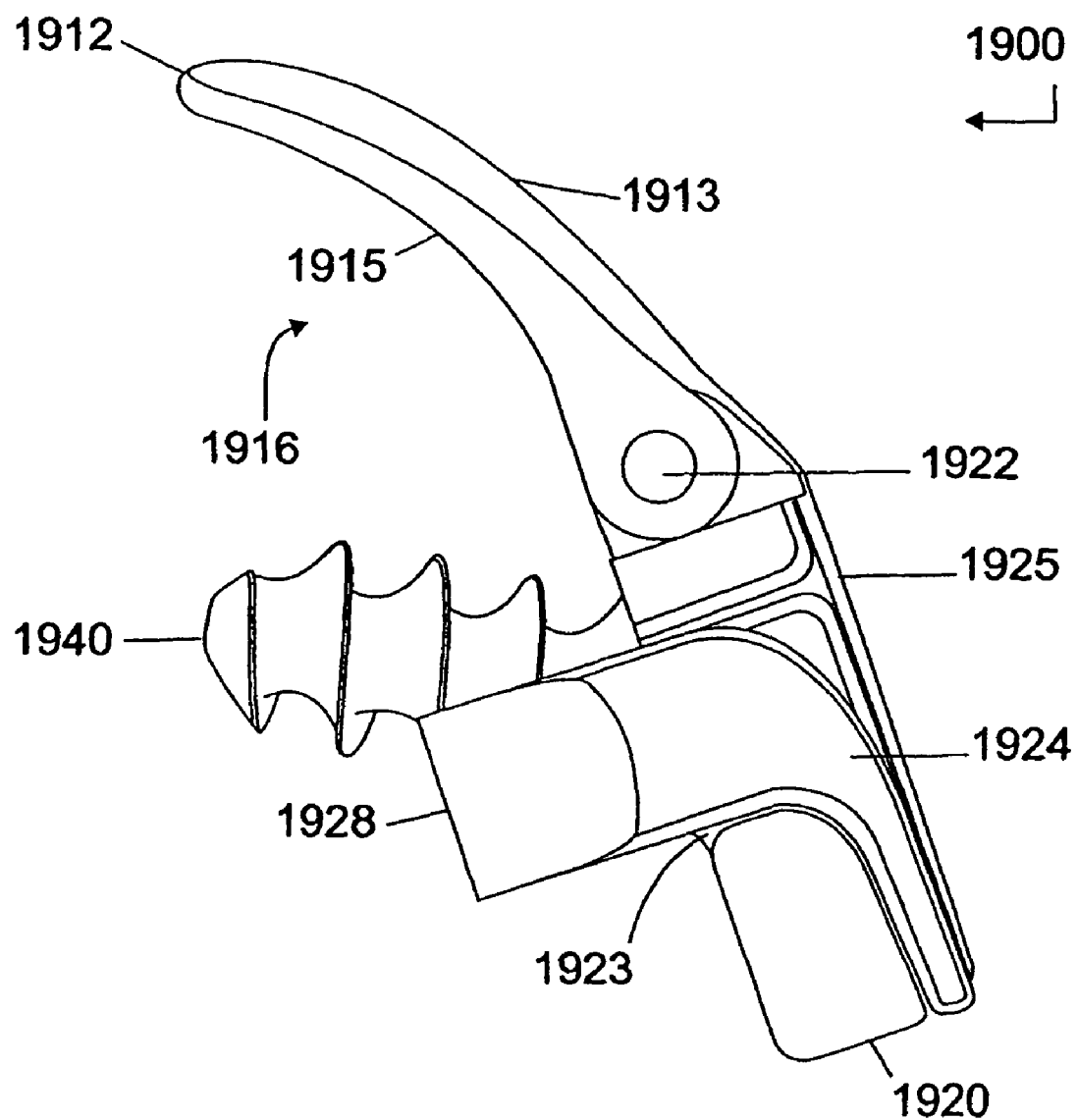
FIG. 25B shows a side view of the embodiment of the implant of the invention in FIG. 25A, having a curved, uniformly-thick artificial facet joint spacer or inter-facet spacer including a tapered end.

In the preferred embodiment depicted in FIGS. 25A, 25B, the lateral mass plate 1920 includes a recessed area 1922 for receiving the locking plate 1924 so that the locking plate 1924 is flush with the upper surface 1925 of the lateral mass plate 1920 when the probe 1926 is urged against the lateral mass screw 1940 and the keel 1928 is inserted into the lateral mass or the lamina of the vertebra. In the preferred embodiment depicted in FIGS. 25A, 25B, the shape and contours of the artificial facet joint spacer or inter-facet joint spacer 1910 can facilitate insertion of the artificial facet joint spacer or inter-facet joint spacer 1910 into the cervical facet joint. In this embodiment, the artificial facet joint spacer or inter-facet joint spacer 1910 has a rounded distal end 1912. The distal end 1912 is tapered in thickness to facilitate insertion. The tapered distal end 1912 meets, and is continuous with, a proximal mid-section 1916 which, in this preferred embodiment, has a uniform thickness, and is connected flexibly, preferably, with a hinge 1922, to the lateral mass plate 1920, as described above. The artificial facet joint spacer (or insert) or inter-facet joint spacer (or insert) 1910, with its proximal mid-section 1916 and tapered distal end 1912, is curved downward, causing a superior surface 1913 of the artificial facet joint spacer or inter-facet joint spacer 1910 to be curved. The curve can cause the superior surface 1913 to be convex, and the convexity can vary among different implants 1900 to suit the anatomical structure of the cervical facet joint(s) of a patient. An inferior surface 1915 accordingly can be preferably concave, flat, or convex. The curved shape of the implant can fit the shape of a cervical facet joint, which is comprised of an inferior facet of an upper vertebra and a superior facet of a lower adjacent vertebra. The convex shape of the superior surface 1913 of the artificial facet joint spacer or inter-facet joint spacer 1910 fits with a concave shape of the inferior facet of the upper cervical vertebrae. The concave shape of the inferior surface 1915 of the artificial facet joint spacer or inter-facet joint spacer 1910 fits with the convex shape of the superior facet of the cervical vertebrae. The degree of convexity and concavity of the artificial facet joint spacer or inter-facet joint spacer inferior and superior surfaces can be varied to fit a patient's anatomy and the particular pairing of adjacent cervical vertebrae to be treated. For example, a less-curved artificial facet joint spacer or inter-facet joint spacer 1910 can be used where the patient's cervical spinal anatomy is sized (as described below) and found to have less convexity and concavity of the articular facets. Generally for the same level the input for the right and left facet joint spacer or inter-facet joint spacer will be similarly shaped. It is expected that the similarity of shape of the artificial facet joint spacer or inter-facet joint spacer and the smooth, flush surfaces will allow distraction of the facet joint spacer or inter-facet joint spacer without loss of mobility or damage to the bones of the cervical spine Further, and preferably, the width of the mid-section 1916 is from 1.5 mm to 2.5 mm.

Except as otherwise noted above, the embodiment shown in FIGS. 22A-24B is similar to the embodiment shown in FIGS. 25A, 25B. Accordingly the remaining elements on the 1900 series of element numbers is preferably substantially similar to the described elements in the 1800 series of element numbers, as set forth above. Thus, by way of example, elements 1923, 1928, 1929 and 1930 are similar to respective elements 1823, 1828, 1829 and 1830.

Figure 29A:
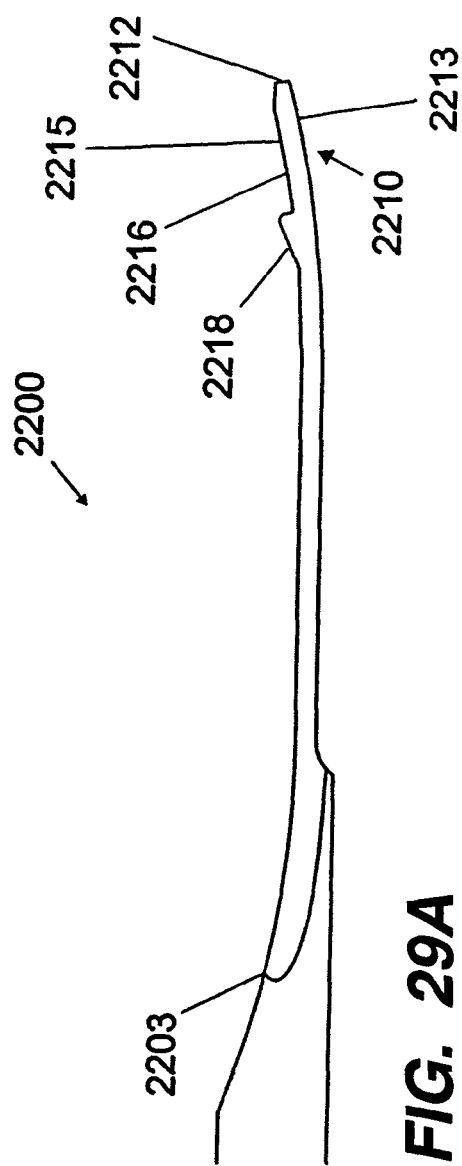
FIG. 29A depicts a side view of an embodiment of a sizing tool of the invention.
Figure 29B:
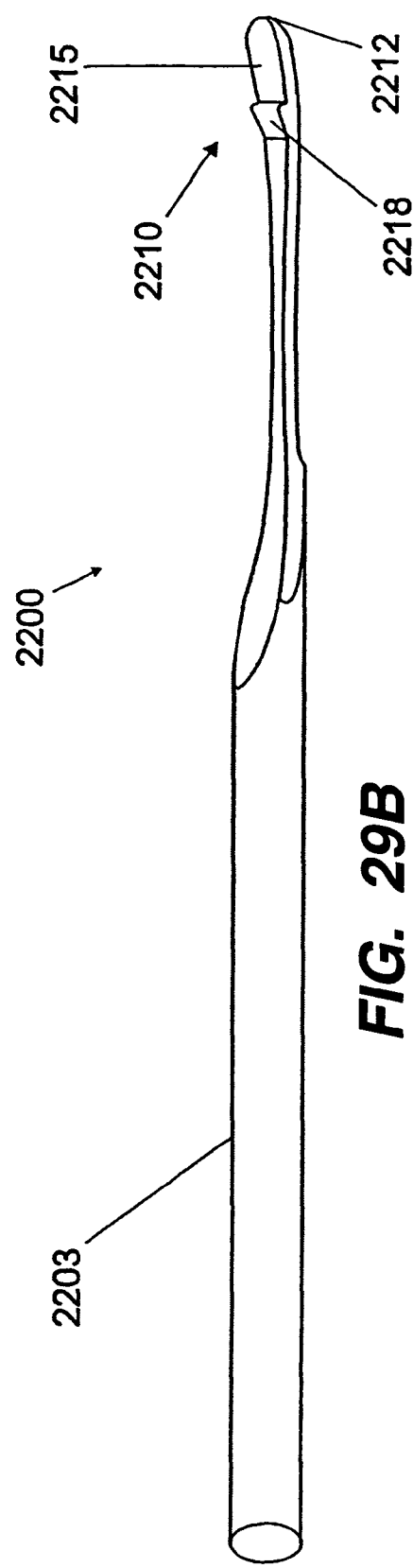
FIG. 29B depicts a top view of an embodiment of the sizing tool of the invention depicted in FIG. 29A.
Figure 29C:
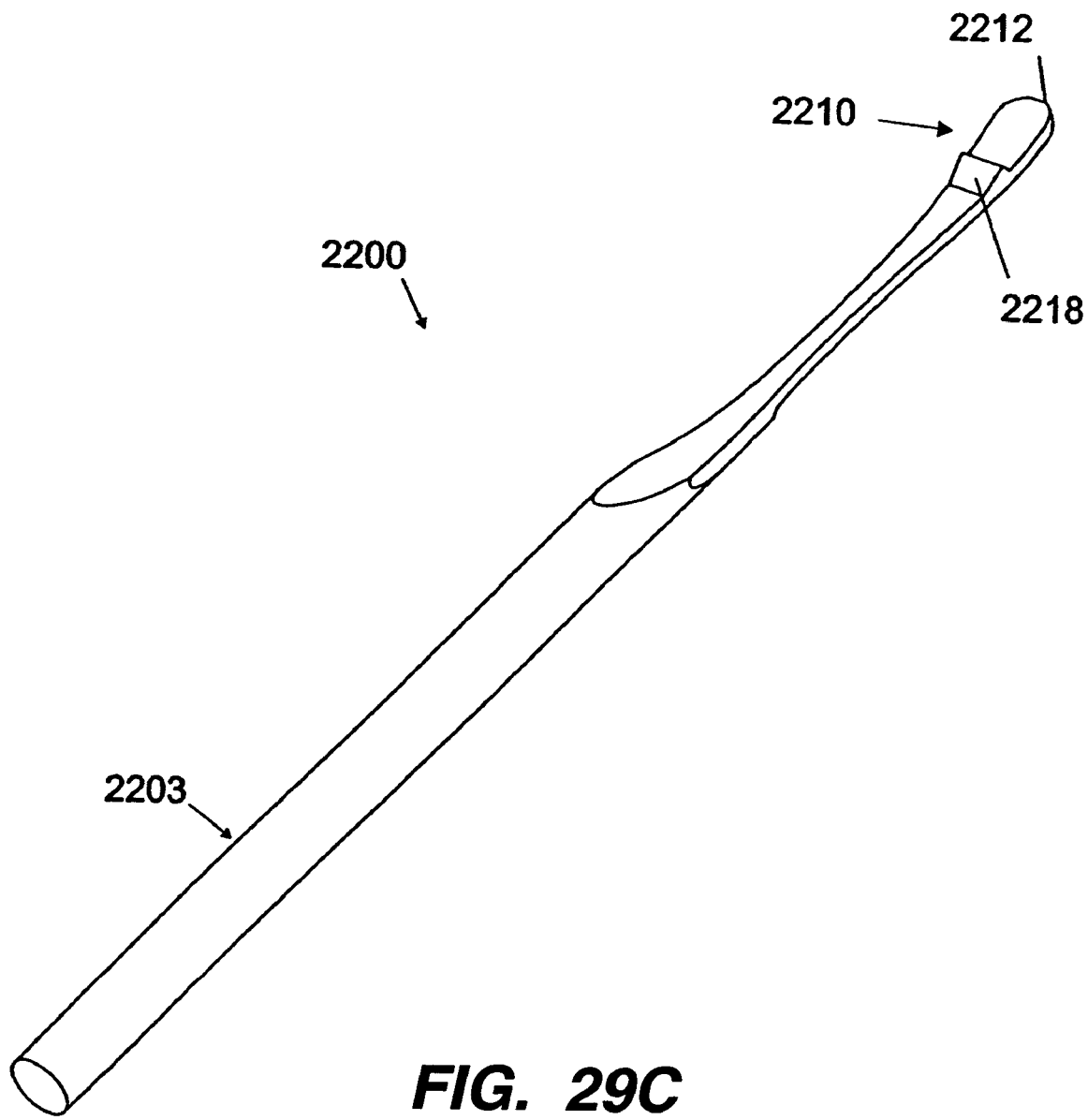
FIG. 29C depicts a perspective view of an embodiment of the sizing tool of the invention depicted in FIGS. 29A-B.
Figure 29D:
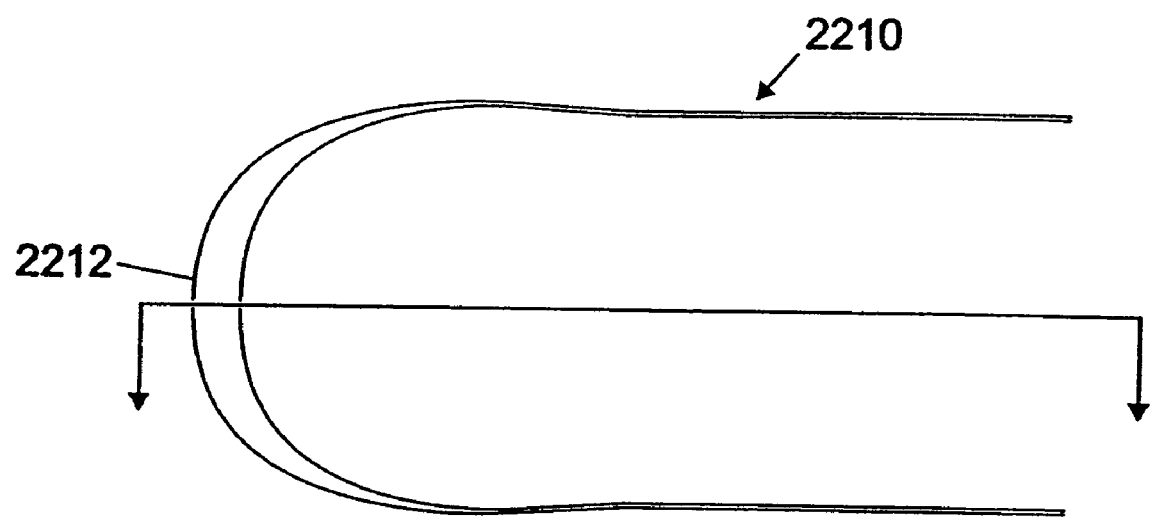
FIG. 29D depicts a side view of the head of the sizing tool of the invention depicted in FIG. 29A.
Figure 29E:
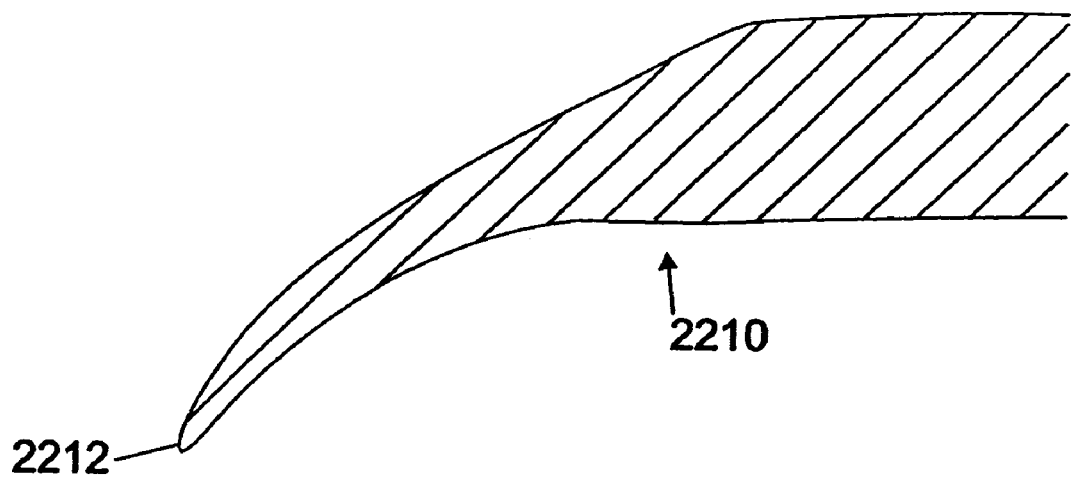
FIG. 29E depicts a cross-sectional view of the head of the sizing tool of the invention depicted in FIGS. 29A-C.
Figure 30:
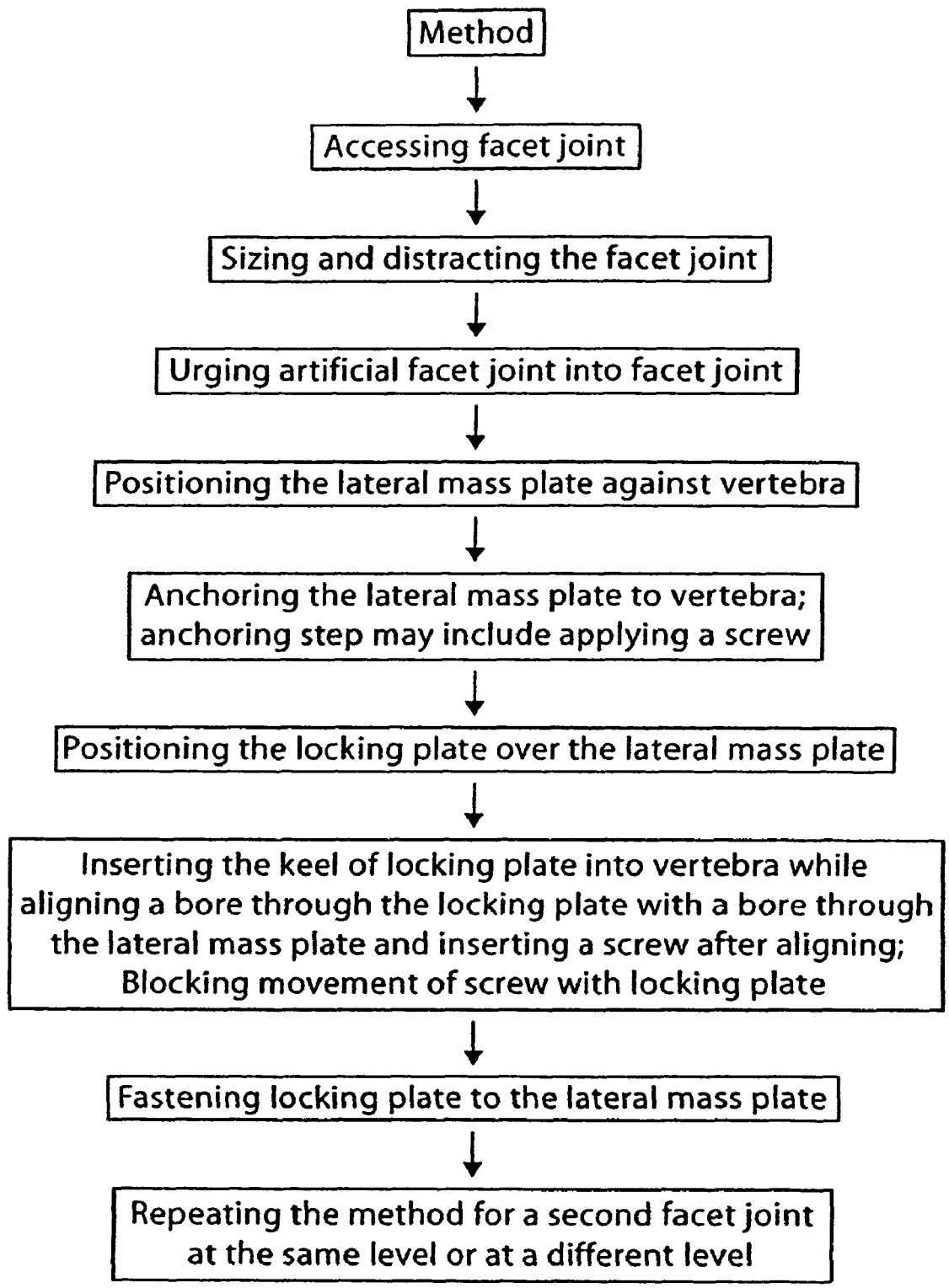
FIG. 30 is a flow diagram of an embodiment of a method of the invention.

FIG. 30 is a flow chart of the method of insertion of an implant of the invention. The embodiment 1800 or 1900 of the present invention preferably is inserted in the following manner (only elements of the embodiment 1800 will be set forth herein, for purposes of the written description of a method of the invention). First, the facet joint is accessed. A sizing tool 2200 (see FIGS. 29A-C) can be inserted to select the appropriate size of an implant of the invention for positioning in the cervical facet joint. This step may be repeated, as necessary, with, if desired, different sizes of the tool 2200 until the appropriate size is determined. This sizing step also distracts the facet joint and surrounding tissue in order to facilitate insertion of the implant. Then, the natural (made from animal bone) or artificial facet joint spacer or inter-facet joint spacer 1810 is urged between the facets into the facet joint. The facet itself is somewhat shaped like a ball and socket joint. Accordingly, in order to accommodate this shape, the artificial joint spacer or inter-facet joint spacer 1810 can have a rounded leading edge shaped like a wedge or tissue expander to cause distraction of the facet joint as the artificial facet joint spacer or inter-facet joint spacer is urged into the facet joint of the spine. The artificial facet joint spacer or inter-facet joint spacer 1810 also includes the convex surface 1813 in order to more fully accommodate the shape of the facet joint of the spine. However, as set forth above and as depicted in FIG. 25B, it is possible in the alternative to have a curve-shaped artificial facet joint spacer (or insert) or inter-facet joint spacer (or insert) 1910 with a convex superior surface 1913 and a concave inferior surface 1915, the distal end 1912 tapering to facilitate insertion, while the remainder of the artificial facet joint spacer or inter-facet joint spacer 1910, (i.e., the proximal section 1916) has a uniform thickness.

Once the artificial joint spacer or inter-facet joint spacer 1810 is positioned, the lateral mass plate 1820 is pivoted downward about the hinge 1822 adjacent to the vertebrae and preferably to the lateral mass or to the lamina. Thus, the lateral mass plate 1820 may be disposed at an angle relative to the artificial facet joint spacer or inter-facet joint spacer 1810 for a representative spine configuration. It is to be understood that as this embodiment is hinged the final position of the lateral mass plate 1820 relative to the artificial facet joint spacer or inter-facet joint spacer 1810 will depend on the actual spine configuration. It is to be understood that embodiments of the invention can be made without a hinge, as long as the connection between the artificial facet joint spacer or inter-facet joint spacer and the lateral mass plate is flexible enough to allow the lateral mass plate to be bent relative to the artificial facet joint spacer or inter-facet spacer in order to fit the anatomy of the patient. Once the lateral mass plate 1820 is positioned, or prior to the positioning of the lateral mass plate 1820, a bore can be drilled in the bone to accommodate the bone screw 1824. Alternatively, the screw 1824 can be self-tapping. The screw is then placed through the bore 1830 and secured to the bone, preferably the lateral mass or the lamina, thereby holding the artificial facet joint spacer or inter-facet joint spacer 1810 in place. In order to lock the bone screw 1824 in place and to lock the position of the artificial facet joint spacer or inter-facet joint spacer 1810 and the lateral mass plate 1820 in place, the locking plate 1824 is positioned over the lateral mass plate 1820. So positioned, the probe 1826 is positioned through the bore 1830 and against the head of the bone screw to keep the bone screw from moving. The keel 1828, having a sharp chisel-shaped end, preferably can self-cut a groove in the bone so that the keel 1828 is locked into the bone as the keel 1828 is aligned by, and received in, a groove 1831 of the lateral mass plate 1820. Alternatively, a groove can be pre-cut in the bone to receive the keel 1828. As this occurs the bore 1829 of the locking plate 1824 aligns with the threaded bore 1831 of the lateral mass plate 1820 and a machine screw can be inserted to lock the locking plate relative to the lateral mass plate. This locking prevents the lateral mass plate 1820 and the artificial facet joint spacer or inter-facet joint spacer 1810 from rotating and, as previously indicated, prevents the bone screw 1840 from backing out from the vertebra. Preferably the implant is between the C5 and C6 vertebrae level, or the C6 and C7 vertebrae level. It is noted that two implants preferably will be implanted at each level between vertebrae. That is, an implant 1800 will be placed in a right facet joint and also in a left facet joint when viewed from a posterior view point. This procedure can be used to increase or distract the foraminal area or dimension of the spine in an extension or in neutral position (without having a deleterious effect on cervical lordosis) and reduce the pressure on the nerves and blood vessels. At the same time this procedure preserves mobility of the facet joint.

Figure 26A:
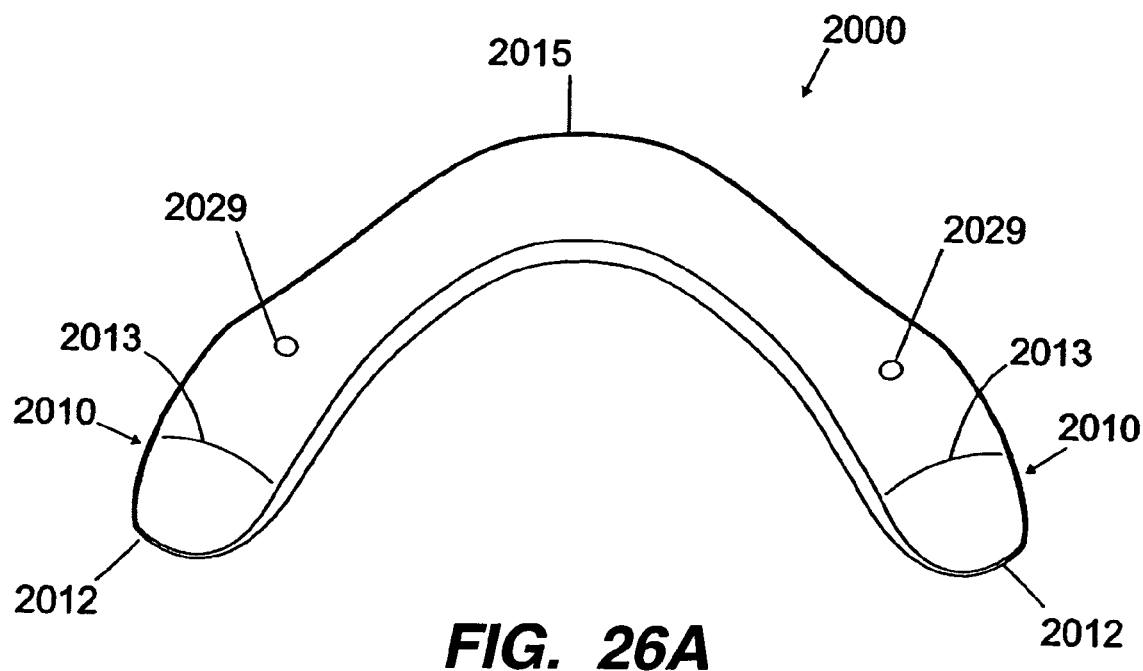
FIG. 26A shows an anterior perspective view of a further embodiment of the implant of the invention.
Figure 26B:
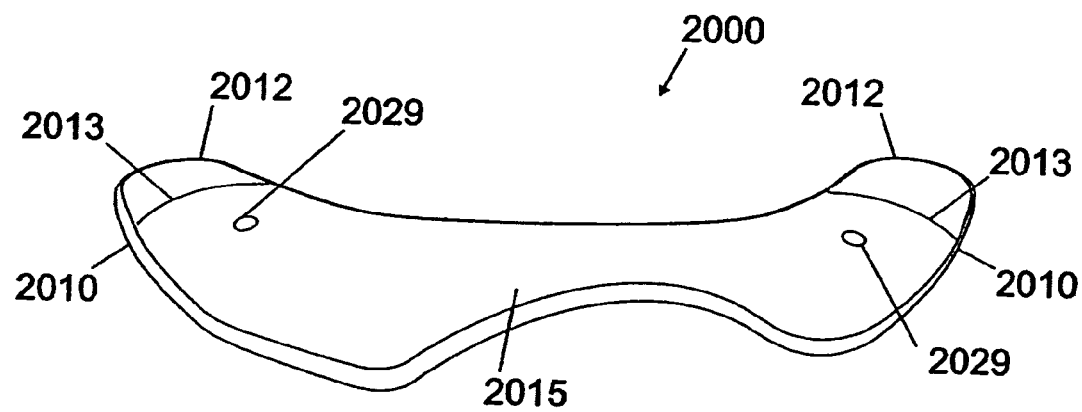
FIG. 26B shows a posterior perspective view of the embodiment of the implant of the invention depicted in FIG. 26A.
Figure 27A:
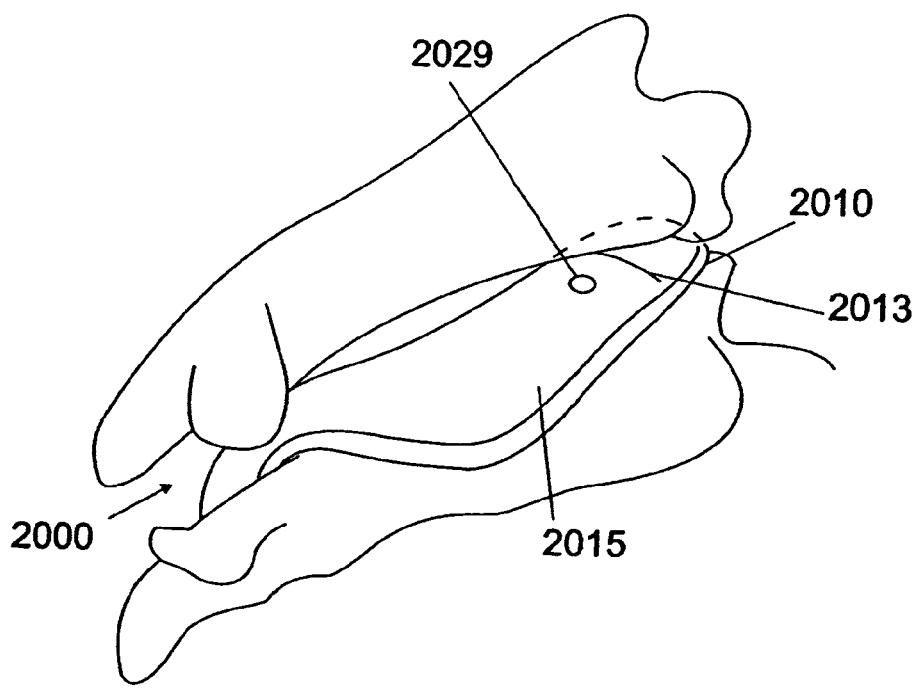
FIG. 27A depicts a side view of the embodiment of the implant of the invention shown in FIGS. 26A and 26B, implanted in the cervical spine.
Figure 27B:
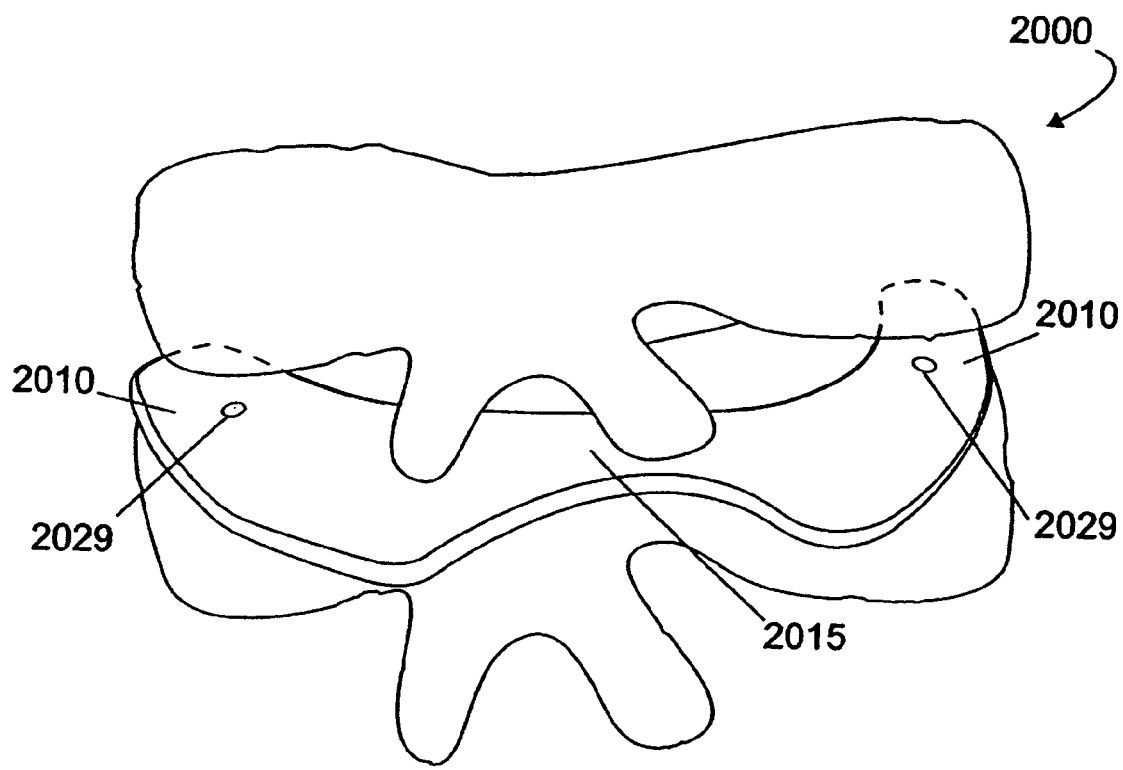
FIG. 27B shows a posterior view of the embodiment of the implant of the invention shown in FIGS. 26A, 26B, and 27A, implanted in the cervical spine.

FIGS. 26A-27B show a further embodiment of the implant of the invention, with the embodiment 2000 implanted in the cervical spine as depicted in FIGS. 27A and 27B. The implant 2000 comprises a first artificial facet joint spacer (or insert) or inter-facet joint spacer (or insert) 2010 and a second artificial facet joint spacer (or insert) or inter-facet joint spacer (or insert) 2010. Each artificial facet joint spacer or inter-facet joint spacer can have a distal end 2012 that is tapered or wedge-shaped in a way that facilitates insertion into the cervical facet joints on both sides of two adjacent cervical vertebrae at the same level. The artificial facet joint spacers or inter-facet joint spacers further can be dome-shaped, or convex on a superior surface 2013, to approximate the shape of the cervical facets of the cervical facet joints.

Figure 28A:
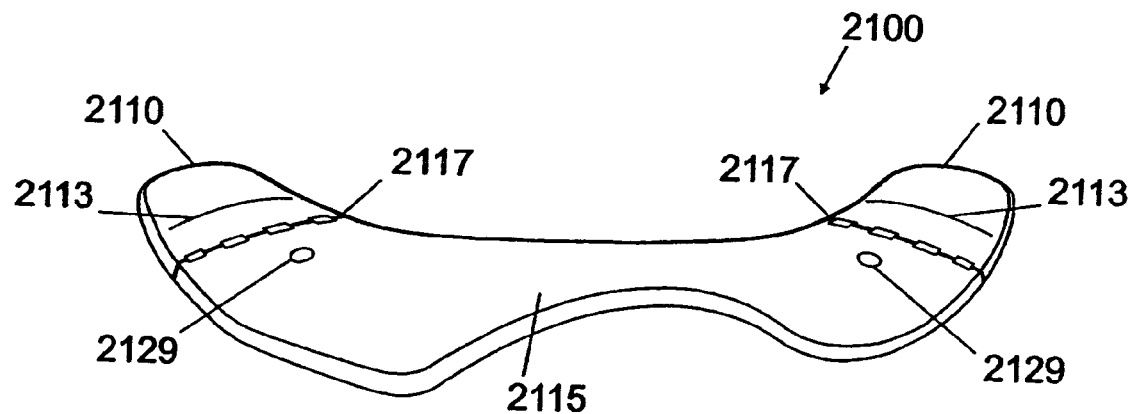
FIG. 28A depicts a posterior perspective view of a further embodiment of the implant of the invention.
Figure 28B:
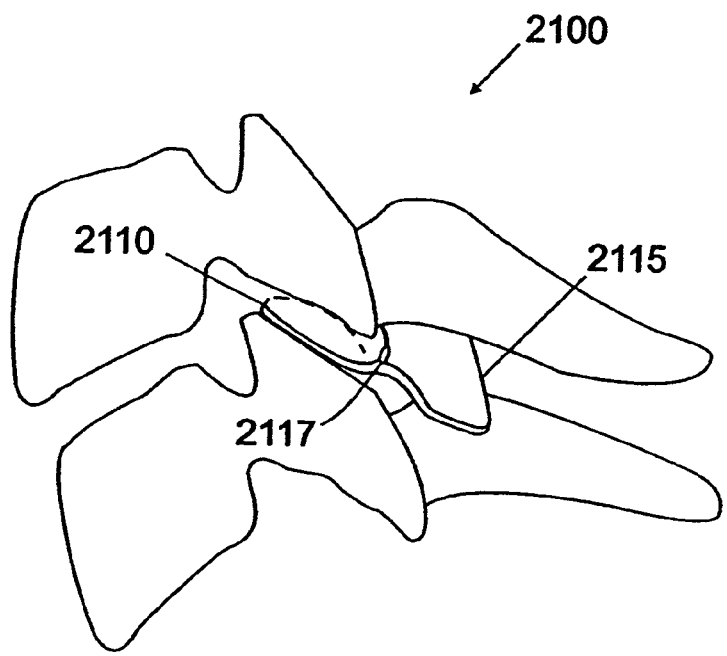
FIG. 28B depicts a side view of the embodiment of the implant of the invention shown in FIG. 28A.

The first and second artificial facet joint spacers or inter-facet joint spacers 2010 are bridged together by a collar 2015. The collar 2015 passes between the spinous processes of the adjacent cervical vertebrae. As can be seen in FIG. 26B, the implant can preferably be "V" shaped or "boomerang" shaped. The entire implant 2000 or the collar 2015 of the implant can be made of a flexible material such as titanium, so that it is possible to bend the collar 2015 so that it conforms preferably to the shape of the lateral mass or the lamina of the cervical vertebrae of the patient and thereby holds the implant in place with the artificial facet joint spacers or inter-facet joint spacers 2010 inserted in the cervical facet joints. Bores 2029 are preferably are provided through implant 2000 adjacent to the artificial facet joint spacer or inter-facet joint spacer 2010, respectively. These bores 2029 can receive bone screws to position the implant 2000 against the lateral mass or the lamina as shown in FIGS. 27A, 27B. The description of the embodiment 2100, in FIGS. 28A, 28B provide further details concerning the method of affixing the implant 2000 to the vertebrae. The implant 2100 also can be made of PEEK or other materials as described herein. Embodiment 2000 (the "boomerang" shape depicted in FIG. 27B) further can have a locking plate as, for example, the locking plate 1824 in FIG. 22A. The locking plate for embodiment 2000 (not shown) can have the same features as locking plate 1824, that is: (1) a probe 1826 that interacts with the bone screws to prevent the bone screws from backing out of the bone, the likely consequence of which would be displacement of the implant 2000; and (2) a keel 1828 with a chisel end to embed in the bone and thus to prevent rotational displacement of the implant. However, given the collar 2015 configuration of embodiment 2000, a chisel may not serve the same purpose as with the embodiments set forth above, which lack a collar stabilized by two bone screws. Therefore, a locking plate on embodiment 2000 can be provided without a keel.

FIGS. 28A and 28B depict a further embodiment of the implant of the invention 2100. In this embodiment 2100, the collar 2115 can be made of a flexible material such as titanium, of a substantially inflexible material, or of other materials described herein. Substantial flexibility can also be derived from connecting a first artificial facet joint spacer (or insert) or inter-facet joint spacer (or insert) 2110 with the collar 2115 using a first hinge 2117, and connecting a second artificial facet joint spacer (or insert) or inter-facet joint spacer (or insert) 2110 with the collar 2115 using a second hinge 2117. Using the first hinge 2117 and the second hinge 2117, the collar 2115 can be pivoted downward to conform to a particular patient's cervical spinal anatomy. In other words, the degree of pivoting will vary among different patients, and the first hinge 2117 and second hinge 2117 allow the implant 2100 to accommodate the variance.

In the hinged embodiment 2100, and similar to the embodiment 2000, the collar 2115 can have a first bore 2129 inferior to the first hinge 2117, and a second bore 2129 inferior to the second hinge 2117. A first bone screw penetrates the first bore 2130 and into the lateral mass or the lamina, and the second bone screw penetrates the second bore 2130 and into the lateral mass or the lamina, the first and second bone screws serving to anchor the implant. A bore, preferably in the lateral mass, can be drilled for the first bone screw and for the second bone screw. Alternatively, the bone screws can be self-tapping. A first locking plate similar to the plate 1924 (FIG. 25A) can be secured about the head of the first bone screw and a second locking plate can be secured about the head of the second bone screw to prevent displacement of the first and second bone screws 2140. The first locking plate can block the first bone screw with a probe and the second locking plate can block to the second bone screw with a probe.

It should be noted that embodiments 2000 and 2100 also can be configured for accommodating treatment of cervical spinal stenosis and other cervical spine ailments where only a single cervical facet joint between adjacent vertebrae requires an implant, i.e., where treatment is limited to one lateral facet joint. In that case, the collar 2015, 2115 extends medially without extending further to join a second artificial facet joint spacer or inter-facet joint spacer 2010, 2110. For the hinged embodiment 2100, the implant comprises a single hinge 2117, and the collar 2115 has only one bore 2129 to accept one bone screw to secure the implant 2100.

FIGS. 29A-E, depict a sizing and distracting tool 2200 of the invention. Sizing tool 2200 has a handle 2203 and a distal head 2210 that is shaped as artificial facet joint spacer or inter-facet joint spacer (e.g., 1810) of an implant of the invention. That is, the head 2210 preferably will have essentially the same features as the artificial facet joint spacer or inter-facet joint spacer 1810, but the dimensions of the head 2210 will vary from one tool 2200 to the next, in order to be able to use different versions of the sizing tool 2200 to determine the dimensions of the cervical facet joint that is to be treated and then to select an appropriately-sized implant. The head 2210 preferably can be used to distract the facet joint prior to the step of implanting the implant in the facet joint. In this regard, the head 2210 is rounded at the most distal point 2212, and can be a tapered to facilitate insertion into a cervical facet joint. The head 2210 also can have a slightly convex superior surface 2213, the degree of convexity varying among different sizing tools 2200 in order to determine the desired degree of convexity of an implant to be implanted in the cervical facet joint. The head 2210 may have a uniform thickness along a proximal mid-section 2216. Accordingly, the inferior surface 2215 preferably can be concave. Alternatively, the proximal mid-section 2212 may be convex on the superior surface 1813 without being uniform in thickness. Thus, the inferior surface 2215 can be flat or planar. The head also can be curved.

The head 2210 has a stop 2218 to prevent over-insertion of the head 2210 of the sizing tool 2200 into the facet joint. The stop 2218 can be a ridge that separates the head 2210 from the handle 2203. Alternatively, the stop 2218 can be any structure that prevents insertion beyond the stop 2218, including pegs, teeth, and the like.

Different sizing tools 2200 covering a range of dimensions of the head 2210 can be inserted successively into a cervical facet joint to select the appropriate size of an implant to position in the cervical spine, with the appropriate convexity and concavity of the artificial facet joint spacer or inter-facet joint spacer. Each preferably larger head also can be used to distract the facet joint.

Figure 31A:
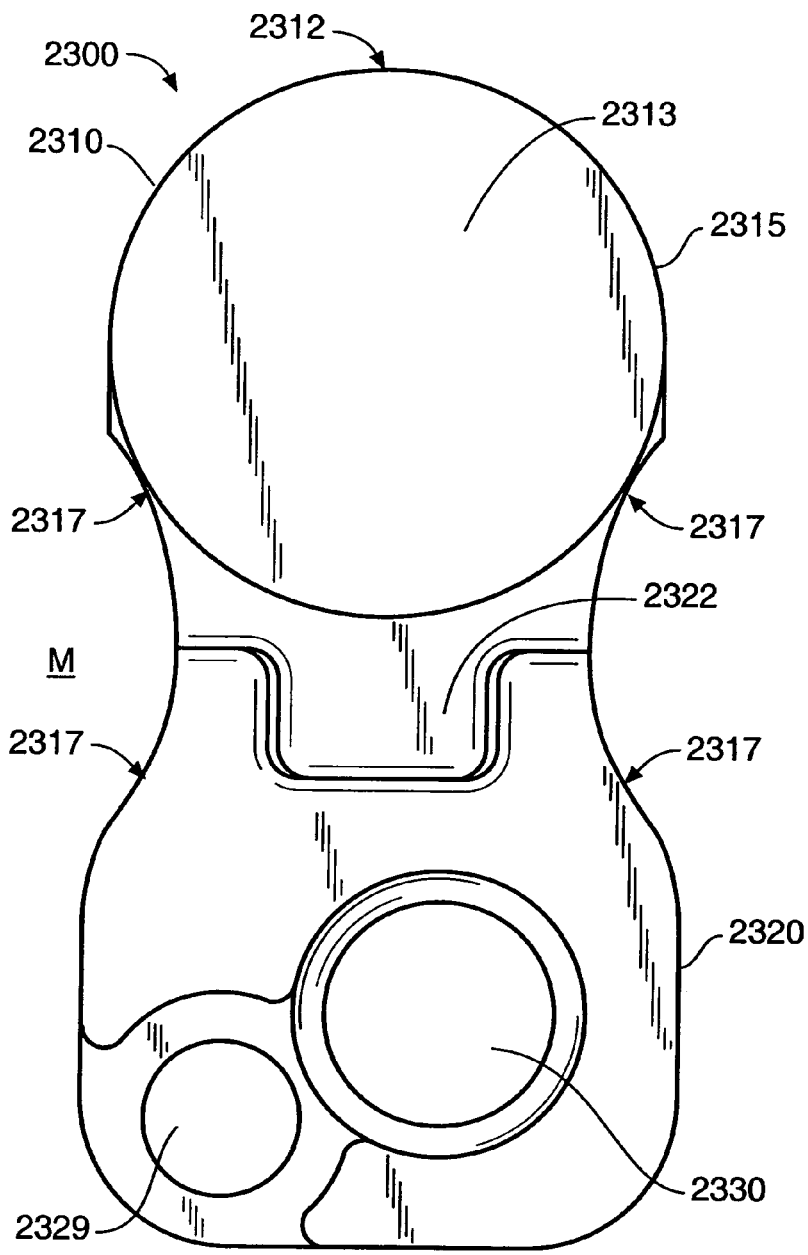
FIG. 31A is posterior view of a further embodiment of the implant of the invention.

FIG. 31A depicts a posterior view of a further embodiment 2300 of the implant of the invention. Embodiment 2300, as well as all of the embodiments herein, can benefit from some or all of the advantages described herein with regard to the other embodiments described herein. Further, FIG. 31A, embodiment 2300 has an artificial facet joint spacer (or insert) or inter-facet joint spacer (or insert) 2310 that can have a tapered or thinned distal end 2312 so that the distal end 2312 facilitates insertion of the artificial facet joint spacer or inter-facet joint spacer 2310 into a cervical facet joint. The distal end 2312 can be rounded, as seen in the plan view of FIG. 31A, in order to conform to the roundness of the facet joint. The artificial facet joint spacer or inter-facet joint spacer 2310 further can be curved so that a superior surface 2313 of the artificial facet joint spacer or inter-facet joint spacer 2310 is convex, and an inferior surface 2315 is concave, to approximate the natural shape of the cervical facet joint that is to receive the implant 2300. The curve can have a uniform thickness, or it can have a varied thickness. Further, the lateral edges of the artificial facet joint spacer or inter-facet joint spacer 2310 are curved or rounded, for distribution of load-bearing stress. As with other embodiments described herein, the artificial facet joint spacer or inter-facet joint spacer 2310 also can be made of a flexible, biocompatible material, such as PEEK, to maintain joint mobility and flexibility.

The artificial facet joint spacer or inter-facet joint spacer 2310 is connected flexibly with a lateral mass plate 2320, the flexible connection preferably being a hinge 2322. As seen in the plan view of FIG. 31A, the implant 2300 is substantially hour-glass shaped. This shape, as well as the shape of FIG. 32, will be discussed further below. The hinge 2322 is narrower than the artificial facet joint spacer or inter-facet joint spacer 2310, with the hinge 2322 sitting at substantially the isthmus 2317 between artificial facet joint spacer or inter-facet joint spacer 2310 and the lateral mass plate 2320. The curved edges, or fillets, about the hinge 2322 serve to distribute more evenly the load-bearing stress on the implant 2300, and thus prevent concentrating the stress about the edges.

The hinge 2322 allows the implant 2300 to bend at the hinge 2322, bringing a lateral mass plate 2320 adjacent to the lateral mass and/or lamina of the patient's spine, and to conform to a particular patient's anatomy. The lateral mass plate 2320 is made of a biocompatible flexible material, preferably titanium or any other biocompatible flexible material as described herein, for example PEEK, that will support the use of bone screws and other hardware, as described below. The lateral mass plate 2320 bends downward at the hinge 2322 over a wide range of angles relative to the artificial facet joint spacer or inter-facet joint spacer 2310, and preferably at an angle of more than 90 degrees, and this flexibility facilitates positioning and insertion of the artificial facet joint spacer or inter-facet joint spacer. This flexibility of the lateral mass plate 2320 relative to the artificial facet joint spacer or inter-facet joint spacer 2310 further facilitates positioning of the lateral mass plate relative to the lateral mass and/or the lamina of the patient's spine. Once the lateral mass plate 2320 is positioned adjacent to the bone, preferably the lateral mass of a cervical vertebra, a first bone screw, such as bone screw 1840, can be inserted through a first bore 2330 through the lateral mass plate 2320 and embedded into the bone of the lateral mass of the cervical vertebra.

The lateral mass plate 2320 further comprises a second bore 2329 which is preferably positioned medially, relative to the first bore 2330. Thus, viewing the implant from a posterior perspective as in FIG. 31A, the second bore 2329 in the lateral mass plate 2320 can be positioned either to the left or to the right of the first bore 2330. The position of the second bore 2329 will depend upon whether the implant 2300 is intended to be inserted into a cervical facet joint on the left or right side of a patient. Specifically, an implant 2300 to be inserted into a right-side cervical facet joint (i.e., the patient's rights side) will have a second bore 2329 positioned to the left of the first bore 2330 as in FIG. 31A, when implant 2300 is viewed from a posterior perspective, while an implant 2300 to be inserted into a left-side cervical facet joint will have a second bore 2329 positioned to the right of the first bore 2330, when implant 2300 is viewed from a posterior perspective.

Figure 31B:
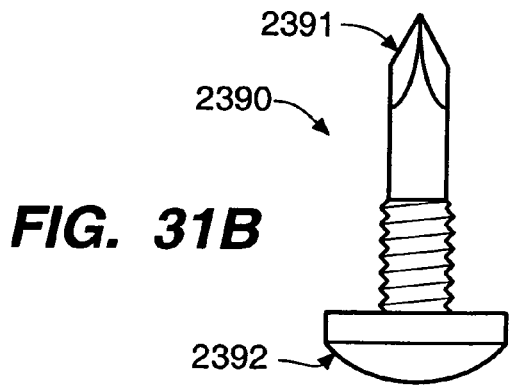
FIG. 31B is a side view of an embodiment of a locking screw of the implant of the invention depicted in FIG. 31A.

The second bore 2329 through the lateral mass plate 2320 is adapted to accept a second screw 2390 (FIG. 31B), which preferably is a locking screw with a chisel point 2391. The locking screw 2390 is received by the second bore 2329 and the chisel point 2391 self-cuts a bore into the bone. The locking screw 2390 preferably is inserted through the second bore 2329 and embedded in the bone, after the bone screw is embedded in the bone through the first bore 2330. The position of the second bore 2329, i.e., medial to the first bore 2330, positions the locking screw 2390 so that it embeds in stronger bone tissue than if the second bore 2329 were located more laterally. The locking screw, in combination with the bone screw, prevents rotational and/or backward displacement of the implant 2300. As the locking screw 2390 is received by the second bore 2329, the head 2392 of the locking screw 2390 aligns with the head of the first bone screw in the first bore 2330, blocking the head of the first bone screw to prevent the first bone screw from backing out of the bone of the vertebra and the first bore 2330.

Figure 32:
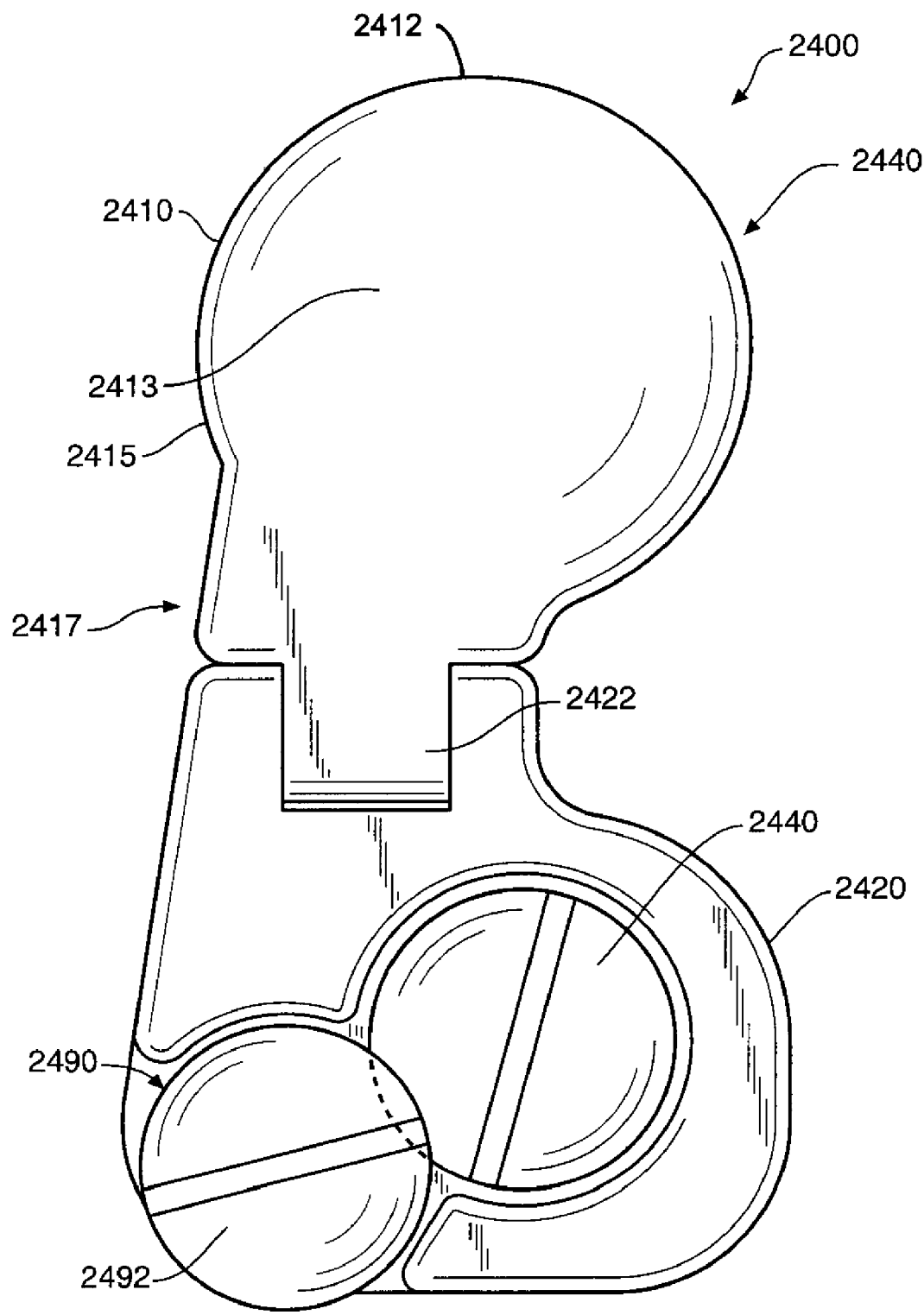
FIG. 32 is a posterior view of a further embodiment of the implant of the invention.

FIG. 32 depicts a further embodiment 2400 of the implant of the invention, from a posterior view. Embodiment 2400 is adapted to be implanted in a manner that preserves the anatomy of the cervical facet joint, in particular, the soft tissues around the cervical facet joint, including the joint capsule.

Implant 2400, like implant 2300 and other implants disclosed above, has an artificial facet joint spacer (or insert) or inter-facet joint spacer (or insert) 2410, flexibly connected, preferably by a hinge 2422, to a lateral mass plate 2420. As can be seen in FIG. 32, the implant 2400 including the artificial facet joint spacer (or insert) or inter-facet joint spacer (or insert) 2410 and the hinge 2422 is substantially "P" shaped. As explained below, its "P" shape assists in the insertion of the implant 2400 into the facet joint with most of the facet capsule and facet capsule ligament and other soft tissue associated with the facet joint still left intact. The artificial facet joint spacer or inter-facet joint spacer, as above for implant 2300 and the other implants disclosed above, can have a superior surface 2413 of the artificial facet joint spacer or inter-facet joint spacer 2410 that is convex, and an inferior surface 2415 that is concave, or any appropriate shaping to approximate the natural shape of the cervical facet joint that is to receive the implant 2400. The thickness of the artificial facet joint spacer or inter-facet joint spacer 2410 can be uniform, or varied. The artificial facet joint spacer or inter-facet joint spacer 2410 also can be made of a flexible, biocompatible material, such as PEEK, to maintain joint mobility and flexibility. The hinge 2422 can have smooth, rounded edges, for distribution of load stress, as disclosed above. Other features and advantages of the other embodiments can be, if desired, incorporated into the design of the embodiment of FIG. 32. For example, the artificial facet joint spacer or inter-facet joint spacer 2410 further can have a tapered or thinned edge 2412 so that the edge 2412 facilitates insertion of the artificial facet joint spacer or inter-facet joint spacer 2410 into a cervical facet joint. The edge 2412 can be curved. In this embodiment 2400, however, the thinned edge 2412 of the artificial facet joint spacer or inter-facet joint spacer 2410 preferably is not at the distal end of the artificial facet joint spacer or inter-facet joint spacer 2410 as is the thinned edge 2312 of the artificial facet joint spacer or inter-facet joint spacer 2310; rather, the thinned edge 2412 preferably is positioned laterally, toward the hinge 2422 of the implant 2400. The thinned edge 2412 coincides substantially with a lateral curvature 2440 of the artificial facet joint spacer or inter-facet joint spacer 2410, which is pronounced relative to the curvature on the medial side of the implant 2400, i.e., a "P" shape. In other words, the curved part of the head of the "P" 2440 corresponds to the thinned edge 2412, and serves as the leading edge of the implant 2400 to begin insertion of the artificial facet joint spacer or inter-facet joint spacer 2410 into a cervical facet joint, preferably through an incision in the soft tissue of the facet joint. The "P" shape narrows at isthmus 2417 where the artificial facet joint spacer or inter-facet joint spacer 2410 that is joined by the hinge 2422 with the lateral mass plate 2420. The smooth or rounded edges or fillets serve to distribute stresses on the implant 2400. The above described "P" shape of implant 2400 allows the implant 2400 to be pivoted into place into a facet joint as described below. The thinned edge 2412 and leading lateral curvature 2440 of the artificial facet joint spacer or inter-facet joint spacer 2410 are adapted to facilitate urging implant 2400 into the cervical facet joint, through the incision in the joint capsule. The implant 2400 then is pivoted into position so that the lateral mass plate 2420 can be bent downward, relative to the artificial facet joint spacer or inter-facet joint spacer 2410, to align with and lie adjacent to the lateral mass and/or the lamina. The lateral mass plate 2420 is then fastened to the bone.

The lateral mass plate 2420 of implant 2400, like the lateral mass plate for implant 2300, is flexibly connected, preferably by the smooth-edged hinge 2422, to the artificial facet joint spacer or inter-facet joint spacer 2410 at the narrow lower part of the artificial facet joint spacer or inter-facet joint spacer. The lateral mass plate 2420 is made of a biocompatible flexible material, preferably titanium or any other biocompatible flexible material such as PEEK that will support the use of bone screws and other hardware, as described below.

The lateral mass plate 2420 bends downward at a wide range of angles relative to the artificial facet joint spacer or inter-facet joint spacer 2410, and preferably at an angle of more than 90 degrees. The flexibility of the lateral mass plate 2420 relative to the artificial facet joint spacer or inter-facet joint spacer 2410 further facilitates positioning of the lateral mass plate 2420 relative to the lateral mass and/or the lamina of the patient's spine.

Like embodiment 2300, described above, the lateral mass plate 2420 has first bore 2430, which is adapted to receive a bone screw 2440, to help anchor implant 2400 in position. The lateral mass plate 2420 further includes a second bore 2429 adapted to be positioned medially, relative to the first bore 2430, as disclosed above for implant 2300. The position of the second bore 2429, when viewing implant 2400 from a posterior perspective (FIG. 32), will depend upon whether implant 2400 is intended to be implanted into a left-side or right-side cervical facet joint of a patient. Thus, implant 2400 with the second bore 2429 positioned to the left of the first bore 2430 is intended to be implanted in a right-side cervical facet joint of a patient, as depicted in FIG. 32, while an implant 2400 with a second bore 2429 positioned to the right of the first bore 2430 is intended to be implanted in a left-side cervical facet joint of a patient.

The second bore 2429 through the lateral mass plate 2420 is adapted to receive a second screw 2490 with head 2492, which preferably is a locking screw with a chisel point, such as screw 2390. The function and purpose of the bone screw disposed through bore 2430 and the locking screw disposed through bore 2429 are as described above with respect to the implant 2300.

Figure 33A:
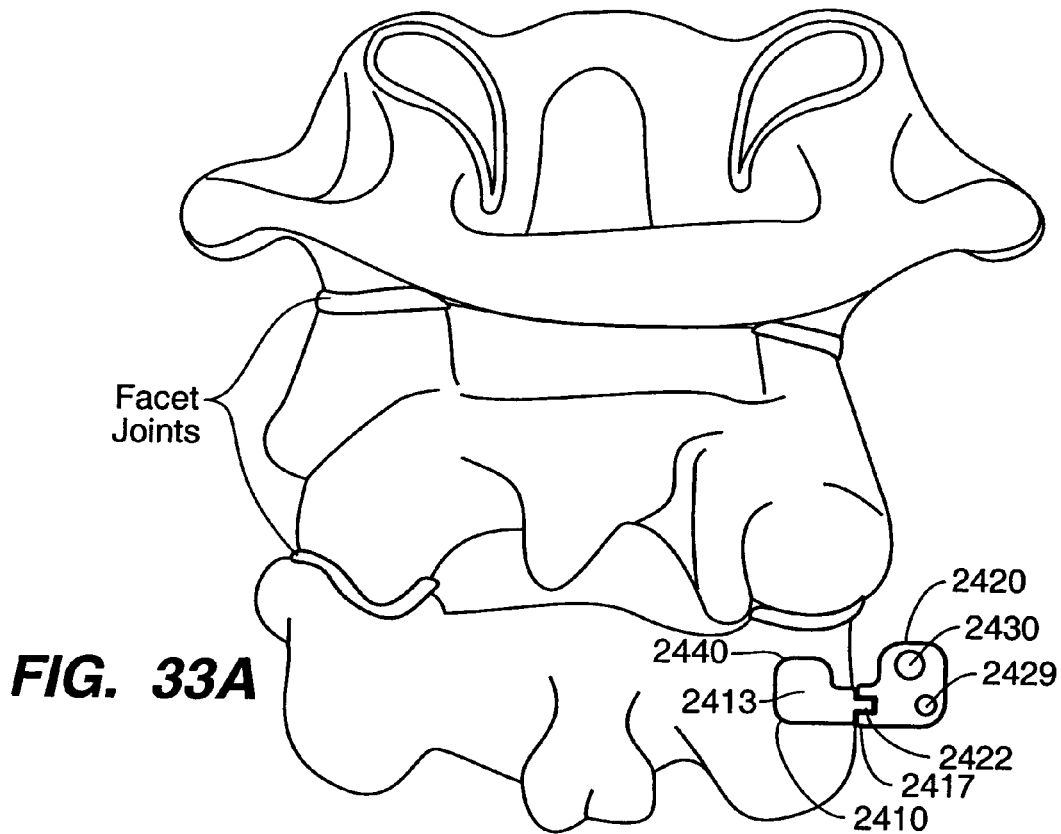
FIGS. 33A and 33B depict initial and final insertion positions of the embodiment of the invention depicted in FIG. 32.
Figure 33B:
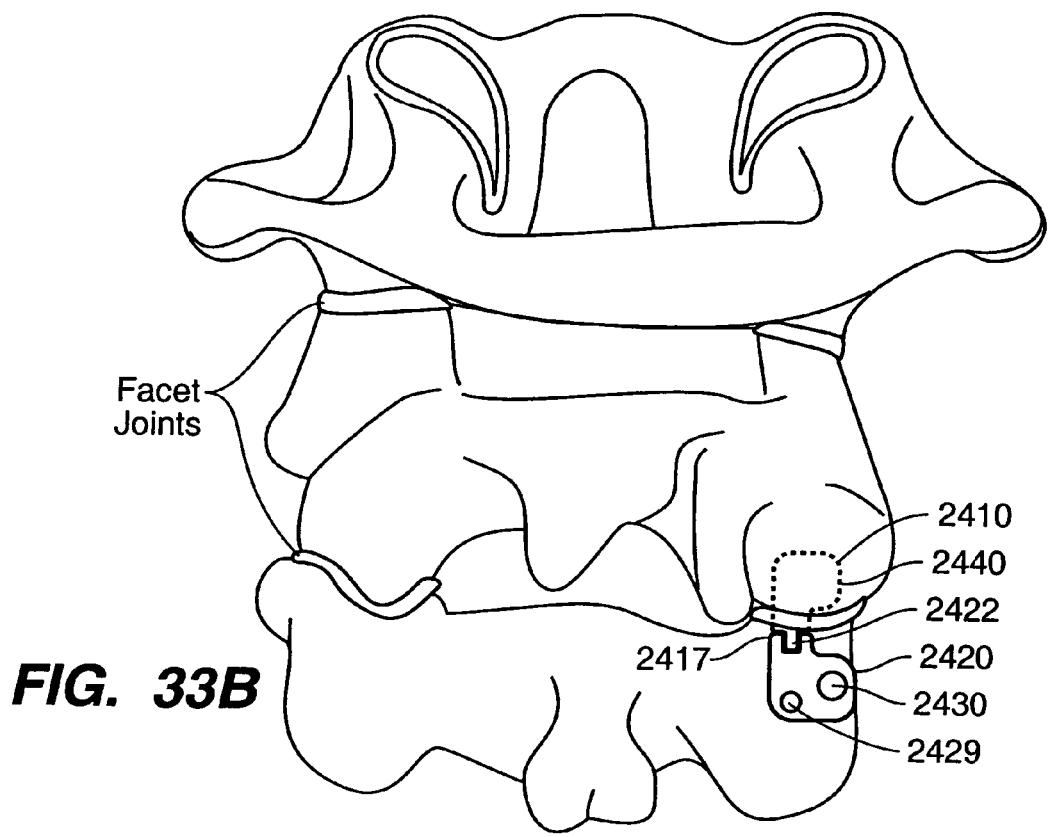

The present invention further includes a method of implanting the implant 2400 (FIGS. 33A, 33B). To insert the artificial facet joint spacer or inter-facet joint spacer 2410, a facet joint is accessed and an incision or a pair of incisions is made in the capsular ligament, the joint capsule, and the synovial membrane so that the thinned edge 2412 of the implant 2400 can be urged into the cervical facet joint through these tissues. The capsular ligament and the joint capsule and other soft tissues around the cervical facet joint are allowed to remain substantially intact, except for the small incision, and will be sutured and allowed to heal around the implant 2400. If desired, the cervical facet joint can be distracted prior to urging the curved section 2440 with the thinned edge 2412 of the artificial facet joint spacer or inter-facet joint spacer 2410 into the cervical facet joint. Once the curved section 2440 of the artificial facet joint spacer or inter-facet joint spacer 2410 with the thinned edge 2412 is urged into the cervical facet joint, implant 2400 is pivoted, preferably about 90 degrees, so that the second bore 2429 is placed medially relative to the first bore 2430. This allows the artificial facet joint spacer or inter-facet joint spacer 2410 to be positioned in the facet joint. It is noted that the overall size, including the isthmus 2417, of the artificial facet joint spacer or inter-facet joint spacer 2410, as that of 2310, can be somewhat smaller than in prior embodiments to allow the artificial facet joint spacer or inter-facet spacer to be positioned within the edges of the facet joint with the joint capsule substantially intact. The lateral mass plate 2420 then can be bent downward about the hinge 2422 into position adjacent the lateral mass or lamina of the spine of the patient, which position will depend upon the anatomy of an individual patient's cervical spine.

Once the lateral mass plate 2420 is positioned adjacent to the bone, preferably the lateral mass of a cervical vertebra, a first bone screw can be inserted through the first bore 2430 through the lateral mass plate 2420 and become embedded into the bone of the lateral mass of the cervical vertebra to anchor the implant 2400. After the bone screw is embedded, a locking screw is inserted through the second bore 2429 of the lateral mass plate 2420, the second bore 2429 medial to the first bore 2430. The locking screw has a chisel end that allows the locking screw to dig into the bone without use of a tool to pre-cut a bore. Alternatively, a bore can be pre-cut and a locking screw without a chisel end can be used. As the locking screw is embedded in the bone, the locking head of the locking screw is brought into proximity with the head of the bone screw to block its backward movement so that the implant 2400 remains anchored with the bone screw, i.e., so that the bone screw cannot back out of the bone. The embedded locking screw also serves to prevent rotational displacement of implant 2400, while blocking backward displacement of the first bone screw.

The foregoing description of the present invention has been presented for purposes of illustration and description. It is not intended to be exhaustive or to limit the invention to the precise forms disclosed. Many modifications and variations will be apparent to practitioners skilled in this art. The embodiments were chosen and described in order to explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. A facet joint implant that addresses spinal stenosis and other ailments of the spine while maintaining mobility of the facet joint, the implant comprising:
    an inter-facet joint spacer sized to fit between adjacent superior and inferior facets, the inter-facet joint spacer having an upper surface adapted to support the inferior facet and a lower surface adapted to support the superior facet;
    an anchoring plate having a connecting portion pivotably attached to the spacer, the connecting portion configured to freely pivot the anchoring plate relative to the spacer, the inter-facet joint spacer being sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer;
    a bone screw;
    a locking screw;
    the anchoring plate receives the bone screw and the locking screw; and
    wherein the locking screw is adapted to self-cut into a vertebra and to block the bone screw, the locking screw and the bone screw adapted to anchor the anchoring plate to the vertebra,
    wherein the locking screw is positioned medially, relative to the bone screw in the patient.

2. The implant of claim 1 wherein the locking screw has a head that blocks the bone screw from at least one of a backward displacement and a rotational displacement.

3. The implant of claim 1 wherein the locking screw further comprises a chisel-point end, wherein the chisel point end self-cuts the locking screw into the vertebra.

4. The implant of claim 1 wherein the locking screw and the bone screw are adapted to prevent at least one of a backward displacement and a rotational displacement of the implant.

5. The implant of claim 1 wherein said connecting portion is comprised of a flexible material.

6. The facet joint implant of claim 1, wherein the inter-facet joint spacer, the connecting portion, and the anchoring plate form an hour-glass shape, with the connecting portion forming the isthmus.

7. The facet joint implant of claim 1, wherein the inter-facet joint spacer and the connecting portion are P-shaped.

8. A facet joint implant that addresses spinal stenosis and other ailments of the spine while maintaining mobility of the facet joint, the implant comprising:
    an inter-facet joint spacer freely pivotably connected to an anchoring plate at a connecting portion, the inter-facet joint spacer having an upper surface adapted to support an inferior facet and a lower surface adapted to support a superior facet, the inter-facet joint spacer being sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer;
    a bone screw;
    a locking screw;
    the anchoring plate receives the bone screw and the locking screw; and
    wherein the locking screw is adapted to self-cut into a vertebra and to block the bone screw, the locking screw and the bone screw adapted to anchor the anchoring plate to the vertebra,
    wherein said connection is a hinge.

9. The implant in claim 1 wherein the anchoring plate has a first bore that receives the bone screw and a second bore that receives the locking screw.

10. A facet joint implant that addresses spinal stenosis and other ailments of the spine while maintaining mobility of the facet joint, the implant comprising:
    an inter-facet joint spacer flexibly connected to an anchoring plate at a connecting portion, the inter-facet joint spacer having an upper surface adapted to support an inferior facet and a lower surface adapted to support a superior facet, the inter-facet joint spacer being sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer;
    only one bone screw;
    only one locking screw;
    the anchoring plate receives the bone screw and the locking screw; and
    wherein the locking screw is adapted to self-cut into a vertebra and to block the bone screw, the locking screw and the bone screw adapted to anchor the anchoring plate to the vertebra,
    wherein the anchoring plate has a first bore that receives the bone screw and a second bore that receives the locking screw, and wherein when the implant is adapted to be implanted from the right side of a patient and the second bore is positioned to the left of the first bore when the implant is viewed from a posterior perspective.

11. A facet joint implant that addresses spinal stenosis and other ailments of the spine while maintaining mobility of the facet joint, the implant comprising:
an inter-facet joint spacer flexibly connected to an anchoring plate at a connecting portion, the inter-facet joint spacer having an upper surface adapted to support an inferior facet and a lower surface adapted to support a superior facet, the inter-facet joint spacer being sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer;
only one bone screw;
only one locking screw;
the anchoring plate receives the bone screw and the locking screw; and
wherein the locking screw is adapted to self-cut into a vertebra and to block the bone screw, the locking screw and the bone screw adapted to anchor the anchoring plate to the vertebra,
wherein the anchoring plate has a first bore that receives the bone screw and a second bore that receives the locking screw, and
wherein when the implant is adapted to be implanted from the left side of a patient and the second bore is positioned to the right of the first bore when the implant is viewed from a posterior perspective.

12. A facet joint implant that addresses spinal stenosis and other ailments of the spine while maintaining mobility of the facet joint, the implant comprising:
an inter-facet joint spacer;
an anchoring plate pivotably coupled to the spacer at a connecting portion, the anchoring plate configured to freely pivot relative to the spacer from a first insertion position to a second insertion position, wherein the first position is configured to introduce the spacer into the joint and the second position is configured to conform the plate to a vertebral bone surface at an angle to the joint, the plate having a first bore and a second bore, the inter-facet joint spacer being sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer;
a bone screw;
a locking screw;
the first bore receives and guides the bone screw into a vertebra to anchor the implant;
the second bore receives the locking screw; and
the locking screw includes a head that prevents displacement of the bone screw, and a chisel end adapted to self-cut the locking screw into the vertebra;
wherein the locking screw is positioned medially relative to the bone screw in a patient.

13. The implant of claim 12, wherein the anchoring plate in the first insertion position is oriented about 180 degrees relative to the inter-facet joint spacer, and wherein the anchoring plate in the second insertion position is oriented less than 180 degrees relative to the inter-facet joint plate.

14. A facet joint implant for treating ailments of the spine while maintaining mobility of the facet joint, the implant comprising:
an inter-facet joint spacer having an upper surface configured to support an inferior facet of an upper vertebra and a lower surface configured to support a superior facet of a lower vertebra;
an anchoring plate freely pivotably connected to the inter-facet joint spacer at a connecting portion, the anchoring plate having first and second screw receiving portions;
wherein the inter-facet joint spacer being sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer, the connecting portion being offset relative to the inter-facet joint spacer;
only one bone screw configured to attach the anchoring plate to a vertebra through the first screw receiving portion;
a locking screw configured to attach the anchoring plate to a vertebra through the second screw receiving portion, the locking screw being configured to self-cut into a vertebra and to restrict removal of the bone screw, the locking screw and the bone screw being configured to cooperatively anchor the anchoring plate to the vertebra in a manner that the locking screw restricts rotation of the anchoring plate about the bone screw.

15. The implant of claim 14, wherein the inter-facet joint spacer is formed of only one plate.

16. The implant of claim 15, wherein the upper surface of the single plate has a convex shape and the lower surface has a concave shape.

17. The implant of claim 14, wherein the inter-facet joint spacer includes a distal end and a proximal end, the proximal end being freely pivotably connected to the anchoring plate, the distal end having a thickness less than a thickness of the proximal end.

18. The implant of claim 14, wherein the locking screw includes a head configured to restrict removal the bone screw from at least one of a backward displacement and a rotational displacement when the bone screw and the locking screw are located through the first and second screw receiving portions.

19. The implant of claim 14, wherein the locking screw further comprises a chisel-point end configured to self-cut the locking screw into the vertebra.

20. The implant of claim 14, wherein the locking screw is positioned medially, relative to the bone screw in the patient.

21. The implant of claim 14, wherein the locking screw and the bone screw are adapted to prevent at least one of a backward displacement and a rotational displacement of the implant.

22. The implant of claim 14, wherein the anchoring plate and the inter-facet joint spacer are flexibly connected at a connection feature comprised of a flexible material.

23. The implant of claim 14, wherein the anchoring plate and the inter-facet joint spacer are flexibly connected at a hinge.

24. The implant in claim 14, wherein the first and second screw receiving portions are first and second bores respectively sized to receive the bone screw and the locking screw.

25. The implant of claim 24, wherein when the implant is adapted to be implanted from the right side of a patient and the second bore is positioned to the left of the first bore when the implant is viewed from a posterior perspective.

26. The implant of claim 24, wherein when the implant is adapted to be implanted from the left side of a patient and the second bore is positioned to the right of the first bore when the implant is viewed from a posterior perspective.

27. The implant of claim 14, wherein the first and second screw receiving portions are first and second screw-receiving bores and are the only screw-receiving bores in the anchoring plate, the screw-receiving bores having different diameters and being spaced adjacent to each other so that a portion of the locking screw overlaps a portion of the bone screw.

28. A facet joint implant for treating ailments of the spine while maintaining mobility of the facet joint, the implant comprising:
    an inter-facet joint spacer having an upper surface configured to interface with an inferior facet of an upper vertebra and a lower surface configured to interface with a superior facet of a lower vertebra;
    only one anchoring plate freely pivotably connected to the inter-facet joint spacer at a connecting portion and being configured to secure the inter-facet joint spacer in place on a single one of the upper and lower vertebrae, the anchoring plate having a screw receiving portion, wherein the inter-facet joint spacer is sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer, the connecting portion being offset relative to the inter-facet joint spacer;
    only one bone screw configured to attach the anchoring plate to said single one of the upper and lower vertebrae through the screw receiving portion;
    only one locking screw configured to attach the anchoring plate to said single one of the upper and lower vertebrae through the screw receiving portion, the locking screw being configured to restrict removal of the bone screw, the locking screw and the bone screw being configured to cooperatively anchor the anchoring plate to the vertebra in a manner that the locking screw restricts rotation of the anchoring plate about the bone screw.

29. The implant of claim 28, wherein the inter-facet joint spacer is formed of a single plate.

30. The implant of claim 29, wherein the upper surface of the single plate has a convex shape and the lower surface has a concave shape.

31. The implant of claim 28, wherein the locking screw includes a head configured to restrict removal the bone screw from at least one of a backward displacement and a rotational displacement when the bone screw and the locking screw are located through the screw receiving portion.

32. A method for implanting a facet joint implant into a facet joint, the method comprising the steps of:
    accessing a facet joint;
    urging an inter-facet joint spacer into the facet joint so that an upper surface of spacer supports an inferior facet of an upper vertebra and a lower surface of the spacer supports a superior facet of a lower vertebra, the inter-facet joint spacer being freely pivotably connected to an anchoring plate at a connecting portion, wherein the inter-facet joint spacer is sized with a first overall width measured laterally across the inter-facet joint spacer, the connecting portion having a second overall width measured laterally across the connecting portion in a direction substantially parallel to the lateral direction of the first width, the second overall width being less than the first overall width such that the connecting portion is narrower than the inter-facet joint spacer;
    driving only one bone screw through the anchoring plate freely pivotably connected to the inter-facet joint spacer and into a lateral mass or lamina of a vertebra to anchor the anchoring plate to the bone screw; and
    driving only one locking screw through the anchoring plate into a lateral mass or lamina of a vertebra in a manner that both restricts removal of the bone screw and restricts rotation of the anchoring plate about the bone screw.

33. The method of claim 32, wherein the locking screw comprises a chisel end, and wherein driving the locking screw comprises self-cutting a locking screw channel into the vertebra with the chisel end.

34. The method of claim 32, further comprising distracting the facet joint prior to urging the inter-facet joint spacer into the facet joint.

35. The method of claim 32, wherein driving the bone screw further comprises:
    guiding the bone screw by a first bore in the anchoring plate; and
    driving the bone screw into the lateral mass or lamina through the first bore;
    and wherein driving the locking screw comprises:
    guiding the locking screw by a second bore in the anchoring plate; and
    driving the locking screw into the lateral mass or lamina through the second bore.

36. The method of claim 32 wherein restricting removal of the bone screw comprises causing a head of the locking screw to overlap with and contact a head of the bone screw to prevent the bone screw from at least one of backward or rotational displacement.

37. A method for implanting a facet joint implant into a facet joint, the method comprising the steps of:
    accessing a facet joint;
    urging an inter-facet joint spacer into the facet joint so that an upper surface of spacer supports an inferior facet of an upper vertebra and a lower surface of the spacer supports a superior facet of a lower vertebra;
    driving only one bone screw through the anchoring plate freely pivotably connected at a connection to the inter-facet joint spacer and into a lateral mass or lamina of a vertebra to anchor the anchoring plate to the bone screw; and
    driving only one locking screw through the anchoring plate into a lateral mass or lamina of a vertebra in a manner that both restricts removal of the bone screw and restricts rotation of the anchoring plate about the bone screw,
        wherein the connection comprises a hinge, the hinge and spacer comprising a P-shape configured to be inserted into the facet joint with most of a facet capsule, a facet capsule ligament, and a synovial membrane left intact, the spacer having at least one edge with a lateral curvature extending medially from the hinge establishing a maximum width of the spacer, the P-shape narrowing to an isthmus at the hinge and the at least one edge being thinned along the lateral curvature; and the urging step comprising:
orienting the spacer transverse to the facet joint,
introducing the at least one edge through an incision, the incision having a width less than the maximum width of the spacer,
advancing the at least one edge until the spacer is approximately, centrally positioned within the facet capsule, and
rotating the spacer about 90 degrees.

* * * * *